United States Patent
Koch et al.

(10) Patent No.: US 10,494,616 B2
(45) Date of Patent: Dec. 3, 2019

(54) CELLOBIOSE PHOSPHORYLASE

(71) Applicant: Pfeifer & Langen GmbH & Co. KG, Köln (DE)

(72) Inventors: Timo Johannes Koch, Elsdorf (DE); Thomas Hässler, Köln (DE); Birgit Brucher, Leipzig (DE); Andreas Vogel, Leipzig (DE)

(73) Assignee: PFEIFER & LANGEN GMBH & CO. KG, Cologne (DE)

( * ) Notice: Subject to any disclaimer, the term of this patent is extended or adjusted under 35 U.S.C. 154(b) by 0 days.

(21) Appl. No.: 15/506,215

(22) PCT Filed: Sep. 10, 2015

(86) PCT No.: PCT/EP2015/070722
§ 371 (c)(1),
(2) Date: Feb. 23, 2017

(87) PCT Pub. No.: WO2016/038141
PCT Pub. Date: Mar. 17, 2016

(65) Prior Publication Data
US 2018/0216086 A1    Aug. 2, 2018

(30) Foreign Application Priority Data

Sep. 10, 2014 (EP) .................... 14184301
Sep. 10, 2014 (EP) .................... 14184302
Oct. 29, 2014  (EP) .................... 14190891

(51) Int. Cl.
| | | |
|---|---|---|
| *C12P 19/02* | (2006.01) | |
| *C12N 9/10* | (2006.01) | |
| *C12P 19/12* | (2006.01) | |
| *C13K 11/00* | (2006.01) | |
| *C13K 1/02* | (2006.01) | |
| *C12P 19/18* | (2006.01) | |

(52) U.S. Cl.
CPC ............ *C12N 9/1051* (2013.01); *C12P 19/02* (2013.01); *C12P 19/12* (2013.01); *C12P 19/18* (2013.01); *C12Y 204/0102* (2013.01); *C13K 1/02* (2013.01); *C13K 11/00* (2013.01)

(58) Field of Classification Search
CPC .................................................. C12N 9/1051
See application file for complete search history.

(56) References Cited

U.S. PATENT DOCUMENTS 5,849,529 A    12/1998  Hayashi et al.

FOREIGN PATENT DOCUMENTS

| EP | 0423768 | 4/1991 |
| WO | 2009080774 | 7/2007 |
| WO | 2012109274 | 8/2012 |

OTHER PUBLICATIONS

Lucas et al. 2011; Complete sequence of Cellvibrio gilvus ATCC 13127. UniprotKB-F8A760, alignment.*
Hidaka et al. 2006; Structural dissection of the reaction mechanism of cellobiose phosphorylase. Biochem. J. 298: 37-43, with alignment.*
DeGroeve et al. 2010; Construction of cellobiose phosphorylase variants with broadened acceptor specificity towards anomerically substituted glucosides. Biotech Bioengin. 107(3): 413-420.*
Lucas et al., 2011. Complete sequence of Cellvibrio gilvus ATCC 13127. Sequence Alignmnets only. 4 pages.*
Database Genesq XP-002736368 (2012) "Cellodextrin degradation related polypeptide" SEQ ID 170" AZY80852 standard; protein; 822 AA 1 page.
Database Genesq XP-002736369 (2012) "Cellodextrin degradation related polypeptide" SEQ ID 151" AZY80833 standard protein; 822 AA 1 Page.
De Groeve et al (2009) "Creating lactose phosphorylase enzymes by dirested evolution of cellobiose phosphorylase," Protein Engineering, Design & Selection 22(7): 393-399.
De Groeve et al. (2010) "Construction of cellobiose phosphorylase variants with broadened acceptor specifically towards anomerically substituted glucosides," Biotechnology and Bioengineering 107: 413-420.
De Groeve et al. (2010) "Development and application of a screening assay for glycoside phosphorylases," Analytical Biochemistry 401: 162-167.
De Groeve et al. (2011) "Engineering of cellobiose phosphorylase for glycoside synthesis," Journal of Biotechnology 156: 253-260.
Desmet et al. (2001) "Broadening the synthetic potential of dsaccharide phosphorylases through enzyme engineering," Process Biochemistry, Elsevier 47 (1): 11-17.
Hidaka et al. (2006) "Structural dissection of the reaction mechanism of cellobiose phosphorylase," Biochem J. 398: 37-43.
Nidetzky et al. (2004)"Cellobiose phosphorylase from Cellulomonas uda: gene cloning and expression in *Escherichia coli*, and application of the recombinant enzyme in a 'glycosynthase-type' reaction," Journal of Molecular Catalysis 29(1-6): 241-248.
CELGI UniProtKB—F8A760 (Oct. 30, 2018).

* cited by examiner

*Primary Examiner* — Karen Cochrane Carlson
(74) *Attorney, Agent, or Firm* — The Dobrusin Law Firm, PC

(57) ABSTRACT

The invention relates to a cellobiose phosphorylase, which catalyzes, among other things, the synthesis of cellobiose from glucose 1-phosphate and glucose. The cellobiose phosphorylase according to the invention can be understood as a mutation of the cellobiose phosphorylase from *Cellulomonas uda*. In comparison to cellobiose phosphorylase of the wild type, the cellobiose phosphorylase according to the invention is distinguished by improved activity and process stability, in particular temperature stability, and lower product inhibition and therefore is especially suitable for use in industrial processes.

10 Claims, No Drawings
Specification includes a Sequence Listing.

ID NO:1

CELLOBIOSE PHOSPHORYLASE

CROSS-REFERENCE TO RELATED APPLICATIONS

This application is the U.S. national phase under 35 U.S.C. § 371 of PCT International Application No. PCT/EP2015/070722, which has an international filing date of Sep. 10, 2015 and designated the United States of America, which application claims benefit of priority to EP Application Nos. 14184301.1, filed Sep. 10, 2014, 14184302.9, filed Sep. 10, 2014, and 14190891.3, filed Oct. 29, 2014, the disclosures of each of which are incorporated by reference herein.

The invention relates to a cellobiose phosphorylase, which catalyzes, among other things, the synthesis of cellobiose from glucose 1-phosphate and glucose. The cellobiose phosphorylase according to the invention can be understood as a mutant of the cellobiose phosphorylase from *Cellulomonas uda*. In comparison to cellobiose phosphorylase of the wild type, the cellobiose phosphorylase according to the invention is distinguished by improved activity and process stability, in particular temperature stability, and lower reactant and product inhibitions and therefore is especially suitable for use in industrial processes.

Cellobiose phosphorylases catalyze the cleavage of cellobiose (D-glucosyl-β-(1→4)-D-glucose) to glucose and glucose 1-phosphate. Aside from this phosphorolytic activity, said enzymes, under suitable conditions, are also capable of conversely catalyzing the synthesis of cellobiose from glucose 1-phosphate and glucose.

Cellobiose is a natural disaccharide which constitutes the basic building block of cellulose. Cellobiose is becoming increasingly attractive to the food and feed sectors.

Cellobiose may be prepared by either chemical or enzymatic hydrolysis of cellulose. GB 2 438 573 describes a method of obtaining cellobiose, which comprises hydrolyzing cellulose, increasing the proportion of cellobiose in the sugar solution in relation to other saccharides by ultrafiltration, and subsequently purifying the cellobiose by crystallization.

As an alternative to preparing cellobiose from cellulose, cellobiose is synthesized using cellobiose phosphorylases. The key intermediate of this synthesis is glucose 1-phosphate which may be obtained either by phosphorylizing starch by means of an alpha-glucan phosphorylase or by phosphorylizing sucrose by means of a sucrose phosphorylase; the latter cleaves sucrose to give glucose 1-phosphate and fructose.

EP 0 423 768 discloses a method of preparing cellobiose, starting from sucrose and using a sucrose phosphorylase, a glucose isomerase and a cellobiose phosphorylase. Said method comprises the following steps: (1) cleaving sucrose in the presence of orthophosphate under catalysis by sucrose phosphorylase to give glucose 1-phosphate and fructose; (2) isomerizing fructose to glucose under catalysis by glucose isomerase; (3) synthesizing cellobiose from glucose and glucose 1-phosphate under catalysis by cellobiose phosphorylase, with removal of orthophosphate; (4) partially working up cellobiose from the reaction mix and recirculating part of the remaining orthophosphate-containing reaction mix in step (1). Industrial cellobiose production starting from glucose and glucose 1-phosphate requires a cellobiose phosphorylase having high activity and good process and thermal stability.

One possible way of optimizing enzymes is the application of enzyme engineering which aims at developing variants of a parent enzyme with improved properties. Enzyme engineering has previously been applied to a cellobiose phosphorylase from *Cellulomonas uda* with the aim of modifying the substrate specificity of the enzyme.

De Groeve et al. Protein Engineering, Design & Selection, 2009, 22:393-399 disclose enzyme variants with altered substrate specificity, which have a markedly increased activity as lactose phosphorylase and may be employed for preparing galactose 1-phosphate.

De Groeve et al., Biotechnology and Bioengineering, 2010, 107:413-420 disclose further variants of *Cellulomonas uda* cellobiose phosphorylase with altered substrate specificity, which have a broader acceptor specificity for substituted glycosides.

Desmet et al., Process Biochemistry, Elsevier, 47, No. 1, 2001, 11-17 relates to broadening the synthetic potential of disaccharide phosphorylases by enzyme engineering.

Nidetzky et al., Journal of Molecular Catalysis B:Enzymatic, 29, No. 1-6, 2004, 241-248 relates to *Cellulomonas uda* cellobiose phosphorylase, expression in *E. coli*, and use of the recombinant enzyme.

U.S. Pat. No. 5,849,529 relates to a cellobiose phosphorylase gene and the correspondingly encoded protein.

WO 2009/080774 discloses lactose phosphorylases obtained by mutation of *Cellulomonas uda* cellobiose phosphorylase, which may be used for preparing galactose 1-phosphate or lactose.

WO 2012/109274 relates to host cells which harbor two or more recombinant cellodextrin transporters, a recombinant cellodextrin phosphorylase, a recombinant ss-glucosidase, a recombinant phosphoglucomutase, or a recombinant hexokinase.

Aside from engineering *Cellulomonas uda* cellobiose phosphorylase to modify substrate specificity, so far no other extensive approaches to optimizing *Cellulomonas uda* cellobiose phosphorylase or the other cellobiose phosphorylases by engineering are known.

There is a need for cellobiose phosphorylases which are suited to efficient synthesis of cellobiose from glucose 1-phosphate and glucose on an industrial scale.

It is an object of the invention to provide a cellobiose phosphorylase with improved properties. In view of the synthesis of cellobiose, said cellobiose phosphorylase should distinguish itself from known cellobiose phosphorylases by an improved activity and process stability, in particular thermal stability, and lower reactant and product inhibitions.

This object is achieved by the subject matter of the claims.

A first aspect of the invention relates to a cellobiose phosphorylase comprising an amino acid sequence which is at least 80% or at least 81%, more preferably at least 82% or at least 83%, and in particular at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, identical to the amino acid sequence set forth in SEQ ID NO:1 and which, compared to SEQ ID NO:1, comprises at least one amino acid mutation, preferably at least two or at least three amino acid mutations, in each case independently of one another, in a sequence section A) which corresponds to positions 100 to 295 as per SEQ ID NO:1; wherein the amino acid sequence of the cellobiose phosphorylase of the invention preferably does not have the K283H amino acid mutation; and/or in a sequence section B) which corresponds to positions 340 to 370 as per SEQ ID NO:1; and/or in a sequence section C) which corresponds to positions 560 to 635 as per SEQ ID NO:1, wherein the amino acid sequence of the cellobiose phosphorylase of the invention preferably does not have the A584E amino acid mutation; and/or in a sequence section D) which corresponds to positions 685 to 745 as per SEQ ID NO:1; wherein the amino acid sequence of the cellobiose phosphorylase of the invention preferably has neither the L705Q amino acid mutation nor the L705V amino acid mutation; and/or in a sequence section E) which corresponds to positions 755 to 810 as per SEQ ID NO:1; wherein the amino acid sequence of the cellobiose phosphorylase of the invention preferably has neither the T788E amino acid mutation nor T788A nor T788V;

preferably with the proviso that the amino acid sequence of the cellobiose phosphorylase of the invention, compared to SEQ ID NO:1, (i) preferably has no amino acid mutation in position 188 and/or no amino acid mutation in position 283 and/or no amino acid mutation in position 584 and/or no amino acid mutation in position 705; particularly preferably has none of the amino acid mutations specified above; and/or (ii) preferably has no amino acid mutation in position 788, provided that the amino acid sequence of the cellobiose phosphorylase of the invention, compared to SEQ ID NO:1, has the K283H amino acid mutation;

particularly preferably has none of the amino acid mutations specified above under (i) and (ii).

In a preferred embodiment, the cellobiose phosphorylase of the invention does not comprise the K283H amino acid mutation and/or the A584E amino acid and/or the L705Q amino acid mutation and/or the L705V amino acid mutation and/or the T788E amino acid mutation and/or the T788A amino acid mutation and/or the T788V amino acid mutation; particularly preferably any of the amino acid mutations specified above.

In a preferred embodiment, the cellobiose phosphorylase of the invention comprises an amino acid sequence which is at least 80% or at least 81%, more preferably at least 82% or at least 83%, and in particular at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, identical to the amino acid sequence set forth in SEQ ID NO:1 and which, compared to SEQ ID NO:1, comprises at least one amino acid mutation, preferably at least two or at least three amino acid mutations, in each case independently of one another, in a sequence section B) which corresponds to positions 340 to 370 as per SEQ ID NO:1; and/or in a sequence section C) which corresponds to positions 560 to 635 as per SEQ ID NO:1, wherein the amino acid sequence of the cellobiose phosphorylase of the invention preferably does not have the A584E amino acid mutation; and/or in a sequence section D) which corresponds to positions 685 to 745 as per SEQ ID NO:1; wherein the amino acid sequence of the cellobiose phosphorylase of the invention preferably has neither the L705Q amino acid mutation nor the L705V amino acid mutation; and/or in a sequence section E) which corresponds to positions 755 to 810 as per SEQ ID NO:1; wherein the amino acid sequence of the cellobiose phosphorylase of the invention preferably has neither the T788E amino acid mutation nor the T788A amino acid mutation nor the T788V amino acid mutation.

In a preferred embodiment, the cellobiose phosphorylase of the invention comprises the sequence sections B), D) and E) according to this embodiment stated above.

In a preferred embodiment, the cellobiose phosphorylase of the invention comprises an amino acid sequence which is at least 80% or at least 81%, more preferably at least 82% or at least 83%, and in particular at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, identical to the amino acid sequence set forth in SEQ ID NO:1 and which, compared to SEQ ID NO:1, comprises at least one amino acid mutation, preferably at least two or at least three amino acid mutations, in each case independently of one another, in a sequence section A) which corresponds to positions 100 to 295 as per SEQ ID NO:1; wherein the amino acid sequence of the cellobiose phosphorylase of the invention preferably does not have the K283H amino acid mutation; and/or in a sequence section B) which corresponds to positions 340 to 370 as per SEQ ID NO:1; and/or in a sequence section C) which corresponds to positions 560 to 635 as per SEQ ID NO:1, wherein the amino acid sequence of the cellobiose phosphorylase of the invention preferably does not have the A584E amino acid mutation; and/or in a sequence section D) which corresponds to positions 685 to 745 as per SEQ ID NO:1; wherein the amino acid sequence of the cellobiose phosphorylase of the invention preferably has neither the L705Q amino acid mutation nor the L705V amino acid mutation.

In a preferred embodiment, the cellobiose phosphorylase of the invention comprises an amino acid sequence which is at least 80% or at least 81%, more preferably at least 82% or at least 83%, and in particular at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, identical to the amino acid sequence set forth in SEQ ID NO:1 and which, compared to SEQ ID NO:1, comprises at least one amino acid mutation, preferably at least two or at least three amino acid mutations, in each case independently of one another, in a sequence section B) which corresponds to positions 340 to 370 as per SEQ ID NO:1; and/or in a sequence section C) which corresponds to positions 560 to 635 as per SEQ ID NO:1, wherein the amino acid sequence of the cellobiose phosphorylase of the invention preferably does not have the A584E amino acid mutation; and/or in a sequence section D) which corresponds to positions 685 to 745 as per SEQ ID NO:1; wherein the amino acid sequence of the cellobiose phosphorylase of the invention preferably has neither the L705Q amino acid mutation nor the L705V amino acid mutation.

In a particularly preferred embodiment, the cellobiose phosphorylase of the invention comprises an amino acid sequence which is at least 80% or at least 81%, more preferably at least 82% or at least 83%, and in particular at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, identical to the amino acid sequence set forth in SEQ ID NO:1 and which, compared to SEQ ID NO:1, comprises at least one amino acid mutation, preferably at least two or at least three amino acid mutations, in each case independently of one another, in a sequence section D) which corresponds to positions 685 to 745 as per SEQ ID NO:1. The amino acid sequence of the cellobiose phosphorylase of the invention here preferably has neither the L705Q amino acid mutation nor the L705V amino acid mutation.

In a particularly preferred embodiment, the cellobiose phosphorylase of the invention comprises an amino acid sequence which is at least 80% or at least 81%, more preferably at least 82% or at least 83%, and in particular at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, identical to the amino acid sequence set forth in SEQ ID NO:1 and which, compared to SEQ ID NO:1, comprises at least one amino acid mutation, preferably at least two or at least three amino acid mutations, in each case independently of one another, in a sequence section D) which corresponds to positions 685 to 745 as per SEQ ID NO:1. The amino acid sequence of the cellobiose phosphorylase of the invention here preferably has neither the T788E amino acid mutation nor the T788A amino acid mutation nor the T788V amino acid mutation.

Surprisingly, improved cellobiose phosphorylases were found to be obtainable by means of amino acid mutations in certain sequence sections of the amino acid sequence of *Cellulomonas uda* cellobiose phosphorylase (wild type, SEQ ID NO:1).

In comparison with cellobiose phosphorylase of the wild type, the cellobiose phosphorylase of the invention is distinguished by improved activity and process stability, in particular thermal stability, and lower reactant and product inhibitions and therefore is especially suitable for use in industrial processes. The improved properties result in an improved space-time yield and an increased ratio of synthesis to phosphorolysis.

The cellobiose phosphorylase of the invention comprises an amino acid sequence which is at least 80%, preferably at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, identical to the amino acid sequence set forth in SEQ ID NO:1.

According to the invention, "identity" is defined as the percentage of identical matches between two comparative sequences with optimum alignment. For optimum alignment, gaps may be introduced into either of the two sequences. Preferably, identity between two comparative sequences is determined using the Smith and Waterman algorithm (Smith T F, Waterman M S J (1981) Mol. Biol. 147, 195-197), preferably using the WATER computer program from the EMBOSS package which is freely available and which incorporates the Smith and Waterman algorithm (Reis P, Longden I, Bleasby A (2000) Trends in Genetics 16, 276-277). Preference is given here to using BLOSUM62 for the substitution matrix with a GOP (gap opening penalty) of 10 and a GEP (gap extension penalty) of 0.5.

An amino acid mutation for the purposes of the present invention is defined as a replacement of the amino acid of a cellobiose phosphorylase wild-type sequence, preferably of the cellobiose phosphorylase wild-type sequence set forth in SEQ ID NO:1, by a different proteinogenic amino acid.

In a preferred embodiment of the cellobiose phosphorylase of the invention, sequence section A) comprises positions 155 to 289 as per SEQ ID NO:1. Preferably, sequence section A) is divided into sequence sections $A_1$), $A_2$), $A_3$), $A_4$), $A_5$), $A_6$), $A_7$), $A_8$) and $A_9$), wherein the cellobiose phosphorylase of the invention, when comprising at least one amino acid mutation, preferably at least two or at least three amino acid mutations in sequence section A) compared to SEQ ID NO:1, comprises said at least one amino acid mutation, preferably at least two or at least three amino acid mutations in each case independently of one another preferably in any of the $A_1$), $A_2$), $A_3$), $A_4$), AO, $A_6$), $A_7$), $A_8$) and $A_9$) sequence sections, and wherein sequence section $A_1$) corresponds to positions 155 to 167 as per SEQ ID NO:1;
sequence section $A_2$) corresponds to positions 158 to 170 as per SEQ ID NO:1;
sequence section $A_3$) corresponds to positions 160 to 172 as per SEQ ID NO:1;
sequence section $A_4$) corresponds to positions 163 to 175 as per SEQ ID NO:1;
sequence section $A_5$) corresponds to positions 164 to 176 as per SEQ ID NO:1;
sequence section $A_6$) corresponds to positions 182 to 194 as per SEQ ID NO:1;
sequence section $A_7$) corresponds to positions 190 to 202 as per SEQ ID NO:1;
sequence section $A_8$) corresponds to positions 214 to 226 as per SEQ ID NO:1; and
sequence section $A_9$) corresponds to positions 277 to 289 as per SEQ ID NO:1.

Preferably, the cellobiose phosphorylase of the invention comprises at least one amino acid mutation, preferably at least two or at least three amino acid mutations compared to SEQ ID NO:1, in each case independently of one another in sequence section A), wherein said at least one amino acid mutation, preferably at least two or at least three amino acid mutations, in each case independently of one another is/are preferably located in any of sequence sections $A_1$), $A_2$), $A_3$), $A_4$), $A_5$), $A_6$), $A_7$), $A_8$) and $A_9$), but preferably not in sequence section $A_6$).

In preferred embodiments, the cellobiose phosphorylase of the invention comprises no amino acid mutation in position 188 and/or no amino acid mutation in position 283 and/or no amino acid mutation in position 584 and/or no amino acid mutation in position 788 compared to SEQ ID NO:1.

In preferred embodiments, the amino acid sequence of the cellobiose phosphorylase of the invention has, compared to SEQ ID NO:1,
(i) preferably has no amino acid mutation in position 188 and/or no amino acid mutation in position 283 and/or no amino acid mutation in position 584 and/or no amino acid mutation in position 705; particularly preferably none of the amino acid mutations specified above; and/or
(ii) preferably no amino acid mutation in position 788, provided that the amino acid sequence of the cellobiose phosphorylase of the invention has the K283H amino acid mutation compared to SEQ ID NO:1;
particularly preferably none of the amino acid mutations specified above under (i) and (ii).

In a preferred embodiment, the cellobiose phosphorylase of the invention comprises an amino acid sequence which is at least 80% or at least 81%, more preferably at least 82% or at least 83%, and in particular at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, identical to the amino acid sequence set forth in SEQ ID NO:1 and which, compared to SEQ ID NO:1, comprises at least one amino acid mutation, preferably at least two or at least three amino acid mutations, in each case independently of one another,
  in a sequence section $A_1$) which corresponds to positions 155 to 167 as per SEQ ID NO:1, preferably positions 160 to 162; and/or
  in a sequence section $A_2$) which corresponds to positions 158 to 170 as per SEQ ID NO:1, preferably positions 163 to 164; and/or
  in a sequence section $A_3$) which corresponds to positions 160 to 172 as per SEQ ID NO:1, preferably positions 165 to 167; and/or
  in a sequence section $A_4$) which corresponds to positions 163 to 175 as per SEQ ID NO:1, preferably positions 168 to 169; and/or
  in a sequence section $A_5$) which corresponds to positions 164 to 176 as per SEQ ID NO:1, preferably positions 170 to 171; and/or
  in a sequence section $A_7$) which corresponds to positions 190 to 202 as per SEQ ID NO:1; and/or
  in a sequence section $A_8$) which corresponds to positions 214 to 226 as per SEQ ID NO:1; and/or
  in a sequence section $A_9$) which corresponds to positions 277 to 289 as per SEQ ID NO:1; wherein the amino acid sequence of the cellobiose phosphorylase of the invention preferably does not have the K283H amino acid mutation; and/or
  in a sequence section B) which corresponds to positions 340 to 370 as per SEQ ID NO:1; and/or
  in a sequence section C) which corresponds to positions 560 to 635 as per SEQ ID NO:1, wherein the amino acid sequence of the cellobiose phosphorylase of the invention preferably does not have the A584E amino acid mutation; and/or
  in a sequence section D) which corresponds to positions 685 to 745 as per SEQ ID NO:1; wherein the amino acid sequence of the cellobiose phosphorylase of the invention preferably has neither the L705Q amino acid mutation nor the L705V amino acid mutation; and/or
  in a sequence section E) which corresponds to positions 755 to 810 as per SEQ ID NO:1; wherein the amino acid sequence of the cellobiose phosphorylase of the invention preferably has neither the T788E amino acid mutation nor T788A nor T788V.

In a preferred embodiment, the cellobiose phosphorylase of the invention here comprises, where appropriate, additionally one further amino acid mutation in a sequence section $A_6$) which corresponds to positions 182 to 194 as per SEQ ID NO:1, preferably positions 187 to 189. In another preferred embodiment, the cellobiose phosphorylase of the invention here comprises, where appropriate, additionally no further amino acid mutation in a sequence section $A_6$) which corresponds to positions 182 to 194 as per SEQ ID NO:1, preferably positions 187 to 189.

In a preferred embodiment, the cellobiose phosphorylase of the invention comprises an amino acid sequence which is at least 80% or at least 81%, more preferably at least 82% or at least 83%, and in particular at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, identical to the amino acid sequence set forth in SEQ ID NO:1 and which, compared to SEQ ID NO:1, comprises at least one amino acid mutation, preferably at least two or at least three amino acid mutations, in each case independently of one another,
  in a sequence section $A_1$) which corresponds to positions 155 to 167 as per SEQ ID NO:1, preferably positions 160 to 162; and/or
  in a sequence section $A_2$) which corresponds to positions 158 to 170 as per SEQ ID NO:1, preferably positions 163 to 164; and/or
  in a sequence section $A_3$) which corresponds to positions 160 to 172 as per SEQ ID NO:1, preferably positions 165 to 167; and/or
  in a sequence section $A_4$) which corresponds to positions 163 to 175 as per SEQ ID NO:1, preferably positions 168 to 169; and/or
  in a sequence section $A_5$) which corresponds to positions 164 to 176 as per SEQ ID NO:1, preferably positions 170 to 171; and/or
  in a sequence section $A_7$) which corresponds to positions 190 to 202 as per SEQ ID NO:1; and/or
  in a sequence section $A_8$) which corresponds to positions 214 to 226 as per SEQ ID NO:1; and/or
  in a sequence section $A_9$) which corresponds to positions 277 to 289 as per SEQ ID NO:1; wherein the amino acid sequence of the cellobiose phosphorylase of the invention preferably does not have the K283H amino acid mutation; and/or
  in a sequence section B) which corresponds to positions 340 to 370 as per SEQ ID NO:1; and/or
  in a sequence section C) which corresponds to positions 560 to 635 as per SEQ ID NO:1, wherein the amino acid sequence of the cellobiose phosphorylase of the invention preferably does not have the A584E amino acid mutation; and/or
  in a sequence section D) which corresponds to positions 685 to 745 as per SEQ ID NO:1; wherein the amino acid sequence of the cellobiose phosphorylase of the invention preferably has neither the L705Q amino acid mutation nor the L705V amino acid mutation.

In a preferred embodiment, the cellobiose phosphorylase of the invention here comprises, where appropriate, additionally one further amino acid mutation in a sequence section $A_6$) which corresponds to positions 182 to 194 as per SEQ ID NO:1, preferably positions 187 to 189. In another preferred embodiment, the cellobiose phosphorylase of the invention here comprises, where appropriate, additionally no further amino acid mutation in a sequence section $A_6$) which corresponds to positions 182 to 194 as per SEQ ID NO:1, preferably positions 187 to 189. In a preferred embodiment, the cellobiose phosphorylase of the invention here comprises, where appropriate, additionally one further amino acid mutation in a sequence section E) which corresponds to positions 755 to 810 as per SEQ ID NO:1.

In another preferred embodiment, the cellobiose phosphorylase of the invention here comprises, where appropriate, additionally no further amino acid mutation in a sequence section E) which corresponds to positions 755 to 810 as per SEQ ID NO:1.

In preferred embodiments of the cellobiose phosphorylase of the invention,
  sequence section $A_1$) corresponds to positions 155 to 167, preferably positions 156 to 166, more preferably positions 157 to 165, even more preferably positions 158 to 164, most preferably positions 159 to 163, and in particular positions 160 to 162, as per SEQ ID NO:1; and/or
  sequence section $A_2$) corresponds to positions 158 to 170, preferably positions 159 to 169, more preferably positions 160 to 168, even more preferably positions 161 to 167, most preferably positions 162 to 166, and in particular positions 163 to 165, as per SEQ ID NO:1; and/or sequence section $A_3$) corresponds to positions 160 to 172, preferably positions 161 to 171, more preferably positions 162 to 170, even more preferably positions 163 to 169, most preferably positions 164 to 168, and in particular positions 165 to 167, as per SEQ ID NO:1; and/or sequence section $A_4$) corresponds to positions 163 to 175, preferably positions 164 to 174, more preferably positions 165 to 173, even more preferably positions 166 to 172, most preferably positions 167 to 171, and in particular positions 168 to 170, as per SEQ ID NO:1; and/or sequence section $A_5$) corresponds to positions 164 to 176, preferably positions 165 to 175, more preferably positions 166 to 174, even more preferably positions 167 to 173, most preferably positions 168 to 172, and in particular positions 169 to 171, as per SEQ ID NO:1; and/or sequence section $A_6$) corresponds to positions 182 to 194, preferably positions 183 to 193, more preferably positions 184 to 192, even more preferably positions 185 to 191, most preferably positions 186 to 190, and in particular positions 187 to 189, as per SEQ ID NO:1; and/or sequence section $A_7$) corresponds to positions 190 to 202, preferably positions 191 to 201, more preferably positions 192 to 200, even more preferably positions 193 to 199, most preferably positions 194 to 198, and in particular positions 195 to 197, as per SEQ ID NO:1; and/or sequence section $A_8$) corresponds to positions 214 to 266, preferably positions 215 to 225, more preferably positions 216 to 224, even more preferably positions 217 to 223, most preferably positions 218 to 222, and in particular positions 219 to 221, as per SEQ ID NO:1; and/or sequence section $A_9$) corresponds to positions 277 to 289, preferably positions 278 to 288, more preferably positions 279 to 287, even more preferably positions 280 to 286, most preferably positions 281 to 285, and in particular positions 282 to 284, as per SEQ ID NO:1; and/or sequence section B) corresponds to positions 350 to 362, preferably positions 351 to 361, more preferably positions 352 to 360, even more preferably positions 353 to 359, most preferably positions 354 to 358, and in particular positions 355 to 357, as per SEQ ID NO:1; and/or sequence section C) corresponds to positions 578 to 590, preferably positions 579 to 589, more preferably positions 580 to 588, even more preferably positions 581 to 587, most preferably positions 582 to 586, and in particular positions 583 to 585, as per SEQ ID NO:1; and/or sequence section D) corresponds to positions 699 to 711, preferably positions 700 to 710, more preferably positions 701 to 709, even more preferably positions 702 to 708, most preferably positions 703 to 707, and in particular positions 704 to 706, as per SEQ ID NO:1; and/or sequence section E) corresponds to positions 782 to 794, preferably positions 783 to 793, more preferably positions 784 to 792, even more preferably positions 785 to 791, most preferably positions 786 to 790, and in particular positions 787 to 789, as per SEQ ID NO:1.

In a preferred embodiment, the cellobiose phosphorylase of the invention, when comprising an amino acid mutation in sequence section $A_6$) compared to SEQ ID NO:1, additionally comprises at least one further amino acid mutation but preferably not in sequence section $A_9$).

Preference is given to at least one amino acid mutation being selected from the group consisting of
Q161, Y164, R166, S169, I170, R188, D196, A220, K283;
F356;
A584;
L705; and
T788.

Particular preference is given to at least one amino acid mutation being selected from the group consisting of
Q161, S169, A220, K283,
L705, and
T788.

For said at least one amino acid mutation, the preferred substitutions in said positions are: Q161M, Q161A, Q161G, Q161I, Q161L, or Q161V; S169V, S169A, S169G, S169I, S169L, or S169M; A220L, A220G, A220I, A220L, A220M, or A220V; K283A, K283G, K283I, K283L, K283M, or K283V; L705I, L705N, L705C, L705Q, or L705S; T788V, T788A, T788G, T788I, T788L, or T788M; particularly preferably Q161M, S169V, A220L, K283A, L705I, and T788V, respectively.

Particular preference is given, where appropriate in addition to the at least one amino acid mutation specified above, to at least one further amino acid mutation being selected from the group consisting of
Y164, R166, I170, R188, D196, and
F356 and
optionally A512.

For said at least one further amino acid mutation, the preferred substitutions in said positions are: Y164F, or Y164W; R166K, R166H, R166M, R166A, R166G, R166I, R166L, or R166V; I170T, I170N, I170C, I170Q, or I170S; R188K, or R188H; D196N, D196C, D196Q, D196S, or D196I; particularly preferably Y164F, R166M, I170T, R188K, D196N, and F356I (and optionally A512V), respectively.

Preferably, the cellobiose phosphorylase of the invention comprises, compared to SEQ ID NO:1, at least two, three, four, five, six, seven, eight, or nine amino acid mutations which are in each case independently of one another defined as above.

In a preferred embodiment, the at least two, three, four, five, six, seven, eight, or nine amino acid mutations are located independently of one another in sequence section $A_1$), $A_2$), $A_3$), $A_4$), $A_5$), $A_7$), $A_8$), $A_9$) B), C), D) and/or E).
In a preferred embodiment, no amino acid mutations are located in sequence section $A_6$).

In a preferred embodiment, the at least two, three, four, or five amino acid mutations are located independently of one another in sequence sections $A_1$), $A_6$), $A_7$), $A_8$) and/or D), with preferably one amino acid mutation being located in sequence section $A_1$), one amino acid mutation being located in sequence section $A_6$), one amino acid mutation being located in sequence section $A_7$), one amino acid mutation being located in sequence section $A_8$), and/or one amino acid mutation being located in sequence section D).

In a preferred embodiment, at least two, three, four or five amino acid mutations are located independently of one another in sequence sections $A_1$), $A_8$), $A_9$), D) and/or E), with preferably one amino acid mutation being located in sequence section $A_1$), one amino acid mutation being located in sequence section $A_8$), one amino acid mutation being located in sequence section $A_9$), one amino acid mutation being located in sequence section D), and/or one amino acid mutation being located in sequence section E). In a preferred embodiment, however, no amino acid mutations are located in sequence section $A_6$). In another preferred embodiment, in addition, one or more further amino acid mutations are located independently of one another in sequence sections $A_6$), $A_7$), and/or F), with preferably one amino acid mutation being located in sequence section $A_6$), one amino acid mutation being located in sequence section $A_7$), and/or one amino acid mutation is located in sequence section F).

In a preferred embodiment, the at least two, three, four, five, six, seven, eight, or nine amino acid mutations are located independently of one another in sequence sections B), C), D) and/or E).

In a preferred embodiment, the at least two, three, four, five, six, seven, eight, or nine amino acid mutations are located in sequence section A), more preferably independently of one another in sequence sections $A_1$), $A_2$), $A_3$), $A_4$), $A_5$), $A_7$), $A_8$), and/or $A_9$). In a preferred embodiment, no amino acid mutation is located in sequence section $A_6$).

In preferred embodiments, the cellobiose phosphorylase of the invention comprises, compared to SEQ ID NO:1, at least two amino acid mutations "first amino acid mutation in sequence section"//"second amino acid mutation in sequence section" selected from the group consisting of: $A_1//A_2$, $A_1//A_2$, $A_1//A_3$, $A_1//A_4$, $A_1//A_5$, $A_1//A_6$, $A_1//A_7$, $A_1//A_8$, $A_1//A_9$, $A_1//B$, $A_1//C$, $A_1//D$, $A_1//E$; $A_2//A_2$, $A_2//A_3$, $A_2//A_4$, $A_2//A_5$, $A_2//A_6$, $A_2//A_7$, $A_2//A_8$, $A_2//A_9$, $A_2//B$, $A_2//C$, $A_2//D$, $A_2//E$; $A_3//A_3$, $A_3//A_4$, $A_3//A_5$, $A_3//A_6$, $A_3//A_7$, $A_3//A_8$, $A_3//A_9$, $A_3//B$, $A_3//C$, $A_3//D$, $A_3//E$; $A_4//A_4$, $A_4//A_5$, $A_4//A_6$, $A_4//A_7$, $A_4//A_8$, $A_4//A_9$, $A_4//B$, $A_4//C$, $A_4//D$, $A_4//E$; $A_5//A_5$, $A_5//A_6$, $A_5//A_7$, $A_5//A_8$, $A_5//A_9$, $A_5//B$, $A_5//C$, $A_5//D$, $A_5//E$; $A_6//A_6$, $A_6//A_7$, $A_6//A_8$, $A_6//A_9$, $A_6//B$, $A_6//C$, $A_6//D$, $A_6//E$; $A_7//A_7$, $A_7//A_8$, $A_7//A_9$, $A_7//B$, $A_7//C$, $A_7//D$, $A_7//E$; $A_8//A_8$, $A_8//A_9$, $A_8//B$, $A_8//C$, $A_8//D$, $A_8//E$; $A_9//A_9$, $A_9//B$, $A_9//C$, $A_9//D$, $A_9//E$; B//B, B//C, B//D, B//E; C//C, C//D, C//E; D//D, D//E; E//E. For example "$A_8//A_9$"; and here means that the first of the at least two amino acid mutations is located in sequence section $A_8$), and the second of the at least two amino acid mutations is located in sequence section $A_9$).

In preferred embodiments, the cellobiose phosphorylase of the invention comprises, compared to SEQ ID NO:1, at least two amino acid mutations, one of which is located in sequence section $A_1$), and the other one of which is located in any of the sequence sections selected from the group of sequence sections $A_2$), $A_3$), $A_4$), $A_8$), B), D) and E).

In preferred embodiments, the cellobiose phosphorylase of the invention comprises, compared to SEQ ID NO:1, at least two amino acid mutations, one of which is located in sequence section $A_1$), and the other one of which is located in any of the sequence sections selected from the group of sequence sections $A_2$), $A_3$), $A_4$), $A_8$), B) and D).

In preferred embodiments, the cellobiose phosophorylase of the invention comprises, compared to SEQ ID NO:1, at least two amino acid mutations, one of the which is located in sequence section $A_1$) and the other one of which is located in sequence section $A_1$).

In preferred embodiments, the cellobiose phosphorylase of the invention comprises, compared to SEQ ID NO:1, at least two amino acid mutations, one of which is located in sequence section $A_1$) and the other one of which is located in sequence section $A_2$).

In preferred embodiments, the cellobiose phosphorylase of the invention comprises, compared to SEQ ID NO:1, at least two amino acid mutations, one of which is located in sequence section $A_1$) and the other one of which is located in sequence section $A_3$).

In preferred embodiments, the cellobiose phosphorylase of the invention comprises, compared to SEQ ID NO:1, at least two amino acid mutations, one of which is located in sequence section $A_1$) and the other one of which is located in sequence section $A_4$).

In preferred embodiments, the cellobiose phosphorylase of the invention comprises, compared to SEQ ID NO:1, at least two amino acid mutations, one of which is located in sequence section $A_1$) and the other one of which is located in sequence section $A_8$).

In preferred embodiments, the cellobiose phosphorylase of the invention comprises, compared to SEQ ID NO:1, at least two amino acid mutations, one of which is located in sequence section $A_1$) and the other one of which is located in sequence section B).

In preferred embodiments, the cellobiose phosphorylase of the invention comprises, compared to SEQ ID NO:1, at least two amino acid mutations, one of which is located in sequence section $A_1$) and the other one of which is located in sequence section D); wherein the amino acid sequence of the cellobiose phosphorylase of the invention preferably has neither the L705Q amino acid mutation nor the L705V amino acid mutation.

In preferred embodiments, the cellobiose phosphorylase of the invention comprises, compared to SEQ ID NO:1, at least two amino acid mutations, one of which is located in sequence section $A_1$) and the other one of which is located in sequence section E); wherein the amino acid sequence of the cellobiose phosphorylase of the invention preferably has neither the T788E amino acid mutation nor the T788A amino acid mutation nor the T788V amino acid mutation.

In preferred embodiments, the cellobiose phosphorylase of the invention comprises, compared to SEQ ID NO:1, at least two amino acid mutations, one of which is located in sequence section $A_8$) and the other one of which is located in any of the sequence sections selected from the group of sequence sections $A_1$), $A_2$), $A_3$), $A_4$), B), D), and E).

In preferred embodiments, the cellobiose phosphorylase of the invention comprises, compared to SEQ ID NO:1, at least two amino acid mutations, one of which is located in sequence section $A_8$) and the other one of which is located in any of the sequence sections selected from the group of sequence sections $A_1$), $A_2$), $A_3$), $A_4$), B), and D).

In preferred embodiments, the cellobiose phosphorylase of the invention comprises, compared to SEQ ID NO:1, at least two amino acid mutations, one of which is located in sequence section $A_8$) and the other one of which is located in sequence section $A_1$).

In preferred embodiments, the cellobiose phosphorylase of the invention comprises, compared to SEQ ID NO:1, at least two amino acid mutations, one of which is located in sequence section $A_8$) and the other one of which is located in sequence section $A_2$).

In preferred embodiments, the cellobiose phosphorylase of the invention comprises, compared to SEQ ID NO:1, at least two amino acid mutations, one of which is located in sequence section $A_8$) and the other one of which is located in sequence section $A_3$).

In preferred embodiments, the cellobiose phosphorylase of the invention comprises, compared to SEQ ID NO:1, at least two amino acid mutations, one of which is located in sequence section $A_8$) and the other one of which is located in sequence section $A_4$).

In preferred embodiments, the cellobiose phosphorylase of the invention comprises, compared to SEQ ID NO:1, at least two amino acid mutations, one of which is located in sequence section $A_8$) and the other one of which is located in sequence section B).

In preferred embodiments, the cellobiose phosphorylase of the invention comprises, compared to SEQ ID NO:1, at least two amino acid mutations, one of which is located in sequence section $A_8$) and the other one of which is located in sequence section D); wherein the amino acid sequence of the cellobiose phosphorylase of the invention preferably has neither the L705Q amino acid mutation nor the L705V amino acid mutation.

In preferred embodiments, the cellobiose phosphorylase of the invention comprises, compared to SEQ ID NO:1, at least two amino acid mutations, one of which is located in sequence section $A_8$) and the other one of which is located in sequence section E); wherein the amino acid sequence of the cellobiose phosphorylase of the invention preferably has neither the T788E amino acid mutation nor the T788A amino acid mutation nor the T788V amino acid mutation.

In preferred embodiments, the cellobiose phosphorylase of the invention comprises, compared to SEQ ID NO:1, at least three amino acid mutations, one of which is located in sequence section $A_1$), one of which is located in sequence section $A_4$) and one of which is located in sequence section $A_8$).

In preferred embodiments, the cellobiose phosphorylase of the invention comprises, compared to SEQ ID NO:1, at least three amino acid mutations, one of which is located in sequence section $A_1$), one of which is located in sequence section $A_8$) and one of which is located in sequence section D), wherein the amino acid sequence of the cellobiose phosphorylase of the invention preferably has neither the L705Q amino acid mutation nor the L705V amino acid mutation.

In preferred embodiments, the cellobiose phosphorylase of the invention comprises, compared to SEQ ID NO:1, at least four amino acid mutations, one of which is located in sequence section $A_1$), one of which is located in sequence section $A_4$), one of which is located in sequence section $A_8$), and one of which is located in sequence section D), wherein the amino acid sequence of the cellobiose phosphorylase of the invention preferably has neither the L705Q amino acid mutation nor the L705V amino acid mutation.

In preferred embodiments, the cellobiose phosphorylase of the invention comprises, compared to SEQ ID NO:1, at least four amino acid mutations, one of which is located in sequence section $A_1$), one of which is located in sequence section $A_8$), one of which is located in sequence section $A_9$), and one of which is located in sequence section D), wherein the amino acid sequence of the cellobiose phosphorylase of the invention preferably has neither the K283H amino acid mutation nor the L705Q amino acid mutation nor the L705V amino acid mutation.

In preferred embodiments, the cellobiose phosphorylase of the invention comprises, compared to SEQ ID NO:1, at least five amino acid mutations, one of which is located in sequence section $A_1$), one of which is located in sequence section $A_4$), one of which is located in sequence section $A_8$), one of which is located in sequence section $A_9$) and one of which is located in sequence section D), wherein the amino acid sequence of the cellobiose phosphorylase of the invention preferably has neither the K283H amino acid mutation nor the L705Q amino acid mutation nor the L705V amino acid mutation.

In preferred embodiments, the cellobiose phosphorylase of the invention comprises, compared to SEQ ID NO:1, at least five amino acid mutations, one of which is located in sequence section $A_1$), one of which is located in sequence section $A_8$), one of which is located in sequence section $A_9$), one of which is located in sequence section D), and one of which is located in sequence section E), wherein the amino acid sequence of the cellobiose phosphorylase of the invention preferably has neither the K283H amino acid mutation nor the L705Q amino acid mutation nor the L705V amino acid mutation nor the T788E amino acid mutation nor the T788A amino acid mutation.

In preferred embodiments, the cellobiose phosphorylase of the invention comprises, compared to SEQ ID NO:1, at least six amino acid mutations, one of which is located in sequence section $A_1$), one of which is located in sequence section $A_4$), one of which is located in sequence section $A_8$), one of which is located in sequence section $A_9$), one of which is located in sequence section D), and one of which is located in sequence section E), wherein the amino acid sequence of the cellobiose phosphorylase of the invention preferably has neither the K283H amino acid mutation nor the L705Q amino acid mutation nor the L705V amino acid mutation nor the T788E amino acid mutation nor the T788A amino acid mutation.

In a preferred embodiment, the at least one amino acid mutation is selected from the group consisting of Q161M, Q161A, Q161G, Q161I, Q161V, Y164F, Y164W, R166K, R166H, R166M, R166A, R166G, R166I, R166L, R166V, S169V, S169A, S169G, S169I, S169L, S169M, I170T, I170N, I170C, I170Q, I170S, R188K, R188H, D196N, D196C, D196Q, D196S, D196T, A220L, A220G, A220I, A220L, A220M, A220V, K283A, K283G, K283I, K283L, K283M, K283V;

F356I, F356A, F356G, F356L, F356M, F356V;

A584E A584D;

L705I, L705N, L705C, L705Q, L705S;

T788V, T788A, T788G, T788I, T788L, and T788M.

In a preferred embodiment, the at least one amino acid mutation is selected from the group consisting of

Q161M, Y164F, R166K, R166M, S169V, I170T, R188K, D196N, A220L, K283A;

F356I;

A584E;

L705I; and

T788V.

In a preferred embodiment, the cellobiose phosphorylase of the invention comprises, compared to SEQ ID NO:1, at least one further amino acid mutation in sequence section F) which corresponds to positions 375 to 555 as per SEQ ID NO:1. Preference is given to said at least one further amino acid mutation being in position 512 (A512).

Where the cellobiose phosphorylase of the invention comprises the R188K amino acid mutation in comparison with SEQ ID NO:1, it preferably does not simultaneously also comprise the K283H amino acid mutation in comparison with SEQ ID NO:1, and vice versa.

Where the cellobiose phosphorylase of the invention comprises the T788V amino acid mutation in comparison with SEQ ID NO:1, it preferably does not simultaneously also comprise the K283H amino acid mutation in comparison with SEQ ID NO:1, and vice versa.

In a preferred embodiment, the cellobiose phosphorylase of the invention does not comprise any R188T amino acid mutation in comparison with SEQ ID NO:1.

In a particularly preferred embodiment, the cellobiose phosphorylase of the invention does not comprise any K283H amino acid mutation in comparison with SEQ ID NO:1.

In a preferred embodiment, the cellobiose phosphorylase of the invention does not comprise any A512T amino acid mutation and/or any A512P amino acid mutation and/or any A512S amino acid mutation in comparison with SEQ ID NO:1.

In a preferred embodiment, the cellobiose phosphorylase of the invention does not comprise any A584E amino acid mutation in comparison with SEQ ID NO:1.

In a preferred embodiment, the cellobiose phosphorylase of the invention does not comprise any L705Q amino acid mutation and/or any L705V amino acid mutation in comparison with SEQ ID NO:1.

In a preferred embodiment, the cellobiose phosphorylase of the invention does not comprise any T788E amino acid mutation and/or any T788A amino acid mutation in comparison with SEQ ID NO:1.

Particular preference is given to the cellobiose phosphorylase of the invention comprising an amino acid sequence selected from the group consisting of SEQ ID NO: 2, 3, 4, 5, 6, 7, 8, 9, 10, 11, 12, 13, 14, 15, 16, 17, 18, 19, 20, 21, 22, 23, 24, 25, 26, 27 and 28.

In a preferred embodiment, the cellobiose phosphorylase of the invention comprises an amino acid sequence which differs from SEQ ID NO:1 and which is at least 90%, at least 91%, at least 92%, at least 93%, at least 94%, at least 95%, at least 96%, at least 97%, at least 98%, or at least 99%, identical to the amino acid sequence set forth in SEQ ID NO:8. Preferably, said amino acid sequence has, compared to SEQ ID NO:1, one or more amino acid mutations in the following positions, preferably all of them: 161, 188, 196, 220 and 705. Preferably, said amino acid sequence has, compared to SEQ ID NO:1, one or more of the following amino acid mutations, preferably all of them: Q161M, R188K, D196N, A220L and L705I.

In a preferred embodiment, the cellobiose phosphorylase of the invention comprises an amino acid sequence which differs from SEQ ID NO:1 and which is at least 90%, at least 91%, at least 92%, at least 93%, at least 94%, at least 95%, at least 96%, at least 97%, at least 98%, or at least 99%, identical to the amino acid sequence set forth in SEQ ID NO:18. Preferably, said amino acid sequence has, compared to SEQ ID NO:1, one or more amino acid mutations in the following positions, preferably all of them: 161, 164, 188, 196, 220, 283, 512 and 705. Preferably, said amino acid sequence has, compared to SEQ ID NO:1, one or more of the following amino acid mutations, preferably all of them: Q161M, Y164F, R188K, D196N, A220L, K283A, A512V and L705I.

In a preferred embodiment, the cellobiose phosphorylase of the invention comprises an amino acid sequence which differs from SEQ ID NO:1 and which is at least 90%, at least 91%, at least 92%, at least 93%, at least 94%, at least 95%, at least 96%, at least 97%, at least 98%, or at least 99%, identical to the amino acid sequence set forth in SEQ ID NO:19. Preferably, said amino acid sequence has, compared to SEQ ID NO:1, one or more amino acid mutations in the following positions, preferably all of them: 161, 164, 188, 196, 220, 283, 512, 705 and 788. Preferably, said amino acid sequence has, compared to SEQ ID NO:1, one or more of the following amino acid mutations, preferably all of them: Q161M, Y164F, R188K, D196N, A220L, K283A, A512V, L705I and T788V.

In a preferred embodiment, the cellobiose phosphorylase of the invention comprises an amino acid sequence which differs from SEQ ID NO:1 and which is at least 90%, at least 91%, at least 92%, at least 93%, at least 94%, at least 95%, at least 96%, at least 97%, at least 98%, or at least 99%, identical to the amino acid sequence set forth in SEQ ID NO:20. Preferably, said amino acid sequence has, compared to SEQ ID NO:1, one or more amino acid mutations in the following positions, preferably all of them: 161, 166, 188, 196, 220, 283, 512, 705 and 788. Preferably, said amino acid sequence has, compared to SEQ ID NO:1, one or more of the following amino acid mutations, preferably all of them: Q161M, R166M, R188K, D196N, A220L, K283A, A512V, L705I and T788V.

In a preferred embodiment, the cellobiose phosphorylase of the invention comprises an amino acid sequence which differs from SEQ ID NO:1 and which is at least 90%, at least 91%, at least 92%, at least 93%, at least 94%, at least 95%, at least 96%, at least 97%, at least 98%, or at least 99%, identical to the amino acid sequence set forth in SEQ ID NO:21. Preferably, said amino acid sequence has, compared to SEQ ID NO:1, one or more amino acid mutations in the following positions, preferably all of them: 161, 169, 188, 196, 220, 283, 512, 705 and 788. Preferably, said amino acid sequence has, compared to SEQ ID NO:1, one or more of the following amino acid mutations, preferably all of them: Q161M, S169V, R188K, D196N, A220L, K283A, A512V, L705I and T788V.

In a preferred embodiment, the cellobiose phosphorylase of the invention comprises an amino acid sequence which differs from SEQ ID NO:1 and which is at least 90%, at least 91%, at least 92%, at least 93%, at least 94%, at least 95%, at least 96%, at least 97%, at least 98%, or at least 99%, identical to the amino acid sequence set forth in SEQ ID NO:25. Preferably, the amino acid sequence has, compared to SEQ ID NO:1, one or more amino acid mutations in positions 161, 169, 188, 196, 220, 283, 633, 705 and 788. Preferably, said amino acid sequence has, compared to SEQ ID NO:1, one or more of the amino acid mutations Q161M, S169V, R188K, D196N, A220L, K283A, M633I, L705I and L788V.

In a preferred embodiment, the cellobiose phosphorylase of the invention comprises an amino acid sequence which differs from SEQ ID NO:1 and which is at least 90%, at least 91%, at least 92%, at least 93%, at least 94%, at least 95%, at least 96%, at least 97%, at least 98%, or at least 99%, identical to the amino acid sequence set forth in SEQ ID NO:26. Preferably, the amino acid sequence has, compared to SEQ ID NO:1, one or more amino acid mutations in positions 161, 169, 196, 220, 283, 633, 705 and 788. Preferably, said amino acid sequence has, compared to SEQ ID NO:1, one or more of the amino acid mutations Q161M, S169V, D196N, A220L, K283A, M633I, L705I and L788V.

More specifically, the amino acid sequences set forth in SEQ ID NO:19 and SEQ ID NO:21, compared to the amino acid sequence set forth in SEQ ID NO:1, are distinguished with regard to the catalysis of cellobiose synthesis from glucose 1-phosphate and glucose by the following properties:

(i) increased specific activity for converting glucose and glucose 1-phosphate, in particular at higher substrate concentrations, with the activity with regard to the phosphorolytic reverse reaction being substantially retained; and/or (ii) increased space-time yield per amount of enzyme employed, in particular at elevated glucose concentration, due to improved reactant and product tolerances and lower reactant and product inhibitions, respectively.

The property under (i) means that an increased synthesis/phosphorolysis ratio is achieved compared to the amino acid sequence set forth in SEQ ID NO:1.

The property under (ii) means that an increased space-time yield per amount of enzyme employed is achieved compared to the amino acid sequence set forth in SEQ ID NO:1. The space-time yield is defined as the amount of product formed per volume and time at maximum substrate conversion.

Moreover, the amino acid sequences set forth in SEQ ID NO:8, SEQ ID NO:18 and SEQ ID NO:19 are distinguished by an improved thermal stability compared to the amino acid sequence set forth in SEQ ID NO:1.

The differences of these amino acid sequences of the invention from the *Cellulomonas uda* cellobiose phosphorylase (wild type, SEQ ID NO:1) are compared in the table below:

(ii) a higher space-time yield per amount of enzyme employed in the presence of equimolar amounts of glucose and glucose 1-phosphate of 250, and 500 mM; and/or (iii) an increased synthesis/phosphorolysis ratio which is increased preferably at least two-fold, more preferably at least four-fold, at least six-fold, at least eight-fold, at least ten-fold, at least 15-fold, at least 20-fold, or is increased at least 25-fold.

Surprisingly, the cellobiose phosphorylase of the invention was further found to possibly have advantages over the cellobiose phosphorylase set forth in SEQ ID NO:1 with regard to process stability, more specifically greater thermal stability, for example after incubation at 58° C. for 15 min.

A further aspect of the invention relates to the use of the cellobiose phosphorylase of the invention described above for the enzymatically catalyzed reaction of glucose 1-phosphate to give cellobiose and/or of glucose 1-phosphate with glucose to give cellobiose.

Any preferred embodiments described above in connection with the cellobiose phosphorylase of the invention correspondingly also apply to its use according to the invention and are therefore not repeated here.

| Sequence section | | | | | | | | | | | | | | | | | | |
|---|---|---|---|---|---|---|---|---|---|---|---|---|---|---|---|---|---|---|
| SEQ | Number of | | | | | A) | | | | | | B) | | C) | | D) | E) | F) |
| ID NO: | mutations | 161 | 164 | 166 | 169 | 170 | 188 | 196 | 220 | 283 | 317 | 356 | 473 | 554 | 584 | 633 | 705 | 788 | 512 |
| 1 | — | Gla | Tyr | Arg | Ser | Ile | Arg | Asp | Ala | Lys | Asp | Phe | Thr | Glu | Ala | Met | Leu | Thr | Ala |
| 2 | 1 | Met | Tyr | Arg | Ser | Ile | Arg | Asp | Ala | Lys | Asp | Phe | Thr | Glu | Ala | Met | Leu | Thr | Ala |
| 3 | 1 | Gln | Phe | Arg | Ser | Ile | Arg | Asp | Ala | Lys | Asp | Phe | Thr | Glu | Ala | Met | Leu | Thr | Ala |
| 4 | 1 | Gln | Tyr | Arg | Ser | Ile | Lys | Asp | Ala | Lys | Asp | Phe | Thr | Glu | Ala | Met | Leu | Thr | Ala |
| 5 | 1 | Gln | Tyr | Arg | Ser | Ile | Arg | Asn | Ala | Lys | Asp | Phe | Thr | Glu | Ala | Met | Leu | Thr | Ala |
| 6 | 1 | Gln | Tyr | Arg | Ser | Ile | Arg | Asp | Leu | Lys | Asp | Phe | Thr | Glu | Ala | Met | Leu | Thr | Ala |
| 7 | 1 | Gln | Tyr | Arg | Ser | Ile | Arg | Asp | Ala | Lys | Asp | Phe | Thr | Glu | Ala | Met | Thr | Thr | Ala |
| 8 | 5 | Met | Tyr | Arg | Ser | Ile | Lys | Asn | Leu | Lys | Asp | Phe | Thr | Glu | Ala | Met | Thr | Thr | Ala |
| 9 | 6 | Met | Tyr | Lys | Ser | Ile | Lys | Asn | Leu | Lys | Asp | Phe | Thr | Glu | Ala | Met | Thr | Thr | Ala |
| 10 | 6 | Met | Tyr | Met | Ser | Ile | Lys | Asn | Leu | Lys | Asp | Phe | Thr | Glu | Ala | Met | Thr | Thr | Ala |
| 11 | 6 | Met | Phe | Arg | Ser | Ile | Lys | Asn | Leu | Lys | Asp | Phe | Thr | Glu | Ala | Met | Thr | Thr | Ala |
| 12 | 6 | Met | Tyr | Arg | Val | Ile | Lys | Asn | Leu | Lys | Asp | Phe | Thr | Glu | Ala | Met | Thr | Thr | Ala |
| 13 | 6 | Met | Tyr | Arg | Ser | Ile | Lys | Asn | Leu | Ala | Asp | Phe | Thr | Glu | Ala | Met | Thr | Thr | Ala |
| 14 | 6 | Met | Tyr | Arg | Ser | Ile | Lys | Asn | Leu | Lys | Asp | Phe | Thr | Glu | Ala | Met | Thr | Val | Ala |
| 15 | 6 | Met | Tyr | Arg | Val | Ile | Lys | Asn | Leu | Lys | Asp | Phe | Thr | Glu | Glu | Met | Leu | Thr | Ala |
| 16 | 6 | Met | Tyr | Arg | Ser | Thr | Lys | Asn | Leu | Lys | Asp | Phe | Thr | Glu | Ala | Met | Thr | Thr | Ala |
| 17 | 7 | Met | Tyr | Arg | Ser | Ile | Lys | Asn | Leu | Lys | Asp | Ile | Thr | Glu | Ala | Met | Leu | Val | Val |
| 18 | 8 | Met | Phe | Arg | Ser | Ile | Lys | Asn | Leu | Ala | Asp | Phe | Thr | Glu | Ala | Met | Thr | Thr | Val |
| 19 | 9 | Met | Phe | Arg | Ser | Ile | Lys | Asn | Leu | Ala | Asp | Phe | Thr | Glu | Ala | Met | Thr | Val | Val |
| 20 | 9 | Met | Tyr | Met | Ser | Ile | Lys | Asn | Leu | Ala | Asp | Phe | Thr | Glu | Ala | Met | Thr | Val | Val |
| 21 | 9 | Met | Tyr | Arg | Val | Ile | Lys | Asn | Leu | Ala | Asp | Phe | Thr | Glu | Ala | Met | Thr | Val | Val |
| 22 | 10 | Met | Tyr | Arg | Val | Ile | Lys | Asn | Leu | Ala | Asp | Phe | Glu | Glu | Ala | Met | Thr | Val | Val |
| 23 | 9 | Met | Tyr | Arg | Val | Ile | Arg | Asn | Leu | Ala | Asn | Phe | Thr | Glu | Ala | Met | Thr | Val | Val |
| 24 | 9 | Met | Tyr | Arg | Val | Ile | Arg | Asn | Leu | Ala | Asp | Phe | Thr | Asn | Ala | Met | Thr | Val | Val |
| 25 | 9 | Met | Tyr | Arg | Val | Ile | Lys | Asn | Leu | Ala | Asp | Phe | Thr | Glu | Ala | Ile | Thr | Val | Ala |
| 26 | 8 | Met | Tyr | Arg | Val | Ile | Arg | Asn | Leu | Ala | Asp | Phe | Thr | Glu | Ala | Ile | Thr | Val | Ala |
| 27 | 11 | Met | Tyr | Arg | Val | Ile | Lys | Asn | Leu | Ala | Asn | Phe | Glu | Glu | Ala | Met | Thr | Val | Val |
| 28 | 10 | Met | Tyr | Arg | Val | Ile | Lys | Asn | Leu | Ala | Asn | Phe | Thr | Glu | Ala | Ile | Thr | Val | Ala |

Preferably, the cellobiose phosphorylase of the invention catalyzes reacting glucose 1-phosphate to give cellobiose and/or reacting glucose 1-phosphate with glucose to give cellobiose.

Surprisingly, the cellobiose phosphorylase of the invention was found to have advantages over the cellobiose phosphorylase set forth in SEQ ID NO:1 with regard to reacting glucose 1-phosphate with glucose to give cellobiose, in particular (i) increased synthesizing activity in the presence of equimolar amounts of glucose and glucose 1-phosphate of 250, 500, and 750 mM; and/or Another aspect of the invention relates to a method of preparing cellobiose, comprising reacting glucose 1-phosphate and, where appropriate, glucose under enzymatic catalysis by the cellobiose phosphorylase of the invention described above.

Any preferred embodiments described above in connection with the cellobiose phosphorylase of the invention or with its use according to the invention correspondingly also apply to the method of the invention and are therefore not repeated here.

Preference is given to the method of the invention comprising the steps of (a) synthesizing glucose 1-phosphate and fructose by reacting sucrose and phosphate under enzymatic catalysis by a sucrose phosphorylase;
(b) synthesizing cellobiose and phosphate by reacting said glucose 1-phosphate with glucose under enzymatic catalysis by said cellobiose phosphorylase.

The following examples illustrate the invention but should not be construed as limiting:

Definitions, Materials and Methods

Phosphorolysis Units (PU):

A phosphorylase unit (=PU) is defined as the amount of enzyme that forms 1 µmol of α-D-glucose 1-phosphate in the presence of 10 mM cellobiose and 75 mM potassium phosphate buffer pH 7, at 30° C. in one minute. Determination of phosphorylase activity (PU) was measured via detection of the α-D-glucose 1-phosphate formed in the cellobiose phosphorylase reaction using a coupled phosphoglucomutase and glucose-6-phosphate dehydrogenase reaction. Phosphoglucomutase reacts α-D-glucose 1-phosphate to give glucose 6-phosphate which, catalyzed by a glucose-6-phosphate dehydrogenase, reacts to give 6-phosphogluconate with formation of NADPH. NADPH formation may be quantified by the change in absorption at 340 nm. The formation of one mol of NADPH correlates with the formation of one mol of α-D-glucose 1-phosphate.

HPLC Measurement of Glucose and Cellobiose:

Glucose and cellobiose were detected by HPLC. The analytes were separated at 40° C. on a 250×4.6 Luna-NH2 5 µm 100 Å (Phenomenex), with a flow rate of 2 mL/min. The mobile phase used was an acetonitrile-water mixture in a 79/21 (v/v) ratio. Detection of the analytes was performed with the aid of an RID detector.

Preparation of a Cellobiose Phosphorylase-Containing Crude Cell Extract:

The cellobiose phosphorylases set forth in SEQ ID NO:1-28 were expressed on a recombinant plasmid in *E. coli* BL21(DE3). A shaker flask containing 20 mL of an *E. coli*-customary culturing medium such as, for example, LB or TB medium containing 50 µg/mL kanamycin was inoculated with an overnight culture to $OD_{600}$ 0.1, and incubated at 37° C. and 200 rpm to $OD_{600}$ 0.6-0.8. Then IPTG was added with $c_{final}$=0.1 mM IPTG and the culture was incubated at 30° C. and 200 rpm overnight. The culture was harvested by centrifugation and taken up in a lysis buffer consisting of 50 mM potassium phosphate buffer pH 7, 10 mM $MgCl_2$, 0.5 mg/mL lysozyme, and 20 U/mL of a nuclease enzyme such as benzonase, for example. The cells were lyzed using sonication. Insoluble components were removed by centrifugation, and the cellobiose phosphorylase-containing crude extract thus obtained was employed in the examples described below.

EXEMPLARY EMBODIMENTS

Example 1 (Phosphorolysis Activity)

Phosphorolysis activity of cellobiose phosphorylase-containing crude cell extracts of the enzyme set forth in SEQ ID NO:1, 8, 18, 19, 20, and 21 was determined and normalized to a cell density of $OD_{600}$=1. The results are shown in table 1. The phosphorolysis activity yields per cell of the variants set forth in SEQ ID NO:8, 18, 19, 20, and 21 were between 69% and 127% compared to SEQ ID NO:1.

TABLE 1

| SEQ ID NO: | $PU/OD_{600}$ = 1 |
|---|---|
| 1 | 1.12 |
| 8 | 0.96 |
| 18 | 1.35 |
| 19 | 1.42 |
| 20 | 0.77 |
| 21 | 0.90 |

Example 2 (Synthesis-to-Phosphorolysis Ratio, 250 mM Substrates)

50 µL of a cellobiose phosphorylase-containing crude extract of the enzyme set forth in SEQ ID NO:1, 8, 18, 19, 20, and 21 were placed in a 0.5 mL reaction vessel. To this, 150 µL of a substrate solution preheated to 30° C. and containing equimolarly 333.3 mM α-D-glucose 1-phosphate and D-glucose in 50 mM MES buffer pH 6.5 were added. α-D-glucose 1-phosphate may originate from the reaction of a sucrose phosphorylase with sucrose and phosphate or be employed as a pure substance. The mixtures were at 30° C. and 300 rpm for 30 min and inactivated by incubation at 98° C. for 10 min. The mixtures were centrifuged and the cellobiose content was determined by HPLC. One synthesis unit at 250 mM substrate (=SU (250 mM)) is the amount of enzyme forming at 30° C. in the presence of 250 mM α-D-glucose 1-phosphate and 250 mM D-glucose in 50 mM MES buffer pH 6.5, 1 µmol of cellobiose in one minute. The results are shown in table 2. The variants set forth in SEQ ID NO:18, 19, 20 and 21 exhibit a more than two-fold increase compared to the wild-type enzyme.

TABLE 2

| SEQ ID NO: | SU(250 mM)/PU | Factor over SEQ ID NO: 1 |
|---|---|---|
| 1 | 0.10 | 1.0 |
| 8 | 0.08 | 0.8 |
| 18 | 0.24 | 2.4 |
| 19 | 0.24 | 2.4 |
| 20 | 0.79 | 7.8 |
| 21 | 1.60 | 15.9 |

Example 3 (Synthesis-to-Phosphorolysis Ratio, 500 mM Substrates)

Example 2 was repeated using a substrate solution consisting of equimolarly 666.6 mM α-D-glucose 1-phosphate and D-glucose in 50 mM MES buffer pH 6.5. α-D-glucose 1-phosphate may originate from the reaction of a sucrose phosphorylase with sucrose and phosphate or be employed as a pure substance. The results are shown in table 3. One synthesis unit at 500 mM substrate (=SU (500 mM)) is the amount of enzyme forming at 30° C. in the presence of 500 mM α-D-glucose 1-phosphate and 500 mM D-glucose in 50 mM MES buffer pH 6.5, 1 µmol of cellobiose in one minute. Upon increasing the substrate concentration to 500 mM, all of the variants exhibit an even greater increase in comparison with the cellobiose phosphorylase set forth in SEQ ID NO:1. Improvement of the best variant achieves an increase by a factor of 28.

TABLE 3

| SEQ ID NO: | SU(500 mM)/PU | Factor over SEQ ID NO: 1 |
|---|---|---|
| 1 | 0.04 | 1.0 |
| 8 | 0.05 | 1.1 |
| 18 | 0.13 | 2.9 |
| 19 | 0.15 | 3.4 |
| 20 | 0.71 | 15.8 |
| 21 | 1.27 | 28.2 |

Example 4 (Synthesis-to-Phosphorolysis Ratio, 750 mM Substrates)

Example 2 was repeated using a substrate solution consisting of equimolarly 1000 mM α-D-glucose 1-phosphate and D-glucose in 50 mM MES buffer pH 6.5. α-D-glucose 1-phosphate may originate from the reaction of a sucrose phosphorylase with sucrose and phosphate or be employed as a pure substance. The results are shown in table 4. One synthesis unit at 750 mM substrate (=SU (750 mM)) is the amount of enzyme forming at 30° C. in the presence of 750 mM α-D-glucose 1-phosphate and 750 mM D-glucose in 50 mM MES buffer pH 6.5, 1 μmol of cellobiose in one minute. No cellobiose formation was observed with the cellobiose phosphorylase set forth in SEQ ID NO:1 and 8. In contrast, the variants set forth in SEQ ID NO:18, 19, 20, and 21 achieved significant cellobiose formation and thus an increase over cellobiose phosphorylase set forth in SEQ ID NO:1 by at least 2.5, 3.6, 17.5, and 29.6, respectively.

TABLE 4

| SEQ ID NO: | SU(750 mM)/PU | Factor over SEQ ID NO: 1 |
|---|---|---|
| 1 | below detection limit (<0.03 SU(750 mM)/PU) | — |
| 8 | below detection limit (<0.03 SU(750 mM)/PU) | — |
| 18 | 0.08 | >2.5 |
| 19 | 0.11 | >3.6 |
| 20 | 0.53 | >17.5 |
| 21 | 0.89 | >29.6 |

Example 5 (Thermal Stability)

50 μL of cellobiose phosphorylase-containing crude extract of the cellobiose phosphorylase set forth in SEQ ID NO:1, 8, 18, and 19 were transferred to a PCR microtiter plate and incubated in a gradient PCR cycler at temperatures between 50.2 and 62.5° C. for 15 min. Precipitated protein was removed by centrifugation, and the phosphorolysis activity of the supernatant was determined. Table 5 lists the residual activities obtained. The residual activity of the cellobiose phosphorylase set forth in SEQ ID NO:1 decreases to 2% after incubation at 58.1° C. The variants set forth in SEQ ID NO:8, 18 and 19, however, exhibited a markedly greater thermal stability and still have between 15.4 and 55.8% residual activity after incubation at 58.1° C.

TABLE 5

| Thermal treatment [° C.] | Residual activity [%] | | | |
|---|---|---|---|---|
| | SEQ ID NO: 1 | SEQ ID NO: 8 | SEQ ID NO: 18 | SEQ ID NO: 19 |
| Without thermal treatment | 100.0 | 100.0 | 100.0 | 100.0 |
| 50.2 | 82.4 | 101.9 | 98.0 | 89.5 |

TABLE 5-continued

| Thermal treatment [° C.] | Residual activity [%] | | | |
|---|---|---|---|---|
| | SEQ ID NO: 1 | SEQ ID NO: 8 | SEQ ID NO: 18 | SEQ ID NO: 19 |
| 50.8 | | 102.0 | | 85.7 |
| 50.9 | | | 92.5 | |
| 51 | 76.8 | | | |
| 51.9 | | 96.4 | 93.5 | 82.7 |
| 52.4 | 63.2 | | | |
| 53.3 | | 94.4 | 80.9 | 77.4 |
| 54.1 | 29.7 | | | |
| 54.8 | | 86.9 | 64.4 | 56.3 |
| 56.1 | 4.0 | | | |
| 56.5 | | 77.6 | 41.6 | 37.2 |
| 58.1 | 2.0 | 55.8 | 19.6 | 15.4 |
| 59.7 | | 21.3 | 1.1 | 0.6 |
| 60.2 | 0.9 | | | |
| 61 | | 6.0 | 0.0 | 0.0 |
| 61.9 | | 1.1 | 0.0 | 0.0 |
| 62.1 | 0.2 | | | |
| 62.5 | | 0.8 | 0.0 | 0.0 |

Example 6 (Long Term Activity at 30° C.)

To a 1.5 mL reaction vessel, 400 μL of cellobiose phosphorylase-containing crude extract of the cellobiose phosphorylases set forth in SEQ ID NO:8, 18, and 19 were transferred and incubated in an incubator at 30° C. The phosphorolysis activity was assayed over a period of 28 days. The results are shown in table 6. All variants still have an activity of >60% after incubation at 30° C. over 28 days.

TABLE 6

| Length of incubation at 30° C. [d] | Residual activity [%] | | |
|---|---|---|---|
| | SEQ ID NO: 8 | SEQ ID NO: 18 | SEQ ID NO: 19 |
| 0 | 100 | 100 | 100 |
| 6 | 94 | 93 | 98 |
| 13 | 85 | 86 | 89 |
| 19 | 72 | 78 | 78 |
| 28 | 64 | 75 | 67 |

Example 7 (Cellobiose Synthesis with 250 mM Substrates)

First, 300 μL of a cellobiose phosphorylase-containing crude extract of the variants set forth in SEQ ID NO:8, 19, 20, and 21 were introduced to a 2 mL reaction vessel. To this, 1.7 mL of a substrate solution preheated to 30° C. and containing equimolarly 294.1 mM α-D-glucose 1-phosphate and D-glucose in 50 mM MES buffer pH 6.5 were added. The mixtures were incubated at 30° C. and 300 rpm. Samples were taken over a period of 45.9 h until the maximum reaction rate was reached, and inactivated by incubation at 98° C. for 10 min. The mixtures were centrifuged and the cellobiose content was determined by HPLC. The variant set forth in SEQ ID NO:21 achieved the highest space-time yield per kPU employed of 19.6 mmol(cellobiose)/(h*L*kPU).

TABLE 7

| SEQ ID NO: | mmol(cellobiose)/(h*L*kPU) |
|---|---|
| 8 | 1.11 |
| 19 | 5.0 |

TABLE 7-continued

| SEQ ID NO: | mmol(cellobiose)/(h*L*kPU) |
|---|---|
| 20 | 20.0 |
| 21 | 19.6 |

Example 8 (Cellobiose Synthesis with 500 mM Substrates)

Example 7 was repeated with a substrate solution containing equimolarly 588.2 mM α-D-glucose 1-phosphate and D-glucose in 50 mM MES buffer pH 6.5. At this higher substrate concentration, the variant set forth in SEQ ID NO:21 achieved an even higher space-time yield per kPU employed of 25.3 mmol(cellobiose)/(h*L*kPU).

TABLE 8

| SEQ ID NO: | mmol(cellobiose)/(h*L*kPU) |
|---|---|
| 8 | 0.5 |
| 19 | 3.5 |
| 20 | 18.0 |
| 21 | 25.3 |

Example 9 (Cellobiose Synthesis from Sucrose and Glucose Employing a Sucrose Phosphorylase and the Cellobiose Phosphorylase of the Invention)

Sucrose (256 g) is dissolved with 48 g of sodium dihydrogen phosphate ($NaH_2PO_4$) and 57 g of disodium hydrogen phosphate ($Na_2HPO_4$) or 70 g of dipotassium hydrogen phosphate ($K_2HPO_4$) and 48 g of potassium dihydrogen phosphate ($KH_2PO_4$) in 1 L of water. The process solution is brought to a reaction temperature of 30° C. in a stirred tank reactor, and the reaction is started by adding 5 kU of *Bifidobacterium adolescentis* sucrose phosphorylase. The pH of the process solution is at 6.5 and is corrected, where necessary, with phosphoric acid or sodium or potassium hydroxide. The reaction is carried out for 20 h. The reaction solution is ultrafiltrated through a PES (polyether sulfone) membrane with a 10 kDa cutoff. To the permeate is added in a stirred tank reactor an amount of glucose as reaction partner which is equimolar to glucose 1-phosphate, and the permeate is heated to a reaction temperature of 30° C. (final concentration of glucose 1-phosphate in first product composition: approx. 0.5 M. The reaction is admixed by adding 3 kU (phosphorylase activity) of a *Cellulomonas uda* cellobiose phosphorylase (either of the mutant SEQ ID NO:8 or SEQ ID NO:19 or SEQ ID NO:21). The reaction is carried out at pH 6.5 over 24 h.

TABLE 9

| Enzyme SEQ ID NO: | Cellobiose [g/L] |
|---|---|
| 8 | 31 |
| 19 | 41 |
| 21 | 124 |

The invention claimed is:

1. A cellobiose phosphorylase comprising an amino acid sequence which has at least 94% sequence identity to the amino acid sequence set forth in SEQ ID NO: 21;
wherein the amino acid sequence has one or more amino acid mutations selected from the group consisting of Q161M, S169V, R188K, D196N, A220L, K283A, A512V, L705T and T788V compared to SEQ ID NO: 1; and
wherein the amino acid sequence does not comprise a K283H amino acid mutation.

2. The cellobiose phosphorylase according to claim 1, which has at least 95% sequence identity to the amino acid sequence set forth in SEQ ID NO: 21.

3. The cellobiose phosphorylase according to claim 2, which has at least 96% sequence identity to the amino acid sequence set forth in SEQ ID NO: 21.

4. The cellobiose phosphorylase according to claim 3, which has at least 97% sequence identity to the amino acid sequence set forth in SEQ ID NO: 21.

5. The cellobiose phosphorylase according to claim 4, which has at least 98% sequence identity to the amino acid sequence set forth in SEQ ID NO: 21.

6. The cellobiose phosphorylase according to claim 1, which catalyzes reacting glucose 1-phosphate to give cellobiose and/or reacting glucose 1-phosphate with glucose to give cellobiose.

7. The cellobiose phosphorylase according to claim 1, which, compared to the cellobiose phosphorylase set forth in SEQ ID NO: 1, (i) has increased synthesizing activity with regard to reacting glucose 1-phosphate with glucose to give cellobiose in the presence of equimolar amounts of glucose and glucose 1-phosphate of 250, 500, and 750 mM; and/or
(ii) has a higher space-time yield per the amount of enzyme employed with regard to reacting glucose 1-phosphate with glucose to give cellobiose in the presence of equimolar amounts of glucose and glucose 1-phosphate of 250, and 500 mM; and/or
(iii) has a higher thermal stability after incubation at 58° C. for 15 minutes.

8. A method of preparing cellobiose, comprising reacting glucose 1-phosphate and/or glucose under enzymatic catalysis by the cellobiose phosphorylase as claimed in claim 1.

9. The method as claimed in claim 8, comprising the steps of
a) synthesizing glucose 1-phosphate and fructose by reacting sucrose and phosphate under enzymatic catalysis by a sucrose phosphorylase; and
b) synthesizing cellobiose and phosphate by reacting said glucose 1-phosphate with glucose under enzymatic catalysis by said cellobiose phosphorylase.

10. A method for the synthesis of cellobiose comprising:
a) reacting under enzymatic catalysis the cellobiose phosphorylase of claim 1 with glucose 1-phosphate to give celloboise; and/or
b) reacting under enzymatic catalysis the cellobiose phosphorylase of claim 1 with glucose 1-phosphate and glucose to give cellobiose.

* * * * *

SEQUENCE LISTING

<160> NUMBER OF SEQ ID NOS: 28

<210> SEQ ID NO 1
<211> LENGTH: 822
<212> TYPE: PRT
<213> ORGANISM: Cellulomonas uda

<400> SEQUENCE: 1

```
Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
            20                  25                  30

Phe Phe Ser Leu Leu Ser His Gln Ala Gly Gly Tyr Ser Phe Tyr Arg
        35                  40                  45

Asp Ala Lys Met Arg Arg Leu Thr Arg Tyr Arg Tyr Asn Asn Ile Pro
    50                  55                  60

Ala Asp Ala Gly Gly Arg Tyr Leu Tyr Val Asn Asp Gly Gly Asp Val
65                  70                  75                  80

Trp Thr Pro Ser Trp Leu Pro Val Lys Ala Asp Leu Asp His Phe Glu
                85                  90                  95

Ala Arg His Gly Leu Gly Tyr Ser Thr Ile Thr Gly Glu Arg Asn Gly
            100                 105                 110

Val Arg Val Glu Thr Leu Phe Phe Val Pro Val Gly Glu Asn Ala Glu
        115                 120                 125

Val Gln Lys Val Thr Val Thr Asn Thr Ser Asp Ser Tyr Lys Ser Leu
    130                 135                 140

Thr Leu Phe Ser Phe Val Glu Phe Cys Leu Trp Asn Ala Gln Asp Asp
145                 150                 155                 160
```

```
Gln Thr Asn Tyr Gln Arg Asn Leu Ser Ile Gly Glu Val Glu Val Glu
            165                 170                 175
Gln Glu Ser Pro His Gly Ser Ala Ile Tyr His Arg Thr Glu Tyr Arg
        180                 185                 190
Glu Arg Arg Asp His Tyr Ala Val Phe Ala Val Asn Thr Gln Ala Glu
        195                 200                 205
Gly Phe Asp Thr Asp Arg Asp Thr Phe Val Gly Ala Tyr Asn Ser Leu
210                 215                 220
Gly Glu Ala Ala Val Pro Leu Lys Gly Glu Ser Ala Asn Ser Val Ala
225                 230                 235                 240
Ser Gly Trp Tyr Pro Ile Gly Ser His Ser Val Ala Val Ser Leu Ala
                245                 250                 255
Pro Gly Glu Ser Arg Glu Leu Val Tyr Val Leu Gly Tyr Val Glu Asn
            260                 265                 270
Pro Asp Glu Glu Lys Trp Ala Asp Ala Lys Gln Val Val Asn Lys
        275                 280                 285
Glu Arg Ala His Ala Leu Leu Ser Arg Phe Ala Thr Ser Glu Gln Thr
        290                 295                 300
Asp Ala Ala Phe Ala Ala Leu Lys Asp Tyr Trp Thr Asp Leu Leu Ser
305                 310                 315                 320
Thr Tyr Ser Val Ser Ser Asn Asp Glu Lys Leu Asp Arg Met Val Asn
                325                 330                 335
Ile Trp Asn Gln Tyr Gln Cys Met Val Thr Phe Asn Met Ser Arg Ser
            340                 345                 350
Ala Ser Phe Phe Glu Thr Gly Ile Gly Arg Gly Met Gly Phe Arg Asp
        355                 360                 365
Ser Asn Gln Asp Leu Leu Gly Phe Val His Leu Ile Pro Glu Arg Ala
        370                 375                 380
Arg Glu Arg Ile Ile Asp Ile Ala Ser Thr Gln Phe Ala Asp Gly Ser
385                 390                 395                 400
Ala Tyr His Gln Tyr Gln Pro Leu Thr Lys Arg Gly Asn Asn Asp Ile
                405                 410                 415
Gly Ser Gly Phe Asn Asp Asp Pro Leu Trp Leu Ile Ala Gly Thr Ala
            420                 425                 430
Ala Tyr Ile Lys Glu Thr Gly Asp Phe Ser Ile Leu Asp Glu Pro Val
        435                 440                 445
Pro Phe Asp Asn Glu Pro Gly Ser Glu Val Pro Leu Phe Glu His Leu
        450                 455                 460
Thr Arg Ser Phe Glu Phe Thr Val Thr His Arg Gly Pro His Gly Leu
465                 470                 475                 480
Pro Leu Ile Gly Arg Ala Asp Trp Asn Asp Cys Leu Asn Leu Asn Cys
                485                 490                 495
Phe Ser Thr Thr Pro Gly Glu Ser Phe Gln Thr Thr Glu Asn Gln Ala
            500                 505                 510
Gly Gly Val Ala Glu Ser Thr Phe Ile Ala Ala Gln Phe Val Leu Tyr
        515                 520                 525
Gly Glu Gln Tyr Ala Glu Leu Ala Ala Arg Gly Leu Ala Asp Val
        530                 535                 540
Ala Asp Arg Ala Arg Gly His Val Ala Glu Met Arg Asp Ala Leu Leu
545                 550                 555                 560
Thr Asp Gly Trp Asp Gly Ser Trp Phe Leu Arg Ala Tyr Asp Tyr Tyr
                565                 570                 575
Gly Asn Pro Ile Gly Thr Asp Ala His Asp Glu Gly Lys Ile Trp Ile
```

```
                580                 585                 590
Glu Pro Gln Gly Phe Ala Val Met Ala Gly Val Gly Val Gly Glu Gly
            595                 600                 605

Pro Gln Asp Thr Asp Ala Pro Ala Ile Lys Ala Leu Asp Ser Val Asn
        610                 615                 620

Glu Met Leu Ala Thr Asp His Gly Met Val Leu Gln Tyr Pro Ala Tyr
625                 630                 635                 640

Thr Thr Tyr Gln Val His Met Gly Glu Val Ser Thr Tyr Pro Pro Gly
                645                 650                 655

Tyr Lys Glu Asn Gly Gly Ile Phe Cys His Asn Asn Pro Trp Val Ile
            660                 665                 670

Ile Ala Glu Thr Val Val Gly Arg Gly Arg Ala Phe Asp Tyr Tyr
        675                 680                 685

Lys Arg Ile Thr Pro Ala Tyr Arg Glu Asp Ile Ser Asp Val His Arg
        690                 695                 700

Leu Glu Pro Tyr Val Tyr Ala Gln Met Ile Ala Gly Lys Glu Ala Val
705                 710                 715                 720

Arg His Gly Glu Ala Lys Asn Ser Trp Leu Thr Gly Thr Ala Ala Trp
                725                 730                 735

Asn Phe Val Thr Val Ser Gln Tyr Leu Leu Gly Val Arg Pro Glu Tyr
            740                 745                 750

Asp Gly Leu Val Val Asp Pro Gln Ile Gly Pro Asp Val Pro Ser Phe
        755                 760                 765

Thr Val Thr Arg Val Ala Arg Gly Ala Thr Tyr Glu Ile Thr Val Thr
        770                 775                 780

Asn Ser Gly Thr Asp Gly Ser Arg Gly Arg Leu Val Val Asp Gly Thr
785                 790                 795                 800

Pro Val Glu Gly Asn Leu Val Pro Tyr Ala Pro Ala Gly Ser Thr Val
                805                 810                 815

Arg Val Asp Val Thr Leu
            820

<210> SEQ ID NO 2
<211> LENGTH: 822
<212> TYPE: PRT
<213> ORGANISM: artificial
<220> FEATURE:
<223> OTHER INFORMATION: modified wildtye sequence

<400> SEQUENCE: 2

Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
            20                  25                  30

Phe Phe Ser Leu Leu Ser His Gln Ala Gly Gly Tyr Ser Phe Tyr Arg
        35                  40                  45

Asp Ala Lys Met Arg Arg Leu Thr Arg Tyr Arg Tyr Asn Asn Ile Pro
    50                  55                  60

Ala Asp Ala Gly Gly Arg Tyr Leu Tyr Val Asn Asp Gly Gly Asp Val
65                  70                  75                  80

Trp Thr Pro Ser Trp Leu Pro Val Lys Ala Asp Leu Asp His Phe Glu
                85                  90                  95

Ala Arg His Gly Leu Gly Tyr Ser Thr Ile Thr Gly Glu Arg Asn Gly
            100                 105                 110

Val Arg Val Glu Thr Leu Phe Phe Val Pro Val Gly Glu Asn Ala Glu
```

```
            115                 120                 125
Val Gln Lys Val Thr Val Thr Asn Thr Ser Asp Ser Tyr Lys Ser Leu
        130                 135                 140
Thr Leu Phe Ser Phe Val Glu Phe Cys Leu Trp Asn Ala Gln Asp Asp
145                 150                 155                 160
Met Thr Asn Tyr Gln Arg Asn Leu Ser Ile Gly Val Glu Val Glu
                165                 170                 175
Gln Glu Ser Pro His Gly Ser Ala Ile Tyr His Arg Thr Glu Tyr Arg
                180                 185                 190
Glu Arg Arg Asp His Tyr Ala Val Phe Ala Val Asn Thr Gln Ala Glu
                195                 200                 205
Gly Phe Asp Thr Asp Arg Asp Thr Phe Val Gly Ala Tyr Asn Ser Leu
        210                 215                 220
Gly Glu Ala Ala Val Pro Leu Lys Gly Glu Ser Ala Asn Ser Val Ala
225                 230                 235                 240
Ser Gly Trp Tyr Pro Ile Gly Ser His Ser Val Ala Val Ser Leu Ala
                245                 250                 255
Pro Gly Glu Ser Arg Glu Leu Val Tyr Val Leu Gly Tyr Val Glu Asn
                260                 265                 270
Pro Asp Glu Glu Lys Trp Ala Asp Ala Lys Gln Val Val Asn Lys
                275                 280                 285
Glu Arg Ala His Ala Leu Leu Ser Arg Phe Ala Thr Ser Glu Gln Thr
        290                 295                 300
Asp Ala Ala Phe Ala Ala Leu Lys Asp Tyr Trp Thr Asp Leu Leu Ser
305                 310                 315                 320
Thr Tyr Ser Val Ser Ser Asn Asp Glu Lys Leu Asp Arg Met Val Asn
                325                 330                 335
Ile Trp Asn Gln Tyr Gln Cys Met Val Thr Phe Asn Met Ser Arg Ser
                340                 345                 350
Ala Ser Phe Phe Glu Thr Gly Ile Gly Arg Gly Met Gly Phe Arg Asp
                355                 360                 365
Ser Asn Gln Asp Leu Leu Gly Phe Val His Leu Ile Pro Glu Arg Ala
        370                 375                 380
Arg Glu Arg Ile Ile Asp Ile Ala Ser Thr Gln Phe Ala Asp Gly Ser
385                 390                 395                 400
Ala Tyr His Gln Tyr Gln Pro Leu Thr Lys Arg Gly Asn Asn Asp Ile
                405                 410                 415
Gly Ser Gly Phe Asn Asp Asp Pro Leu Trp Leu Ile Ala Gly Thr Ala
                420                 425                 430
Ala Tyr Ile Lys Glu Thr Gly Asp Phe Ser Ile Leu Asp Glu Pro Val
        435                 440                 445
Pro Phe Asp Asn Glu Pro Gly Ser Glu Val Pro Leu Phe Glu His Leu
        450                 455                 460
Thr Arg Ser Phe Glu Phe Thr Val Thr His Arg Gly Pro His Gly Leu
465                 470                 475                 480
Pro Leu Ile Gly Arg Ala Asp Trp Asn Asp Cys Leu Asn Leu Asn Cys
                485                 490                 495
Phe Ser Thr Thr Pro Gly Glu Ser Phe Gln Thr Thr Glu Asn Gln Ala
                500                 505                 510
Gly Gly Val Ala Glu Ser Thr Phe Ile Ala Ala Gln Phe Val Leu Tyr
                515                 520                 525
Gly Glu Gln Tyr Ala Glu Leu Ala Ala Arg Arg Gly Leu Ala Asp Val
        530                 535                 540
```

```
Ala Asp Arg Ala Arg Gly His Val Ala Glu Met Arg Asp Ala Leu Leu
545                 550                 555                 560

Thr Asp Gly Trp Asp Gly Ser Trp Phe Leu Arg Ala Tyr Asp Tyr Tyr
                565                 570                 575

Gly Asn Pro Ile Gly Thr Asp His Asp Glu Gly Lys Ile Trp Ile
                580                 585                 590

Glu Pro Gln Gly Phe Ala Val Met Ala Gly Val Gly Val Gly Glu Gly
                595                 600                 605

Pro Gln Asp Thr Asp Ala Pro Ala Ile Lys Ala Leu Asp Ser Val Asn
            610                 615                 620

Glu Met Leu Ala Thr Asp His Gly Met Val Leu Gln Tyr Pro Ala Tyr
625                 630                 635                 640

Thr Thr Tyr Gln Val His Met Gly Glu Val Ser Thr Tyr Pro Pro Gly
                645                 650                 655

Tyr Lys Glu Asn Gly Gly Ile Phe Cys His Asn Asn Pro Trp Val Ile
                660                 665                 670

Ile Ala Glu Thr Val Val Gly Arg Gly Arg Ala Phe Asp Tyr Tyr
                675                 680                 685

Lys Arg Ile Thr Pro Ala Tyr Arg Glu Asp Ile Ser Asp Val His Arg
690                 695                 700

Leu Glu Pro Tyr Val Tyr Ala Gln Met Ile Ala Gly Lys Glu Ala Val
705                 710                 715                 720

Arg His Gly Glu Ala Lys Asn Ser Trp Leu Thr Gly Thr Ala Ala Trp
                725                 730                 735

Asn Phe Val Thr Val Ser Gln Tyr Leu Leu Gly Val Arg Pro Glu Tyr
                740                 745                 750

Asp Gly Leu Val Val Asp Pro Gln Ile Gly Pro Asp Val Pro Ser Phe
                755                 760                 765

Thr Val Thr Arg Val Ala Arg Gly Ala Thr Tyr Glu Ile Thr Val Thr
                770                 775                 780

Asn Ser Gly Thr Asp Gly Ser Arg Gly Arg Leu Val Val Asp Gly Thr
785                 790                 795                 800

Pro Val Glu Gly Asn Leu Val Pro Tyr Ala Pro Ala Gly Ser Thr Val
                805                 810                 815

Arg Val Asp Val Thr Leu
                820

<210> SEQ ID NO 3
<211> LENGTH: 822
<212> TYPE: PRT
<213> ORGANISM: artificial
<220> FEATURE:
<223> OTHER INFORMATION: modified wildtye sequence

<400> SEQUENCE: 3

Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
                20                  25                  30

Phe Phe Ser Leu Leu Ser His Gln Ala Gly Gly Tyr Ser Phe Tyr Arg
            35                  40                  45

Asp Ala Lys Met Arg Arg Leu Thr Arg Tyr Tyr Asn Asn Ile Pro
        50                  55                  60

Ala Asp Ala Gly Gly Arg Tyr Leu Tyr Val Asn Asp Gly Gly Asp Val
65                  70                  75                  80
```

```
Trp Thr Pro Ser Trp Leu Pro Val Lys Ala Asp Leu Asp His Phe Glu
             85                  90                  95

Ala Arg His Gly Leu Gly Tyr Ser Thr Ile Thr Gly Glu Arg Asn Gly
            100                 105                 110

Val Arg Val Glu Thr Leu Phe Phe Val Pro Val Gly Asn Ala Glu
        115                 120                 125

Val Gln Lys Val Thr Val Thr Asn Thr Ser Asp Ser Tyr Lys Ser Leu
    130                 135                 140

Thr Leu Phe Ser Phe Val Glu Phe Cys Leu Trp Asn Ala Gln Asp Asp
145                 150                 155                 160

Gln Thr Asn Phe Gln Arg Asn Leu Ser Ile Gly Glu Val Glu Val Glu
                165                 170                 175

Gln Glu Ser Pro His Gly Ser Ala Ile Tyr His Arg Thr Glu Tyr Arg
            180                 185                 190

Glu Arg Arg Asp His Tyr Ala Val Phe Ala Val Asn Thr Gln Ala Glu
        195                 200                 205

Gly Phe Asp Thr Asp Arg Asp Thr Phe Val Gly Ala Tyr Asn Ser Leu
210                 215                 220

Gly Glu Ala Ala Val Pro Leu Lys Gly Glu Ser Ala Asn Ser Val Ala
225                 230                 235                 240

Ser Gly Trp Tyr Pro Ile Gly Ser His Ser Val Ala Val Ser Leu Ala
                245                 250                 255

Pro Gly Glu Ser Arg Glu Leu Val Tyr Val Leu Gly Tyr Val Glu Asn
            260                 265                 270

Pro Asp Glu Glu Lys Trp Ala Asp Ala Lys Gln Val Val Asn Lys
        275                 280                 285

Glu Arg Ala His Ala Leu Leu Ser Arg Phe Ala Thr Ser Glu Gln Thr
290                 295                 300

Asp Ala Ala Phe Ala Ala Leu Lys Asp Tyr Trp Thr Asp Leu Leu Ser
305                 310                 315                 320

Thr Tyr Ser Val Ser Ser Asn Asp Glu Lys Leu Asp Arg Met Val Asn
                325                 330                 335

Ile Trp Asn Gln Tyr Gln Cys Met Val Thr Phe Asn Met Ser Arg Ser
            340                 345                 350

Ala Ser Phe Phe Glu Thr Gly Ile Gly Arg Gly Met Gly Phe Arg Asp
        355                 360                 365

Ser Asn Gln Asp Leu Leu Gly Phe Val His Leu Ile Pro Glu Arg Ala
    370                 375                 380

Arg Glu Arg Ile Ile Asp Ile Ala Ser Thr Gln Phe Ala Asp Gly Ser
385                 390                 395                 400

Ala Tyr His Gln Tyr Gln Pro Leu Thr Lys Arg Gly Asn Asn Asp Ile
                405                 410                 415

Gly Ser Gly Phe Asn Asp Asp Pro Leu Trp Leu Ile Ala Gly Thr Ala
            420                 425                 430

Ala Tyr Ile Lys Glu Thr Gly Asp Phe Ser Ile Leu Asp Glu Pro Val
        435                 440                 445

Pro Phe Asp Asn Glu Pro Gly Ser Glu Val Pro Leu Phe Glu His Leu
    450                 455                 460

Thr Arg Ser Phe Glu Phe Thr Val Thr His Arg Gly Pro His Gly Leu
465                 470                 475                 480

Pro Leu Ile Gly Arg Ala Asp Trp Asn Asp Cys Leu Asn Leu Asn Cys
                485                 490                 495
```

```
Phe Ser Thr Thr Pro Gly Glu Ser Phe Gln Thr Glu Asn Gln Ala
                500                 505                 510
Gly Gly Val Ala Glu Ser Thr Phe Ile Ala Ala Gln Phe Val Leu Tyr
        515                 520                 525
Gly Glu Gln Tyr Ala Glu Leu Ala Ala Arg Arg Gly Leu Ala Asp Val
        530                 535                 540
Ala Asp Arg Ala Arg Gly His Val Ala Glu Met Arg Asp Ala Leu Leu
545                 550                 555                 560
Thr Asp Gly Trp Asp Gly Ser Trp Phe Leu Arg Ala Tyr Asp Tyr Tyr
                565                 570                 575
Gly Asn Pro Ile Gly Thr Asp Ala His Asp Glu Gly Lys Ile Trp Ile
                580                 585                 590
Glu Pro Gln Gly Phe Ala Val Met Ala Gly Val Gly Val Gly Glu Gly
                595                 600                 605
Pro Gln Asp Thr Asp Ala Pro Ala Ile Lys Ala Leu Asp Ser Val Asn
                610                 615                 620
Glu Met Leu Ala Thr Asp His Gly Met Val Leu Gln Tyr Pro Ala Tyr
625                 630                 635                 640
Thr Thr Tyr Gln Val His Met Gly Glu Val Ser Thr Tyr Pro Pro Gly
                645                 650                 655
Tyr Lys Glu Asn Gly Gly Ile Phe Cys His Asn Asn Pro Trp Val Ile
                660                 665                 670
Ile Ala Glu Thr Val Val Gly Arg Gly Arg Ala Phe Asp Tyr Tyr
                675                 680                 685
Lys Arg Ile Thr Pro Ala Tyr Arg Glu Asp Ile Ser Asp Val His Arg
                690                 695                 700
Leu Glu Pro Tyr Val Tyr Ala Gln Met Ile Ala Gly Lys Glu Ala Val
705                 710                 715                 720
Arg His Gly Glu Ala Lys Asn Ser Trp Leu Thr Gly Thr Ala Ala Trp
                725                 730                 735
Asn Phe Val Thr Val Ser Gln Tyr Leu Leu Gly Val Arg Pro Glu Tyr
                740                 745                 750
Asp Gly Leu Val Val Asp Pro Gln Ile Gly Pro Asp Val Pro Ser Phe
                755                 760                 765
Thr Val Thr Arg Val Ala Arg Gly Ala Thr Tyr Glu Ile Thr Val Thr
770                 775                 780
Asn Ser Gly Thr Asp Gly Ser Arg Gly Arg Leu Val Val Asp Gly Thr
785                 790                 795                 800
Pro Val Glu Gly Asn Leu Val Pro Tyr Ala Pro Ala Gly Ser Thr Val
                805                 810                 815
Arg Val Asp Val Thr Leu
                820

<210> SEQ ID NO 4
<211> LENGTH: 822
<212> TYPE: PRT
<213> ORGANISM: artificial
<220> FEATURE:
<223> OTHER INFORMATION: modified wildtye sequence

<400> SEQUENCE: 4

Met Arg Tyr Gly His Phe Asp Asp Glu Ala Arg Glu Tyr Val Ile Thr
1               5                   10                  15
Thr Pro His Thr Pro Tyr Pro Trp Ile Asn Tyr Leu Gly Ser Glu Gln
                20                  25                  30
```

```
Phe Phe Ser Leu Leu Ser His Gln Ala Gly Gly Tyr Ser Phe Tyr Arg
         35                  40                  45

Asp Ala Lys Met Arg Arg Leu Thr Arg Tyr Arg Tyr Asn Asn Ile Pro
 50                  55                  60

Ala Asp Ala Gly Gly Arg Tyr Leu Tyr Val Asn Asp Gly Gly Asp Val
 65                  70                  75                  80

Trp Thr Pro Ser Trp Leu Pro Val Lys Ala Asp Leu Asp His Phe Glu
                 85                  90                  95

Ala Arg His Gly Leu Gly Tyr Ser Thr Ile Thr Gly Glu Arg Asn Gly
                100                 105                 110

Val Arg Val Glu Thr Leu Phe Phe Val Pro Val Gly Glu Asn Ala Glu
            115                 120                 125

Val Gln Lys Val Thr Val Thr Asn Thr Ser Asp Ser Tyr Lys Ser Leu
130                 135                 140

Thr Leu Phe Ser Phe Val Glu Phe Cys Leu Trp Asn Ala Gln Asp Asp
145                 150                 155                 160

Gln Thr Asn Tyr Gln Arg Asn Leu Ser Ile Gly Glu Val Glu Val Glu
                165                 170                 175

Gln Glu Ser Pro His Gly Ser Ala Ile Tyr His Lys Thr Glu Tyr Arg
            180                 185                 190

Glu Arg Arg Asp His Tyr Ala Val Phe Ala Val Asn Thr Gln Ala Glu
        195                 200                 205

Gly Phe Asp Thr Asp Arg Asp Thr Phe Val Gly Ala Tyr Asn Ser Leu
    210                 215                 220

Gly Glu Ala Ala Val Pro Leu Lys Gly Glu Ser Ala Asn Ser Val Ala
225                 230                 235                 240

Ser Gly Trp Tyr Pro Ile Gly Ser His Ser Val Ala Val Ser Leu Ala
                245                 250                 255

Pro Gly Glu Ser Arg Glu Leu Val Tyr Val Leu Gly Tyr Val Glu Asn
            260                 265                 270

Pro Asp Glu Glu Lys Trp Ala Asp Ala Lys Gln Val Val Asn Lys
        275                 280                 285

Glu Arg Ala His Ala Leu Leu Ser Arg Phe Ala Thr Ser Glu Gln Thr
    290                 295                 300

Asp Ala Ala Phe Ala Ala Leu Lys Asp Tyr Trp Thr Asp Leu Leu Ser
305                 310                 315                 320

Thr Tyr Ser Val Ser Ser Asn Asp Glu Lys Leu Asp Arg Met Val Asn
                325                 330                 335

Ile Trp Asn Gln Tyr Gln Cys Met Val Thr Phe Asn Met Ser Arg Ser
            340                 345                 350

Ala Ser Phe Phe Glu Thr Gly Ile Gly Arg Gly Met Gly Phe Arg Asp
        355                 360                 365

Ser Asn Gln Asp Leu Leu Gly Phe Val His Leu Ile Pro Glu Arg Ala
    370                 375                 380

Arg Glu Arg Ile Ile Asp Ile Ala Ser Thr Gln Phe Ala Asp Gly Ser
385                 390                 395                 400

Ala Tyr His Gln Tyr Gln Pro Leu Thr Lys Arg Gly Asn Asn Asp Ile
                405                 410                 415

Gly Ser Gly Phe Asn Asp Asp Pro Leu Trp Leu Ile Ala Gly Thr Ala
            420                 425                 430

Ala Tyr Ile Lys Glu Thr Gly Asp Phe Ser Ile Leu Asp Glu Pro Val
        435                 440                 445

Pro Phe Asp Asn Glu Pro Gly Ser Glu Val Pro Leu Phe Glu His Leu
```

```
                450             455             460
Thr Arg Ser Phe Glu Phe Thr Val Thr His Arg Gly Pro His Gly Leu
465                 470                 475                 480

Pro Leu Ile Gly Arg Ala Asp Trp Asn Asp Cys Leu Asn Leu Asn Cys
                485                 490                 495

Phe Ser Thr Thr Pro Gly Glu Ser Phe Gln Thr Thr Glu Asn Gln Ala
                500                 505                 510

Gly Gly Val Ala Glu Ser Thr Phe Ile Ala Ala Gln Phe Val Leu Tyr
                515                 520                 525

Gly Glu Gln Tyr Ala Glu Leu Ala Ala Arg Arg Gly Leu Ala Asp Val
                530                 535                 540

Ala Asp Arg Ala Arg Gly His Val Ala Glu Met Arg Asp Ala Leu Leu
545                 550                 555                 560

Thr Asp Gly Trp Asp Gly Ser Trp Phe Leu Arg Ala Tyr Asp Tyr Tyr
                565                 570                 575

Gly Asn Pro Ile Gly Thr Asp Ala His Asp Glu Gly Lys Ile Trp Ile
                580                 585                 590

Glu Pro Gln Gly Phe Ala Val Met Ala Gly Val Gly Val Gly Glu Gly
                595                 600                 605

Pro Gln Asp Thr Asp Ala Pro Ala Ile Lys Ala Leu Asp Ser Val Asn
                610                 615                 620

Glu Met Leu Ala Thr Asp His Gly Met Val Leu Gln Tyr Pro Ala Tyr
625                 630                 635                 640

Thr Thr Tyr Gln Val His Met Gly Glu Val Ser Thr Tyr Pro Pro Gly
                645                 650                 655

Tyr Lys Glu Asn Gly Gly Ile Phe Cys His Asn Asn Pro Trp Val Ile
                660                 665                 670

Ile Ala Glu Thr Val Val Gly Arg Gly Arg Ala Phe Asp Tyr Tyr
                675                 680                 685

Lys Arg Ile Thr Pro Ala Tyr Arg Glu Asp Ile Ser Asp Val His Arg
690                 695                 700

Leu Glu Pro Tyr Val Tyr Ala Gln Met Ile Ala Gly Lys Glu Ala Val
705                 710                 715                 720

Arg His Gly Glu Ala Lys Asn Ser Trp Leu Thr Gly Thr Ala Ala Trp
                725                 730                 735

Asn Phe Val Thr Val Ser Gln Tyr Leu Leu Gly Val Arg Pro Glu Tyr
                740                 745                 750

Asp Gly Leu Val Val Asp Pro Gln Ile Gly Pro Asp Val Pro Ser Phe
                755                 760                 765

Thr Val Thr Arg Val Ala Arg Gly Ala Thr Tyr Glu Ile Thr Val Thr
                770                 775                 780

Asn Ser Gly Thr Asp Gly Ser Arg Gly Arg Leu Val Val Asp Gly Thr
785                 790                 795                 800

Pro Val Glu Gly Asn Leu Val Pro Tyr Ala Pro Ala Gly Ser Thr Val
                805                 810                 815

Arg Val Asp Val Thr Leu
                820
```

<210> SEQ ID NO 5
<211> LENGTH: 822
<212> TYPE: PRT
<213> ORGANISM: artificial
<220> FEATURE:
<223> OTHER INFORMATION: modified wildtye sequence

```
<400> SEQUENCE: 5

Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
            20                  25                  30

Phe Phe Ser Leu Leu Ser His Gln Ala Gly Gly Tyr Ser Phe Tyr Arg
        35                  40                  45

Asp Ala Lys Met Arg Arg Leu Thr Arg Tyr Arg Tyr Asn Asn Ile Pro
    50                  55                  60

Ala Asp Ala Gly Gly Arg Tyr Leu Tyr Val Asn Asp Gly Gly Asp Val
65                  70                  75                  80

Trp Thr Pro Ser Trp Leu Pro Val Lys Ala Asp Leu Asp His Phe Glu
            85                  90                  95

Ala Arg His Gly Leu Gly Tyr Ser Thr Ile Thr Gly Glu Arg Asn Gly
        100                 105                 110

Val Arg Val Glu Thr Leu Phe Phe Val Pro Val Gly Glu Asn Ala Glu
    115                 120                 125

Val Gln Lys Val Thr Val Thr Asn Thr Ser Asp Ser Tyr Lys Ser Leu
130                 135                 140

Thr Leu Phe Ser Phe Val Glu Phe Cys Leu Trp Asn Ala Gln Asp Asp
145                 150                 155                 160

Gln Thr Asn Tyr Gln Arg Asn Leu Ser Ile Gly Glu Val Glu Val Glu
            165                 170                 175

Gln Glu Ser Pro His Gly Ser Ala Ile Tyr His Arg Thr Glu Tyr Arg
        180                 185                 190

Glu Arg Arg Asn His Tyr Ala Val Phe Ala Val Asn Thr Gln Ala Glu
    195                 200                 205

Gly Phe Asp Thr Asp Arg Asp Thr Phe Val Gly Ala Tyr Asn Ser Leu
210                 215                 220

Gly Glu Ala Ala Val Pro Leu Lys Gly Glu Ser Ala Asn Ser Val Ala
225                 230                 235                 240

Ser Gly Trp Tyr Pro Ile Gly Ser His Ser Val Ala Val Ser Leu Ala
            245                 250                 255

Pro Gly Glu Ser Arg Glu Leu Val Tyr Val Leu Gly Tyr Val Glu Asn
        260                 265                 270

Pro Asp Glu Glu Lys Trp Ala Asp Ala Lys Gln Val Val Asn Lys
    275                 280                 285

Glu Arg Ala His Ala Leu Leu Ser Arg Phe Ala Thr Ser Glu Gln Thr
290                 295                 300

Asp Ala Ala Phe Ala Ala Leu Lys Asp Tyr Trp Thr Asp Leu Leu Ser
305                 310                 315                 320

Thr Tyr Ser Val Ser Ser Asn Asp Glu Lys Leu Asp Arg Met Val Asn
            325                 330                 335

Ile Trp Asn Gln Tyr Gln Cys Met Val Thr Phe Asn Met Ser Arg Ser
        340                 345                 350

Ala Ser Phe Phe Glu Thr Gly Ile Gly Arg Gly Met Gly Phe Arg Asp
    355                 360                 365

Ser Asn Gln Asp Leu Leu Gly Phe Val His Leu Ile Pro Glu Arg Ala
370                 375                 380

Arg Glu Arg Ile Ile Asp Ile Ala Ser Thr Gln Phe Ala Asp Gly Ser
385                 390                 395                 400

Ala Tyr His Gln Tyr Gln Pro Leu Thr Lys Arg Gly Asn Asn Asp Ile
            405                 410                 415
```

```
Gly Ser Gly Phe Asn Asp Asp Pro Leu Trp Leu Ile Ala Gly Thr Ala
            420                 425                 430
Ala Tyr Ile Lys Glu Thr Gly Asp Phe Ser Ile Leu Asp Glu Pro Val
        435                 440                 445
Pro Phe Asp Asn Glu Pro Gly Ser Glu Val Pro Leu Phe Glu His Leu
    450                 455                 460
Thr Arg Ser Phe Glu Phe Thr Val Thr His Arg Gly Pro His Gly Leu
465                 470                 475                 480
Pro Leu Ile Gly Arg Ala Asp Trp Asn Asp Cys Leu Asn Leu Asn Cys
                485                 490                 495
Phe Ser Thr Thr Pro Gly Glu Ser Phe Gln Thr Thr Glu Asn Gln Ala
                500                 505                 510
Gly Gly Val Ala Glu Ser Thr Phe Ile Ala Ala Gln Phe Val Leu Tyr
            515                 520                 525
Gly Glu Gln Tyr Ala Glu Leu Ala Ala Arg Arg Gly Leu Ala Asp Val
        530                 535                 540
Ala Asp Arg Ala Arg Gly His Val Ala Glu Met Arg Asp Ala Leu Leu
545                 550                 555                 560
Thr Asp Gly Trp Asp Gly Ser Trp Phe Leu Arg Ala Tyr Asp Tyr Tyr
                565                 570                 575
Gly Asn Pro Ile Gly Thr Asp Ala His Asp Glu Gly Lys Ile Trp Ile
                580                 585                 590
Glu Pro Gln Gly Phe Ala Val Met Ala Gly Val Gly Val Gly Glu Gly
            595                 600                 605
Pro Gln Asp Thr Asp Ala Pro Ala Ile Lys Ala Leu Asp Ser Val Asn
        610                 615                 620
Glu Met Leu Ala Thr Asp His Gly Met Val Leu Gln Tyr Pro Ala Tyr
625                 630                 635                 640
Thr Thr Tyr Gln Val His Met Gly Glu Val Ser Thr Tyr Pro Pro Gly
                645                 650                 655
Tyr Lys Glu Asn Gly Gly Ile Phe Cys His Asn Asn Pro Trp Val Ile
                660                 665                 670
Ile Ala Glu Thr Val Val Gly Arg Gly Arg Ala Phe Asp Tyr Tyr
            675                 680                 685
Lys Arg Ile Thr Pro Ala Tyr Arg Glu Asp Ile Ser Asp Val His Arg
        690                 695                 700
Leu Glu Pro Tyr Val Tyr Ala Gln Met Ile Ala Gly Lys Glu Ala Val
705                 710                 715                 720
Arg His Gly Glu Ala Lys Asn Ser Trp Leu Thr Gly Thr Ala Ala Trp
                725                 730                 735
Asn Phe Val Thr Val Ser Gln Tyr Leu Leu Gly Val Arg Pro Glu Tyr
                740                 745                 750
Asp Gly Leu Val Val Asp Pro Gln Ile Gly Pro Asp Val Pro Ser Phe
            755                 760                 765
Thr Val Thr Arg Val Ala Arg Gly Ala Thr Tyr Glu Ile Thr Val Thr
        770                 775                 780
Asn Ser Gly Thr Asp Gly Ser Arg Gly Arg Leu Val Val Asp Gly Thr
785                 790                 795                 800
Pro Val Glu Gly Asn Leu Val Pro Tyr Ala Pro Ala Gly Ser Thr Val
                805                 810                 815
Arg Val Asp Val Thr Leu
            820
```

```
<210> SEQ ID NO 6
<211> LENGTH: 822
<212> TYPE: PRT
<213> ORGANISM: artificial
<220> FEATURE:
<223> OTHER INFORMATION: modified wildtye sequence

<400> SEQUENCE: 6

Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
            20                  25                  30

Phe Phe Ser Leu Leu Ser His Gln Ala Gly Gly Tyr Ser Phe Tyr Arg
        35                  40                  45

Asp Ala Lys Met Arg Arg Leu Thr Arg Tyr Tyr Asn Asn Ile Pro
    50                  55                  60

Ala Asp Ala Gly Gly Arg Tyr Leu Tyr Val Asn Asp Gly Asp Val
65                  70                  75                  80

Trp Thr Pro Ser Trp Leu Pro Val Lys Ala Asp Leu Asp His Phe Glu
            85                  90                  95

Ala Arg His Gly Leu Gly Tyr Ser Thr Ile Thr Gly Glu Arg Asn Gly
        100                 105                 110

Val Arg Val Glu Thr Leu Phe Phe Val Pro Val Gly Glu Asn Ala Glu
    115                 120                 125

Val Gln Lys Val Thr Val Thr Asn Thr Ser Asp Ser Tyr Lys Ser Leu
130                 135                 140

Thr Leu Phe Ser Phe Val Glu Phe Cys Leu Trp Asn Ala Gln Asp Asp
145                 150                 155                 160

Gln Thr Asn Tyr Gln Arg Asn Leu Ser Ile Gly Glu Val Glu Val
            165                 170                 175

Gln Glu Ser Pro His Gly Ser Ala Ile Tyr His Arg Thr Glu Tyr Arg
        180                 185                 190

Glu Arg Arg Asp His Tyr Ala Val Phe Ala Val Asn Thr Gln Ala Glu
    195                 200                 205

Gly Phe Asp Thr Asp Arg Asp Thr Phe Val Gly Leu Tyr Asn Ser Leu
210                 215                 220

Gly Glu Ala Ala Val Pro Leu Lys Gly Glu Ser Ala Asn Ser Val Ala
225                 230                 235                 240

Ser Gly Trp Tyr Pro Ile Gly Ser His Ser Val Ala Val Ser Leu Ala
            245                 250                 255

Pro Gly Glu Ser Arg Glu Leu Val Tyr Val Leu Gly Tyr Val Glu Asn
        260                 265                 270

Pro Asp Glu Glu Lys Trp Ala Asp Ala Lys Gln Val Val Asn Lys
    275                 280                 285

Glu Arg Ala His Ala Leu Leu Ser Arg Phe Ala Thr Ser Glu Gln Thr
290                 295                 300

Asp Ala Ala Phe Ala Ala Leu Lys Asp Tyr Trp Thr Asp Leu Leu Ser
305                 310                 315                 320

Thr Tyr Ser Val Ser Ser Asn Asp Glu Lys Leu Asp Arg Met Val Asn
            325                 330                 335

Ile Trp Asn Gln Tyr Gln Cys Met Val Thr Phe Asn Met Ser Arg Ser
        340                 345                 350

Ala Ser Phe Phe Glu Thr Gly Ile Gly Arg Gly Met Gly Phe Arg Asp
    355                 360                 365
```

```
Ser Asn Gln Asp Leu Leu Gly Phe Val His Leu Ile Pro Glu Arg Ala
    370             375                 380
Arg Glu Arg Ile Ile Asp Ile Ala Ser Thr Gln Phe Ala Asp Gly Ser
385                 390                 395                 400
Ala Tyr His Gln Tyr Gln Pro Leu Thr Lys Arg Gly Asn Asn Asp Ile
                405                 410                 415
Gly Ser Gly Phe Asn Asp Asp Pro Leu Trp Leu Ile Ala Gly Thr Ala
                420                 425                 430
Ala Tyr Ile Lys Glu Thr Gly Asp Phe Ser Ile Leu Asp Glu Pro Val
            435                 440                 445
Pro Phe Asp Asn Glu Pro Gly Ser Glu Val Pro Leu Phe Glu His Leu
450                 455                 460
Thr Arg Ser Phe Glu Phe Thr Val Thr His Arg Gly Pro His Gly Leu
465                 470                 475                 480
Pro Leu Ile Gly Arg Ala Asp Trp Asn Asp Cys Leu Asn Leu Asn Cys
                485                 490                 495
Phe Ser Thr Thr Pro Gly Glu Ser Phe Gln Thr Thr Glu Asn Gln Ala
                500                 505                 510
Gly Gly Val Ala Glu Ser Thr Phe Ile Ala Ala Gln Phe Val Leu Tyr
                515                 520                 525
Gly Glu Gln Tyr Ala Glu Leu Ala Ala Arg Arg Gly Leu Ala Asp Val
530                 535                 540
Ala Asp Arg Ala Arg Gly His Val Ala Glu Met Arg Asp Ala Leu Leu
545                 550                 555                 560
Thr Asp Gly Trp Asp Gly Ser Trp Phe Leu Arg Ala Tyr Asp Tyr Tyr
                565                 570                 575
Gly Asn Pro Ile Gly Thr Asp Ala His Asp Glu Gly Lys Ile Trp Ile
                580                 585                 590
Glu Pro Gln Gly Phe Ala Val Met Ala Gly Val Gly Val Gly Glu Gly
            595                 600                 605
Pro Gln Asp Thr Asp Ala Pro Ala Ile Lys Ala Leu Asp Ser Val Asn
            610                 615                 620
Glu Met Leu Ala Thr Asp His Gly Met Val Leu Gln Tyr Pro Ala Tyr
625                 630                 635                 640
Thr Thr Tyr Gln Val His Met Gly Glu Val Ser Thr Tyr Pro Pro Gly
                645                 650                 655
Tyr Lys Glu Asn Gly Gly Ile Phe Cys His Asn Asn Pro Trp Val Ile
                660                 665                 670
Ile Ala Glu Thr Val Val Gly Arg Gly Gly Arg Ala Phe Asp Tyr Tyr
                675                 680                 685
Lys Arg Ile Thr Pro Ala Tyr Arg Glu Asp Ile Ser Asp Val His Arg
            690                 695                 700
Leu Glu Pro Tyr Val Tyr Ala Gln Met Ile Ala Gly Lys Glu Ala Val
705                 710                 715                 720
Arg His Gly Glu Ala Lys Asn Ser Trp Leu Thr Gly Thr Ala Ala Trp
                725                 730                 735
Asn Phe Val Thr Val Ser Gln Tyr Leu Leu Gly Val Arg Pro Glu Tyr
                740                 745                 750
Asp Gly Leu Val Val Asp Pro Gln Ile Gly Pro Asp Val Pro Ser Phe
                755                 760                 765
Thr Val Thr Arg Val Ala Arg Gly Ala Thr Tyr Glu Ile Thr Val Thr
770                 775                 780
Asn Ser Gly Thr Asp Gly Ser Arg Gly Arg Leu Val Val Asp Gly Thr
```

```
                    785                 790                 795                 800
Pro Val Glu Gly Asn Leu Val Pro Tyr Ala Pro Ala Gly Ser Thr Val
                805                 810                 815
Arg Val Asp Val Thr Leu
            820

<210> SEQ ID NO 7
<211> LENGTH: 822
<212> TYPE: PRT
<213> ORGANISM: artificial
<220> FEATURE:
<223> OTHER INFORMATION: modified wildtye sequence

<400> SEQUENCE: 7

Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
                20                  25                  30

Phe Phe Ser Leu Leu Ser His Gln Ala Gly Gly Tyr Ser Phe Tyr Arg
            35                  40                  45

Asp Ala Lys Met Arg Arg Leu Thr Arg Tyr Arg Tyr Asn Asn Ile Pro
50                  55                  60

Ala Asp Ala Gly Gly Arg Tyr Leu Tyr Val Asn Asp Gly Gly Asp Val
65                  70                  75                  80

Trp Thr Pro Ser Trp Leu Pro Val Lys Ala Asp Leu Asp His Phe Glu
                85                  90                  95

Ala Arg His Gly Leu Gly Tyr Ser Thr Ile Thr Gly Glu Arg Asn Gly
                100                 105                 110

Val Arg Val Glu Thr Leu Phe Phe Val Pro Val Gly Glu Asn Ala Glu
            115                 120                 125

Val Gln Lys Val Thr Val Thr Asn Thr Ser Asp Ser Tyr Lys Ser Leu
130                 135                 140

Thr Leu Phe Ser Phe Val Glu Phe Cys Leu Trp Asn Ala Gln Asp Asp
145                 150                 155                 160

Gln Thr Asn Tyr Gln Arg Asn Leu Ser Ile Gly Glu Val Glu Val Glu
                165                 170                 175

Gln Glu Ser Pro His Gly Ser Ala Ile Tyr His Arg Thr Glu Tyr Arg
            180                 185                 190

Glu Arg Arg Asp His Tyr Ala Val Phe Ala Val Asn Thr Gln Ala Glu
            195                 200                 205

Gly Phe Asp Thr Asp Arg Asp Thr Phe Val Gly Ala Tyr Asn Ser Leu
210                 215                 220

Gly Glu Ala Ala Val Pro Leu Lys Gly Glu Ser Ala Asn Ser Val Ala
225                 230                 235                 240

Ser Gly Trp Tyr Pro Ile Gly Ser His Ser Val Ala Val Ser Leu Ala
                245                 250                 255

Pro Gly Glu Ser Arg Glu Leu Val Tyr Val Leu Gly Tyr Val Glu Asn
            260                 265                 270

Pro Asp Glu Glu Lys Trp Ala Asp Ala Lys Gln Val Val Asn Lys
            275                 280                 285

Glu Arg Ala His Ala Leu Leu Ser Arg Phe Ala Thr Ser Glu Gln Thr
            290                 295                 300

Asp Ala Ala Phe Ala Ala Leu Lys Asp Tyr Trp Thr Asp Leu Leu Ser
305                 310                 315                 320

Thr Tyr Ser Val Ser Ser Asn Asp Glu Lys Leu Asp Arg Met Val Asn
```

-continued

```
                325                 330                 335
Ile Trp Asn Gln Tyr Gln Cys Met Val Thr Phe Asn Met Ser Arg Ser
            340                 345                 350
Ala Ser Phe Phe Glu Thr Gly Ile Gly Arg Gly Met Gly Phe Arg Asp
            355                 360                 365
Ser Asn Gln Asp Leu Leu Gly Phe Val His Leu Ile Pro Glu Arg Ala
            370                 375                 380
Arg Glu Arg Ile Ile Asp Ile Ala Ser Thr Gln Phe Ala Asp Gly Ser
385                 390                 395                 400
Ala Tyr His Gln Tyr Gln Pro Leu Thr Lys Arg Gly Asn Asn Asp Ile
            405                 410                 415
Gly Ser Gly Phe Asn Asp Asp Pro Leu Trp Leu Ile Ala Gly Thr Ala
            420                 425                 430
Ala Tyr Ile Lys Glu Thr Gly Asp Phe Ser Ile Leu Asp Glu Pro Val
            435                 440                 445
Pro Phe Asp Asn Glu Pro Gly Ser Glu Val Pro Leu Phe Glu His Leu
            450                 455                 460
Thr Arg Ser Phe Glu Phe Thr Val Thr His Arg Gly Pro His Gly Leu
465                 470                 475                 480
Pro Leu Ile Gly Arg Ala Asp Trp Asn Asp Cys Leu Asn Leu Asn Cys
            485                 490                 495
Phe Ser Thr Thr Pro Gly Glu Ser Phe Gln Thr Thr Glu Asn Gln Ala
            500                 505                 510
Gly Gly Val Ala Glu Ser Thr Phe Ile Ala Ala Gln Phe Val Leu Tyr
            515                 520                 525
Gly Glu Gln Tyr Ala Glu Leu Ala Ala Arg Arg Gly Leu Ala Asp Val
            530                 535                 540
Ala Asp Arg Ala Arg Gly His Val Ala Glu Met Arg Asp Ala Leu Leu
545                 550                 555                 560
Thr Asp Gly Trp Asp Gly Ser Trp Phe Leu Arg Ala Tyr Asp Tyr Tyr
            565                 570                 575
Gly Asn Pro Ile Gly Thr Asp Ala His Asp Glu Gly Lys Ile Trp Ile
            580                 585                 590
Glu Pro Gln Gly Phe Ala Val Met Ala Gly Val Gly Val Gly Glu Gly
            595                 600                 605
Pro Gln Asp Thr Asp Ala Pro Ala Ile Lys Ala Leu Asp Ser Val Asn
            610                 615                 620
Glu Met Leu Ala Thr Asp His Gly Met Val Leu Gln Tyr Pro Ala Tyr
625                 630                 635                 640
Thr Thr Tyr Gln Val His Met Gly Glu Val Ser Thr Tyr Pro Pro Gly
            645                 650                 655
Tyr Lys Glu Asn Gly Gly Ile Phe Cys His Asn Asn Pro Trp Val Ile
            660                 665                 670
Ile Ala Glu Thr Val Val Gly Arg Gly Arg Ala Phe Asp Tyr Tyr
            675                 680                 685
Lys Arg Ile Thr Pro Ala Tyr Arg Glu Asp Ile Ser Asp Val His Arg
            690                 695                 700
Thr Glu Pro Tyr Val Tyr Ala Gln Met Ile Ala Gly Lys Glu Ala Val
705                 710                 715                 720
Arg His Gly Glu Ala Lys Asn Ser Trp Leu Thr Gly Thr Ala Ala Trp
            725                 730                 735
Asn Phe Val Thr Val Ser Gln Tyr Leu Leu Gly Val Arg Pro Glu Tyr
            740                 745                 750
```

Asp Gly Leu Val Val Asp Pro Gln Ile Gly Pro Asp Val Pro Ser Phe
            755                 760                 765

Thr Val Thr Arg Val Ala Arg Gly Ala Thr Tyr Glu Ile Thr Val Thr
770                 775                 780

Asn Ser Gly Thr Asp Gly Ser Arg Gly Arg Leu Val Val Asp Gly Thr
785                 790                 795                 800

Pro Val Glu Gly Asn Leu Val Pro Tyr Ala Pro Ala Gly Ser Thr Val
            805                 810                 815

Arg Val Asp Val Thr Leu
            820

<210> SEQ ID NO 8
<211> LENGTH: 822
<212> TYPE: PRT
<213> ORGANISM: artificial
<220> FEATURE:
<223> OTHER INFORMATION: modified wildtye sequence

<400> SEQUENCE: 8

Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
            20                  25                  30

Phe Phe Ser Leu Leu Ser His Gln Ala Gly Tyr Ser Phe Tyr Arg
        35                  40                  45

Asp Ala Lys Met Arg Arg Leu Thr Arg Tyr Arg Tyr Asn Asn Ile Pro
    50                  55                  60

Ala Asp Ala Gly Gly Arg Tyr Leu Tyr Val Asn Asp Gly Gly Asp Val
65                  70                  75                  80

Trp Thr Pro Ser Trp Leu Pro Val Lys Ala Asp Leu Asp His Phe Glu
            85                  90                  95

Ala Arg His Gly Leu Gly Tyr Ser Thr Ile Thr Gly Glu Arg Asn Gly
            100                 105                 110

Val Arg Val Glu Thr Leu Phe Phe Val Pro Val Gly Glu Asn Ala Glu
        115                 120                 125

Val Gln Lys Val Thr Val Thr Asn Thr Ser Asp Ser Tyr Lys Ser Leu
    130                 135                 140

Thr Leu Phe Ser Phe Val Glu Phe Cys Leu Trp Asn Ala Gln Asp Asp
145                 150                 155                 160

Met Thr Asn Tyr Gln Arg Asn Leu Ser Ile Gly Glu Val Glu Val Glu
            165                 170                 175

Gln Glu Ser Pro His Gly Ser Ala Ile Tyr His Lys Thr Glu Tyr Arg
            180                 185                 190

Glu Arg Arg Asn His Tyr Ala Val Phe Ala Val Asn Thr Gln Ala Glu
        195                 200                 205

Gly Phe Asp Thr Asp Arg Asp Thr Phe Val Gly Leu Tyr Asn Ser Leu
    210                 215                 220

Gly Glu Ala Ala Val Pro Leu Lys Gly Glu Ser Ala Asn Ser Val Ala
225                 230                 235                 240

Ser Gly Trp Tyr Pro Ile Gly Ser His Ser Val Ala Val Ser Leu Ala
            245                 250                 255

Pro Gly Glu Ser Arg Glu Leu Val Tyr Val Leu Gly Tyr Val Glu Asn
            260                 265                 270

Pro Asp Glu Glu Lys Trp Ala Asp Ala Lys Gln Val Val Asn Lys
        275                 280                 285

```
Glu Arg Ala His Ala Leu Leu Ser Arg Phe Ala Thr Ser Glu Gln Thr
290                 295                 300

Asp Ala Ala Phe Ala Ala Leu Lys Asp Tyr Trp Thr Asp Leu Leu Ser
305                 310                 315                 320

Thr Tyr Ser Val Ser Ser Asn Asp Glu Lys Leu Asp Arg Met Val Asn
            325                 330                 335

Ile Trp Asn Gln Tyr Gln Cys Met Val Thr Phe Asn Met Ser Arg Ser
            340                 345                 350

Ala Ser Phe Phe Glu Thr Gly Ile Gly Arg Gly Met Gly Phe Arg Asp
            355                 360                 365

Ser Asn Gln Asp Leu Leu Gly Phe Val His Leu Ile Pro Glu Arg Ala
370                 375                 380

Arg Glu Arg Ile Ile Asp Ile Ala Ser Thr Gln Phe Ala Asp Gly Ser
385                 390                 395                 400

Ala Tyr His Gln Tyr Gln Pro Leu Thr Lys Arg Gly Asn Asn Asp Ile
                405                 410                 415

Gly Ser Gly Phe Asn Asp Asp Pro Leu Trp Leu Ile Ala Gly Thr Ala
            420                 425                 430

Ala Tyr Ile Lys Glu Thr Gly Asp Phe Ser Ile Leu Asp Glu Pro Val
            435                 440                 445

Pro Phe Asp Asn Glu Pro Gly Ser Glu Val Pro Leu Phe Glu His Leu
450                 455                 460

Thr Arg Ser Phe Glu Phe Thr Val Thr His Arg Gly Pro His Gly Leu
465                 470                 475                 480

Pro Leu Ile Gly Arg Ala Asp Trp Asn Asp Cys Leu Asn Leu Asn Cys
            485                 490                 495

Phe Ser Thr Thr Pro Gly Glu Ser Phe Gln Thr Thr Glu Asn Gln Ala
            500                 505                 510

Gly Gly Val Ala Glu Ser Thr Phe Ile Ala Ala Gln Phe Val Leu Tyr
            515                 520                 525

Gly Glu Gln Tyr Ala Glu Leu Ala Ala Arg Arg Gly Leu Ala Asp Val
            530                 535                 540

Ala Asp Arg Ala Arg Gly His Val Ala Glu Met Arg Asp Ala Leu Leu
545                 550                 555                 560

Thr Asp Gly Trp Asp Gly Ser Trp Phe Leu Arg Ala Tyr Asp Tyr Tyr
            565                 570                 575

Gly Asn Pro Ile Gly Thr Asp Ala His Asp Glu Gly Lys Ile Trp Ile
            580                 585                 590

Glu Pro Gln Gly Phe Ala Val Met Ala Gly Val Gly Gly Glu Gly
            595                 600                 605

Pro Gln Asp Thr Asp Ala Pro Ala Ile Lys Ala Leu Asp Ser Val Asn
610                 615                 620

Glu Met Leu Ala Thr Asp His Gly Met Val Leu Gln Tyr Pro Ala Tyr
625                 630                 635                 640

Thr Thr Tyr Gln Val His Met Gly Glu Val Ser Thr Tyr Pro Pro Gly
            645                 650                 655

Tyr Lys Glu Asn Gly Gly Ile Phe Cys His Asn Asn Pro Trp Val Ile
            660                 665                 670

Ile Ala Glu Thr Val Val Gly Arg Gly Gly Arg Ala Phe Asp Tyr Tyr
            675                 680                 685

Lys Arg Ile Thr Pro Ala Tyr Arg Glu Asp Ile Ser Asp Val His Arg
690                 695                 700
```

```
Thr Glu Pro Tyr Val Tyr Ala Gln Met Ile Ala Gly Lys Glu Ala Val
705                 710                 715                 720

Arg His Gly Glu Ala Lys Asn Ser Trp Leu Thr Gly Thr Ala Ala Trp
            725                 730                 735

Asn Phe Val Thr Val Ser Gln Tyr Leu Leu Gly Val Arg Pro Glu Tyr
                740                 745                 750

Asp Gly Leu Val Val Asp Pro Gln Ile Gly Pro Asp Val Pro Ser Phe
            755                 760                 765

Thr Val Thr Arg Val Ala Arg Gly Ala Thr Tyr Glu Ile Thr Val Thr
    770                 775                 780

Asn Ser Gly Thr Asp Gly Ser Arg Gly Arg Leu Val Val Asp Gly Thr
785                 790                 795                 800

Pro Val Glu Gly Asn Leu Val Pro Tyr Ala Pro Ala Gly Ser Thr Val
                805                 810                 815

Arg Val Asp Val Thr Leu
            820
```

<210> SEQ ID NO 9
<211> LENGTH: 822
<212> TYPE: PRT
<213> ORGANISM: artificial
<220> FEATURE:
<223> OTHER INFORMATION: modified wildtye sequence

<400> SEQUENCE: 9

```
Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
            20                  25                  30

Phe Phe Ser Leu Leu Ser His Gln Ala Gly Gly Tyr Ser Phe Tyr Arg
        35                  40                  45

Asp Ala Lys Met Arg Arg Leu Thr Arg Tyr Arg Tyr Asn Asn Ile Pro
    50                  55                  60

Ala Asp Ala Gly Gly Arg Tyr Leu Tyr Val Asn Asp Gly Gly Asp Val
65                  70                  75                  80

Trp Thr Pro Ser Trp Leu Pro Val Lys Ala Asp Leu Asp His Phe Glu
                85                  90                  95

Ala Arg His Gly Leu Gly Tyr Ser Thr Ile Thr Gly Glu Arg Asn Gly
            100                 105                 110

Val Arg Val Glu Thr Leu Phe Phe Val Pro Val Gly Glu Asn Ala Glu
        115                 120                 125

Val Gln Lys Val Thr Val Thr Asn Thr Ser Asp Ser Tyr Lys Ser Leu
    130                 135                 140

Thr Leu Phe Ser Phe Val Glu Phe Cys Leu Trp Asn Ala Gln Asp Asp
145                 150                 155                 160

Met Thr Asn Tyr Gln Lys Asn Leu Ser Ile Gly Glu Val Glu Val Glu
                165                 170                 175

Gln Glu Ser Pro His Gly Ser Ala Ile Tyr His Lys Thr Glu Tyr Arg
            180                 185                 190

Glu Arg Arg Asn His Tyr Ala Val Phe Ala Val Asn Thr Gln Ala Glu
        195                 200                 205

Gly Phe Asp Thr Asp Arg Asp Thr Phe Val Gly Leu Tyr Asn Ser Leu
    210                 215                 220

Gly Glu Ala Ala Val Pro Leu Lys Gly Glu Ser Ala Asn Ser Val Ala
225                 230                 235                 240
```

-continued

```
Ser Gly Trp Tyr Pro Ile Gly Ser His Ser Val Ala Val Ser Leu Ala
                245                 250                 255
Pro Gly Glu Ser Arg Glu Leu Val Tyr Val Leu Gly Tyr Val Glu Asn
            260                 265                 270
Pro Asp Glu Glu Lys Trp Ala Asp Ala Lys Gln Val Val Asn Lys
        275                 280                 285
Glu Arg Ala His Ala Leu Leu Ser Arg Phe Ala Thr Ser Glu Gln Thr
    290                 295                 300
Asp Ala Ala Phe Ala Ala Leu Lys Asp Tyr Trp Thr Asp Leu Leu Ser
305                 310                 315                 320
Thr Tyr Ser Val Ser Ser Asn Asp Glu Lys Leu Asp Arg Met Val Asn
                325                 330                 335
Ile Trp Asn Gln Tyr Gln Cys Met Val Thr Phe Asn Met Ser Arg Ser
            340                 345                 350
Ala Ser Phe Phe Glu Thr Gly Ile Gly Arg Gly Met Gly Phe Arg Asp
        355                 360                 365
Ser Asn Gln Asp Leu Leu Gly Phe Val His Leu Ile Pro Glu Arg Ala
    370                 375                 380
Arg Glu Arg Ile Ile Asp Ile Ala Ser Thr Gln Phe Ala Asp Gly Ser
385                 390                 395                 400
Ala Tyr His Gln Tyr Gln Pro Leu Thr Lys Arg Gly Asn Asn Asp Ile
                405                 410                 415
Gly Ser Gly Phe Asn Asp Asp Pro Leu Trp Leu Ile Ala Gly Thr Ala
            420                 425                 430
Ala Tyr Ile Lys Glu Thr Gly Asp Phe Ser Ile Leu Asp Glu Pro Val
        435                 440                 445
Pro Phe Asp Asn Glu Pro Gly Ser Glu Val Pro Leu Phe Glu His Leu
    450                 455                 460
Thr Arg Ser Phe Glu Phe Thr Val Thr His Arg Gly Pro His Gly Leu
465                 470                 475                 480
Pro Leu Ile Gly Arg Ala Asp Trp Asn Asp Cys Leu Asn Leu Asn Cys
                485                 490                 495
Phe Ser Thr Thr Pro Gly Glu Ser Phe Gln Thr Thr Glu Asn Gln Ala
            500                 505                 510
Gly Gly Val Ala Glu Ser Thr Phe Ile Ala Ala Gln Phe Val Leu Tyr
        515                 520                 525
Gly Glu Gln Tyr Ala Glu Leu Ala Ala Arg Arg Gly Leu Ala Asp Val
    530                 535                 540
Ala Asp Arg Ala Arg Gly His Val Ala Glu Met Arg Asp Ala Leu Leu
545                 550                 555                 560
Thr Asp Gly Trp Asp Gly Ser Trp Phe Leu Arg Ala Tyr Asp Tyr Tyr
                565                 570                 575
Gly Asn Pro Ile Gly Thr Asp Ala His Asp Glu Gly Lys Ile Trp Ile
            580                 585                 590
Glu Pro Gln Gly Phe Ala Val Met Ala Gly Val Gly Val Gly Glu Gly
        595                 600                 605
Pro Gln Asp Thr Asp Ala Pro Ala Ile Lys Ala Leu Asp Ser Val Asn
    610                 615                 620
Glu Met Leu Ala Thr Asp His Gly Met Val Leu Gln Tyr Pro Ala Tyr
625                 630                 635                 640
Thr Thr Tyr Gln Val His Met Gly Glu Val Ser Thr Tyr Pro Pro Gly
                645                 650                 655
Tyr Lys Glu Asn Gly Gly Ile Phe Cys His Asn Asn Pro Trp Val Ile
```

```
                    660                 665                 670
Ile Ala Glu Thr Val Val Gly Arg Gly Gly Arg Ala Phe Asp Tyr Tyr
                675                 680                 685

Lys Arg Ile Thr Pro Ala Tyr Arg Glu Asp Ile Ser Asp Val His Arg
            690                 695                 700

Thr Glu Pro Tyr Val Tyr Ala Gln Met Ile Ala Gly Lys Glu Ala Val
705                 710                 715                 720

Arg His Gly Glu Ala Lys Asn Ser Trp Leu Thr Gly Thr Ala Ala Trp
                725                 730                 735

Asn Phe Val Thr Val Ser Gln Tyr Leu Leu Gly Val Arg Pro Glu Tyr
                740                 745                 750

Asp Gly Leu Val Val Asp Pro Gln Ile Gly Pro Asp Val Pro Ser Phe
            755                 760                 765

Thr Val Thr Arg Val Ala Arg Gly Ala Thr Tyr Glu Ile Thr Val Thr
770                 775                 780

Asn Ser Gly Thr Asp Gly Ser Arg Gly Arg Leu Val Val Asp Gly Thr
785                 790                 795                 800

Pro Val Glu Gly Asn Leu Val Pro Tyr Ala Pro Ala Gly Ser Thr Val
                805                 810                 815

Arg Val Asp Val Thr Leu
            820

<210> SEQ ID NO 10
<211> LENGTH: 822
<212> TYPE: PRT
<213> ORGANISM: artificial
<220> FEATURE:
<223> OTHER INFORMATION: modified wildtye sequence

<400> SEQUENCE: 10

Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
            20                  25                  30

Phe Phe Ser Leu Leu Ser His Gln Ala Gly Gly Tyr Ser Phe Tyr Arg
        35                  40                  45

Asp Ala Lys Met Arg Arg Leu Thr Arg Tyr Arg Tyr Asn Asn Ile Pro
50                  55                  60

Ala Asp Ala Gly Gly Arg Tyr Leu Tyr Val Asn Asp Gly Gly Asp Val
65                  70                  75                  80

Trp Thr Pro Ser Trp Leu Pro Val Lys Ala Asp Leu Asp His Phe Glu
                85                  90                  95

Ala Arg His Gly Leu Gly Tyr Ser Thr Ile Thr Gly Glu Arg Asn Gly
            100                 105                 110

Val Arg Val Glu Thr Leu Phe Phe Val Pro Val Gly Glu Asn Ala Glu
        115                 120                 125

Val Gln Lys Val Thr Val Thr Asn Thr Ser Asp Ser Tyr Lys Ser Leu
130                 135                 140

Thr Leu Phe Ser Phe Val Glu Phe Cys Leu Trp Asn Ala Gln Asp Asp
145                 150                 155                 160

Met Thr Asn Tyr Gln Met Asn Leu Ser Ile Gly Glu Val Glu Val Glu
                165                 170                 175

Gln Glu Ser Pro His Gly Ser Ala Ile Tyr His Lys Thr Glu Tyr Arg
            180                 185                 190

Glu Arg Arg Asn His Tyr Ala Val Phe Ala Val Asn Thr Gln Ala Glu
```

-continued

```
            195                 200                 205
Gly Phe Asp Thr Asp Arg Asp Thr Phe Val Gly Leu Tyr Asn Ser Leu
210                 215                 220

Gly Glu Ala Ala Val Pro Leu Lys Gly Glu Ser Ala Asn Ser Val Ala
225                 230                 235                 240

Ser Gly Trp Tyr Pro Ile Gly Ser His Ser Val Ala Val Ser Leu Ala
                    245                 250                 255

Pro Gly Glu Ser Arg Glu Leu Val Tyr Val Leu Gly Tyr Val Glu Asn
                260                 265                 270

Pro Asp Glu Glu Lys Trp Ala Asp Ala Lys Gln Val Val Asn Lys
                275                 280                 285

Glu Arg Ala His Ala Leu Leu Ser Arg Phe Ala Thr Ser Glu Gln Thr
290                 295                 300

Asp Ala Ala Phe Ala Ala Leu Lys Asp Tyr Trp Thr Asp Leu Leu Ser
305                 310                 315                 320

Thr Tyr Ser Val Ser Ser Asn Asp Glu Lys Leu Asp Arg Met Val Asn
                    325                 330                 335

Ile Trp Asn Gln Tyr Gln Cys Met Val Thr Phe Asn Met Ser Arg Ser
                340                 345                 350

Ala Ser Phe Phe Glu Thr Gly Ile Gly Arg Gly Met Gly Phe Arg Asp
                355                 360                 365

Ser Asn Gln Asp Leu Leu Gly Phe Val His Leu Ile Pro Glu Arg Ala
                370                 375                 380

Arg Glu Arg Ile Ile Asp Ile Ala Ser Thr Gln Phe Ala Asp Gly Ser
385                 390                 395                 400

Ala Tyr His Gln Tyr Gln Pro Leu Thr Lys Arg Gly Asn Asn Asp Ile
                    405                 410                 415

Gly Ser Gly Phe Asn Asp Asp Pro Leu Trp Leu Ile Ala Gly Thr Ala
                420                 425                 430

Ala Tyr Ile Lys Glu Thr Gly Asp Phe Ser Ile Leu Asp Glu Pro Val
                435                 440                 445

Pro Phe Asp Asn Glu Pro Gly Ser Glu Val Pro Leu Phe Glu His Leu
450                 455                 460

Thr Arg Ser Phe Glu Phe Thr Val Thr His Arg Gly Pro His Gly Leu
465                 470                 475                 480

Pro Leu Ile Gly Arg Ala Asp Trp Asn Asp Cys Leu Asn Leu Asn Cys
                    485                 490                 495

Phe Ser Thr Thr Pro Gly Glu Ser Phe Gln Thr Thr Glu Asn Gln Ala
                500                 505                 510

Gly Gly Val Ala Glu Ser Thr Phe Ile Ala Ala Gln Phe Val Leu Tyr
                515                 520                 525

Gly Glu Gln Tyr Ala Glu Leu Ala Ala Arg Arg Gly Leu Ala Asp Val
530                 535                 540

Ala Asp Arg Ala Arg Gly His Val Ala Glu Met Arg Asp Ala Leu Leu
545                 550                 555                 560

Thr Asp Gly Trp Asp Gly Ser Trp Phe Leu Arg Ala Tyr Asp Tyr Tyr
                    565                 570                 575

Gly Asn Pro Ile Gly Thr Asp Ala His Asp Glu Gly Lys Ile Trp Ile
                580                 585                 590

Glu Pro Gln Gly Phe Ala Val Met Ala Gly Val Gly Val Gly Glu Gly
                595                 600                 605

Pro Gln Asp Thr Asp Ala Pro Ala Ile Lys Ala Leu Asp Ser Val Asn
610                 615                 620
```

```
Glu Met Leu Ala Thr Asp His Gly Met Val Leu Gln Tyr Pro Ala Tyr
625                 630                 635                 640

Thr Thr Tyr Gln Val His Met Gly Glu Val Ser Thr Tyr Pro Pro Gly
            645                 650                 655

Tyr Lys Glu Asn Gly Gly Ile Phe Cys His Asn Asn Pro Trp Val Ile
        660                 665                 670

Ile Ala Glu Thr Val Val Gly Arg Gly Gly Arg Ala Phe Asp Tyr Tyr
            675                 680                 685

Lys Arg Ile Thr Pro Ala Tyr Arg Glu Asp Ile Ser Asp Val His Arg
        690                 695                 700

Thr Glu Pro Tyr Val Tyr Ala Gln Met Ile Ala Gly Lys Glu Ala Val
705                 710                 715                 720

Arg His Gly Glu Ala Lys Asn Ser Trp Leu Thr Gly Thr Ala Ala Trp
            725                 730                 735

Asn Phe Val Thr Val Ser Gln Tyr Leu Leu Gly Val Arg Pro Glu Tyr
        740                 745                 750

Asp Gly Leu Val Val Asp Pro Gln Ile Gly Pro Asp Val Pro Ser Phe
        755                 760                 765

Thr Val Thr Arg Val Ala Arg Gly Ala Thr Tyr Glu Ile Thr Val Thr
770                 775                 780

Asn Ser Gly Thr Asp Gly Ser Arg Gly Arg Leu Val Val Asp Gly Thr
785                 790                 795                 800

Pro Val Glu Gly Asn Leu Val Pro Tyr Ala Pro Ala Gly Ser Thr Val
            805                 810                 815

Arg Val Asp Val Thr Leu
            820

<210> SEQ ID NO 11
<211> LENGTH: 822
<212> TYPE: PRT
<213> ORGANISM: artificial
<220> FEATURE:
<223> OTHER INFORMATION: modified wildtye sequence

<400> SEQUENCE: 11

Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
            20                  25                  30

Phe Phe Ser Leu Leu Ser His Gln Ala Gly Gly Tyr Ser Phe Tyr Arg
        35                  40                  45

Asp Ala Lys Met Arg Arg Leu Thr Arg Tyr Arg Tyr Asn Asn Ile Pro
    50                  55                  60

Ala Asp Ala Gly Gly Arg Tyr Leu Tyr Val Asn Asp Gly Gly Asp Val
65                  70                  75                  80

Trp Thr Pro Ser Trp Leu Pro Val Lys Ala Asp Leu Asp His Phe Glu
                85                  90                  95

Ala Arg His Gly Leu Gly Tyr Ser Thr Ile Thr Gly Glu Arg Asn Gly
            100                 105                 110

Val Arg Val Glu Thr Leu Phe Phe Val Pro Val Gly Leu Asn Ala Glu
        115                 120                 125

Val Gln Lys Val Thr Val Thr Asn Thr Ser Asp Ser Tyr Lys Ser Leu
    130                 135                 140

Thr Leu Phe Ser Phe Val Glu Phe Cys Leu Trp Asn Ala Gln Asp Asp
145                 150                 155                 160
```

```
Met Thr Asn Phe Gln Arg Asn Leu Ser Ile Gly Glu Val Glu Val Glu
                165                 170                 175

Gln Glu Ser Pro His Gly Ser Ala Ile Tyr His Lys Thr Glu Tyr Arg
            180                 185                 190

Glu Arg Arg Asn His Tyr Ala Val Phe Ala Val Asn Thr Gln Ala Glu
        195                 200                 205

Gly Phe Asp Thr Asp Arg Asp Thr Phe Val Gly Leu Tyr Asn Ser Leu
    210                 215                 220

Gly Glu Ala Ala Val Pro Leu Lys Gly Glu Ser Ala Asn Ser Val Ala
225                 230                 235                 240

Ser Gly Trp Tyr Pro Ile Gly Ser His Ser Val Ala Val Ser Leu Ala
                245                 250                 255

Pro Gly Glu Ser Arg Glu Leu Val Tyr Val Leu Gly Tyr Val Glu Asn
            260                 265                 270

Pro Asp Glu Glu Lys Trp Ala Asp Ala Lys Gln Val Val Asn Lys
        275                 280                 285

Glu Arg Ala His Ala Leu Leu Ser Arg Phe Ala Thr Ser Glu Gln Thr
    290                 295                 300

Asp Ala Ala Phe Ala Ala Leu Lys Asp Tyr Trp Thr Asp Leu Leu Ser
305                 310                 315                 320

Thr Tyr Ser Val Ser Ser Asn Asp Glu Lys Leu Asp Arg Met Val Asn
                325                 330                 335

Ile Trp Asn Gln Tyr Gln Cys Met Val Thr Phe Asn Met Ser Arg Ser
            340                 345                 350

Ala Ser Phe Phe Glu Thr Gly Ile Gly Arg Gly Met Gly Phe Arg Asp
        355                 360                 365

Ser Asn Gln Asp Leu Leu Gly Phe Val His Leu Ile Pro Glu Arg Ala
    370                 375                 380

Arg Glu Arg Ile Ile Asp Ile Ala Ser Thr Gln Phe Ala Asp Gly Ser
385                 390                 395                 400

Ala Tyr His Gln Tyr Gln Pro Leu Thr Lys Arg Gly Asn Asn Asp Ile
                405                 410                 415

Gly Ser Gly Phe Asn Asp Asp Pro Leu Trp Leu Ile Ala Gly Thr Ala
            420                 425                 430

Ala Tyr Ile Lys Glu Thr Gly Asp Phe Ser Ile Leu Asp Glu Pro Val
        435                 440                 445

Pro Phe Asp Asn Glu Pro Gly Ser Glu Val Pro Leu Phe Glu His Leu
    450                 455                 460

Thr Arg Ser Phe Glu Phe Thr Val Thr His Arg Gly Pro His Gly Leu
465                 470                 475                 480

Pro Leu Ile Gly Arg Ala Asp Trp Asn Asp Cys Leu Asn Leu Asn Cys
                485                 490                 495

Phe Ser Thr Thr Pro Gly Glu Ser Phe Gln Thr Thr Glu Asn Gln Ala
            500                 505                 510

Gly Gly Val Ala Glu Ser Thr Phe Ile Ala Ala Gln Phe Val Leu Tyr
        515                 520                 525

Gly Glu Gln Tyr Ala Glu Leu Ala Ala Arg Gly Leu Ala Asp Val
    530                 535                 540

Ala Asp Arg Ala Arg Gly His Val Ala Glu Met Arg Asp Ala Leu Leu
545                 550                 555                 560

Thr Asp Gly Trp Asp Gly Ser Trp Phe Leu Arg Ala Tyr Asp Tyr Tyr
                565                 570                 575
```

Gly Asn Pro Ile Gly Thr Asp Ala His Asp Glu Gly Lys Ile Trp Ile
            580                 585                 590

Glu Pro Gln Gly Phe Ala Val Met Ala Gly Val Gly Val Gly Glu Gly
            595                 600                 605

Pro Gln Asp Thr Asp Ala Pro Ala Ile Lys Ala Leu Asp Ser Val Asn
610                 615                 620

Glu Met Leu Ala Thr Asp His Gly Met Val Leu Gln Tyr Pro Ala Tyr
625                 630                 635                 640

Thr Thr Tyr Gln Val His Met Gly Glu Val Ser Thr Tyr Pro Pro Gly
            645                 650                 655

Tyr Lys Glu Asn Gly Gly Ile Phe Cys His Asn Asn Pro Trp Val Ile
            660                 665                 670

Ile Ala Glu Thr Val Val Gly Arg Gly Gly Arg Ala Phe Asp Tyr Tyr
            675                 680                 685

Lys Arg Ile Thr Pro Ala Tyr Arg Glu Asp Ile Ser Asp Val His Arg
            690                 695                 700

Thr Glu Pro Tyr Val Tyr Ala Gln Met Ile Ala Gly Lys Glu Ala Val
705                 710                 715                 720

Arg His Gly Glu Ala Lys Asn Ser Trp Leu Thr Gly Thr Ala Ala Trp
            725                 730                 735

Asn Phe Val Thr Val Ser Gln Tyr Leu Leu Gly Val Arg Pro Glu Tyr
            740                 745                 750

Asp Gly Leu Val Val Asp Pro Gln Ile Gly Pro Asp Val Pro Ser Phe
            755                 760                 765

Thr Val Thr Arg Val Ala Arg Gly Ala Thr Tyr Glu Ile Thr Val Thr
            770                 775                 780

Asn Ser Gly Thr Asp Gly Ser Arg Gly Arg Leu Val Val Asp Gly Thr
785                 790                 795                 800

Pro Val Glu Gly Asn Leu Val Pro Tyr Ala Pro Ala Gly Ser Thr Val
            805                 810                 815

Arg Val Asp Val Thr Leu
            820

<210> SEQ ID NO 12
<211> LENGTH: 822
<212> TYPE: PRT
<213> ORGANISM: artificial
<220> FEATURE:
<223> OTHER INFORMATION: modified wildtye sequence

<400> SEQUENCE: 12

Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
            20                  25                  30

Phe Phe Ser Leu Leu Ser His Gln Ala Gly Gly Tyr Ser Phe Tyr Arg
        35                  40                  45

Asp Ala Lys Met Arg Arg Leu Thr Arg Tyr Arg Tyr Asn Asn Ile Pro
    50                  55                  60

Ala Asp Ala Gly Gly Arg Tyr Leu Tyr Val Asn Asp Gly Gly Asp Val
65                  70                  75                  80

Trp Thr Pro Ser Trp Leu Pro Val Lys Ala Asp Leu Asp His Phe Glu
                85                  90                  95

Ala Arg His Gly Leu Gly Tyr Ser Thr Ile Thr Gly Glu Arg Asn Gly
            100                 105                 110

-continued

```
Val Arg Val Glu Thr Leu Phe Phe Val Pro Val Gly Glu Asn Ala Glu
            115                 120                 125

Val Gln Lys Val Thr Val Thr Asn Thr Ser Asp Ser Tyr Lys Ser Leu
            130                 135                 140

Thr Leu Phe Ser Phe Val Glu Phe Cys Leu Trp Asn Ala Gln Asp Asp
145                 150                 155                 160

Met Thr Asn Tyr Gln Arg Asn Leu Ser Val Gly Val Glu Val Glu
            165                 170                 175

Gln Glu Ser Pro His Gly Ser Ala Ile Tyr His Lys Thr Glu Tyr Arg
            180                 185                 190

Glu Arg Arg Asn His Tyr Ala Val Phe Ala Val Asn Thr Gln Ala Glu
            195                 200                 205

Gly Phe Asp Thr Asp Arg Asp Thr Phe Val Gly Leu Tyr Asn Ser Leu
            210                 215                 220

Gly Glu Ala Ala Val Pro Leu Lys Gly Glu Ser Ala Asn Ser Val Ala
225                 230                 235                 240

Ser Gly Trp Tyr Pro Ile Gly Ser His Ser Val Ala Val Ser Leu Ala
            245                 250                 255

Pro Gly Glu Ser Arg Glu Leu Val Tyr Val Leu Gly Tyr Val Glu Asn
            260                 265                 270

Pro Asp Glu Glu Lys Trp Ala Asp Ala Lys Gln Val Val Asn Lys
            275                 280                 285

Glu Arg Ala His Ala Leu Leu Ser Arg Phe Ala Thr Ser Glu Gln Thr
            290                 295                 300

Asp Ala Ala Phe Ala Ala Leu Lys Asp Tyr Trp Thr Asp Leu Leu Ser
305                 310                 315                 320

Thr Tyr Ser Val Ser Ser Asn Asp Glu Lys Leu Asp Arg Met Val Asn
            325                 330                 335

Ile Trp Asn Gln Tyr Gln Cys Met Val Thr Phe Asn Met Ser Arg Ser
            340                 345                 350

Ala Ser Phe Phe Glu Thr Gly Ile Gly Arg Gly Met Gly Phe Arg Asp
            355                 360                 365

Ser Asn Gln Asp Leu Leu Gly Phe Val His Leu Ile Pro Glu Arg Ala
            370                 375                 380

Arg Glu Arg Ile Ile Asp Ile Ala Ser Thr Gln Phe Ala Asp Gly Ser
385                 390                 395                 400

Ala Tyr His Gln Tyr Gln Pro Leu Thr Lys Arg Gly Asn Asn Asp Ile
            405                 410                 415

Gly Ser Gly Phe Asn Asp Asp Pro Leu Trp Leu Ile Ala Gly Thr Ala
            420                 425                 430

Ala Tyr Ile Lys Glu Thr Gly Asp Phe Ser Ile Leu Asp Glu Pro Val
            435                 440                 445

Pro Phe Asp Asn Glu Pro Gly Ser Glu Val Pro Leu Phe Glu His Leu
450                 455                 460

Thr Arg Ser Phe Glu Phe Thr Val Thr His Arg Gly Pro His Gly Leu
465                 470                 475                 480

Pro Leu Ile Gly Arg Ala Asp Trp Asn Asp Cys Leu Asn Leu Asn Cys
            485                 490                 495

Phe Ser Thr Thr Pro Gly Glu Ser Phe Gln Thr Thr Glu Asn Gln Ala
            500                 505                 510

Gly Gly Val Ala Glu Ser Thr Phe Ile Ala Ala Gln Phe Val Leu Tyr
            515                 520                 525

Gly Glu Gln Tyr Ala Glu Leu Ala Ala Arg Arg Gly Leu Ala Asp Val
```

```
                530                 535                 540
Ala Asp Arg Ala Arg Gly His Val Ala Glu Met Arg Asp Ala Leu Leu
545                 550                 555                 560

Thr Asp Gly Trp Asp Gly Ser Trp Phe Leu Arg Ala Tyr Asp Tyr Tyr
                565                 570                 575

Gly Asn Pro Ile Gly Thr Asp Ala His Asp Glu Gly Lys Ile Trp Ile
                580                 585                 590

Glu Pro Gln Gly Phe Ala Val Met Ala Gly Val Gly Val Gly Glu Gly
                595                 600                 605

Pro Gln Asp Thr Asp Ala Pro Ala Ile Lys Ala Leu Asp Ser Val Asn
                610                 615                 620

Glu Met Leu Ala Thr Asp His Gly Met Val Leu Gln Tyr Pro Ala Tyr
625                 630                 635                 640

Thr Thr Tyr Gln Val His Met Gly Glu Val Ser Thr Tyr Pro Pro Gly
                645                 650                 655

Tyr Lys Glu Asn Gly Gly Ile Phe Cys His Asn Asn Pro Trp Val Ile
                660                 665                 670

Ile Ala Glu Thr Val Val Gly Arg Gly Gly Arg Ala Phe Asp Tyr Tyr
                675                 680                 685

Lys Arg Ile Thr Pro Ala Tyr Arg Glu Asp Ile Ser Asp Val His Arg
                690                 695                 700

Thr Glu Pro Tyr Val Tyr Ala Gln Met Ile Ala Gly Lys Glu Ala Val
705                 710                 715                 720

Arg His Gly Glu Ala Lys Asn Ser Trp Leu Thr Gly Thr Ala Ala Trp
                725                 730                 735

Asn Phe Val Thr Val Ser Gln Tyr Leu Leu Gly Val Arg Pro Glu Tyr
                740                 745                 750

Asp Gly Leu Val Val Asp Pro Gln Ile Gly Pro Asp Val Pro Ser Phe
                755                 760                 765

Thr Val Thr Arg Val Ala Arg Gly Ala Thr Tyr Glu Ile Thr Val Thr
                770                 775                 780

Asn Ser Gly Thr Asp Gly Ser Arg Gly Arg Leu Val Val Asp Gly Thr
785                 790                 795                 800

Pro Val Glu Gly Asn Leu Val Pro Tyr Ala Pro Ala Gly Ser Thr Val
                805                 810                 815

Arg Val Asp Val Thr Leu
                820

<210> SEQ ID NO 13
<211> LENGTH: 822
<212> TYPE: PRT
<213> ORGANISM: artificial
<220> FEATURE:
<223> OTHER INFORMATION: modified wildtye sequence

<400> SEQUENCE: 13

Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
                20                  25                  30

Phe Phe Ser Leu Leu Ser His Gln Ala Gly Gly Tyr Ser Phe Tyr Arg
                35                  40                  45

Asp Ala Lys Met Arg Arg Leu Thr Arg Tyr Tyr Asn Asn Ile Pro
50                  55                  60

Ala Asp Ala Gly Gly Arg Tyr Leu Tyr Val Asn Asp Gly Gly Asp Val
```

-continued

```
            65                  70                  75                  80

Trp Thr Pro Ser Trp Leu Pro Val Lys Ala Asp Leu Asp His Phe Glu
                        85                  90                  95

Ala Arg His Gly Leu Gly Tyr Ser Thr Ile Thr Gly Glu Arg Asn Gly
                       100                 105                 110

Val Arg Val Glu Thr Leu Phe Phe Val Pro Val Gly Glu Asn Ala Glu
                       115                 120                 125

Val Gln Lys Val Thr Val Thr Asn Thr Ser Asp Ser Tyr Lys Ser Leu
                       130                 135                 140

Thr Leu Phe Ser Phe Val Glu Phe Cys Leu Trp Asn Ala Gln Asp Asp
        145                 150                 155                 160

Met Thr Asn Tyr Gln Arg Asn Leu Ser Ile Gly Glu Val Glu Val Glu
                       165                 170                 175

Gln Glu Ser Pro His Gly Ser Ala Ile Tyr His Lys Thr Glu Tyr Arg
                       180                 185                 190

Glu Arg Arg Asn His Tyr Ala Val Phe Ala Val Asn Thr Gln Ala Glu
                       195                 200                 205

Gly Phe Asp Thr Asp Arg Asp Thr Phe Val Gly Leu Tyr Asn Ser Leu
                       210                 215                 220

Gly Glu Ala Ala Val Pro Leu Lys Gly Glu Ser Ala Asn Ser Val Ala
        225                 230                 235                 240

Ser Gly Trp Tyr Pro Ile Gly Ser His Ser Val Ala Val Ser Leu Ala
                       245                 250                 255

Pro Gly Glu Ser Arg Glu Leu Val Tyr Val Leu Gly Tyr Val Glu Asn
                       260                 265                 270

Pro Asp Glu Glu Lys Trp Ala Asp Ala Ala Gln Val Val Asn Lys
                       275                 280                 285

Glu Arg Ala His Ala Leu Leu Ser Arg Phe Ala Thr Ser Glu Gln Thr
                       290                 295                 300

Asp Ala Ala Phe Ala Ala Leu Lys Asp Tyr Trp Thr Asp Leu Leu Ser
        305                 310                 315                 320

Thr Tyr Ser Val Ser Ser Asn Asp Glu Lys Leu Asp Arg Met Val Asn
                       325                 330                 335

Ile Trp Asn Gln Tyr Gln Cys Met Val Thr Phe Asn Met Ser Arg Ser
                       340                 345                 350

Ala Ser Phe Phe Glu Thr Gly Ile Gly Arg Gly Met Gly Phe Arg Asp
                       355                 360                 365

Ser Asn Gln Asp Leu Leu Gly Phe Val His Leu Ile Pro Glu Arg Ala
                       370                 375                 380

Arg Glu Arg Ile Ile Asp Ile Ala Ser Thr Gln Phe Ala Asp Gly Ser
        385                 390                 395                 400

Ala Tyr His Gln Tyr Gln Pro Leu Thr Lys Arg Gly Asn Asn Asp Ile
                       405                 410                 415

Gly Ser Gly Phe Asn Asp Asp Pro Leu Trp Leu Ile Ala Gly Thr Ala
                       420                 425                 430

Ala Tyr Ile Lys Glu Thr Gly Asp Phe Ser Ile Leu Asp Glu Pro Val
                       435                 440                 445

Pro Phe Asp Asn Glu Pro Gly Ser Glu Val Pro Leu Phe Glu His Leu
                       450                 455                 460

Thr Arg Ser Phe Glu Phe Thr Val Thr His Arg Gly Pro His Gly Leu
        465                 470                 475                 480

Pro Leu Ile Gly Arg Ala Asp Trp Asn Asp Cys Leu Asn Leu Asn Cys
                       485                 490                 495
```

-continued

Phe Ser Thr Thr Pro Gly Glu Ser Phe Gln Thr Thr Glu Asn Gln Ala
                500                 505                 510

Gly Gly Val Ala Glu Ser Thr Phe Ile Ala Ala Gln Phe Val Leu Tyr
        515                 520                 525

Gly Glu Gln Tyr Ala Glu Leu Ala Ala Arg Arg Gly Leu Ala Asp Val
    530                 535                 540

Ala Asp Arg Ala Arg Gly His Val Ala Glu Met Arg Asp Ala Leu Leu
545                 550                 555                 560

Thr Asp Gly Trp Asp Gly Ser Trp Phe Leu Arg Ala Tyr Asp Tyr Tyr
                565                 570                 575

Gly Asn Pro Ile Gly Thr Asp Ala His Asp Glu Gly Lys Ile Trp Ile
            580                 585                 590

Glu Pro Gln Gly Phe Ala Val Met Ala Gly Val Gly Val Gly Glu Gly
        595                 600                 605

Pro Gln Asp Thr Asp Ala Pro Ala Ile Lys Ala Leu Asp Ser Val Asn
    610                 615                 620

Glu Met Leu Ala Thr Asp His Gly Met Val Leu Gln Tyr Pro Ala Tyr
625                 630                 635                 640

Thr Thr Tyr Gln Val His Met Gly Glu Val Ser Thr Tyr Pro Pro Gly
                645                 650                 655

Tyr Lys Glu Asn Gly Gly Ile Phe Cys His Asn Asn Pro Trp Val Ile
            660                 665                 670

Ile Ala Glu Thr Val Val Gly Arg Gly Gly Arg Ala Phe Asp Tyr Tyr
        675                 680                 685

Lys Arg Ile Thr Pro Ala Tyr Arg Glu Asp Ile Ser Asp Val His Arg
    690                 695                 700

Thr Glu Pro Tyr Val Tyr Ala Gln Met Ile Ala Gly Lys Glu Ala Val
705                 710                 715                 720

Arg His Gly Glu Ala Lys Asn Ser Trp Leu Thr Gly Thr Ala Ala Trp
                725                 730                 735

Asn Phe Val Thr Val Ser Gln Tyr Leu Leu Gly Val Arg Pro Glu Tyr
            740                 745                 750

Asp Gly Leu Val Val Asp Pro Gln Ile Gly Pro Asp Val Pro Ser Phe
        755                 760                 765

Thr Val Thr Arg Val Ala Arg Gly Ala Thr Tyr Glu Ile Thr Val Thr
    770                 775                 780

Asn Ser Gly Thr Asp Gly Ser Arg Gly Arg Leu Val Val Asp Gly Thr
785                 790                 795                 800

Pro Val Glu Gly Asn Leu Val Pro Tyr Ala Pro Ala Gly Ser Thr Val
                805                 810                 815

Arg Val Asp Val Thr Leu
            820

<210> SEQ ID NO 14
<211> LENGTH: 822
<212> TYPE: PRT
<213> ORGANISM: artificial
<220> FEATURE:
<223> OTHER INFORMATION: modified wildtye sequence

<400> SEQUENCE: 14

Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
            20                  25                  30

```
Phe Phe Ser Leu Leu Ser His Gln Ala Gly Gly Tyr Ser Phe Tyr Arg
             35                  40                  45

Asp Ala Lys Met Arg Arg Leu Thr Arg Tyr Arg Tyr Asn Asn Ile Pro
 50                  55                  60

Ala Asp Ala Gly Gly Arg Tyr Leu Tyr Val Asn Asp Gly Gly Asp Val
 65                  70                  75                  80

Trp Thr Pro Ser Trp Leu Pro Val Lys Ala Asp Leu Asp His Phe Glu
                 85                  90                  95

Ala Arg His Gly Leu Gly Tyr Ser Thr Ile Thr Gly Glu Arg Asn Gly
                100                 105                 110

Val Arg Val Glu Thr Leu Phe Phe Val Pro Val Gly Asn Ala Glu
                115                 120                 125

Val Gln Lys Val Thr Val Thr Asn Thr Ser Asp Ser Tyr Lys Ser Leu
130                 135                 140

Thr Leu Phe Ser Phe Val Glu Phe Cys Leu Trp Asn Ala Gln Asp Asp
145                 150                 155                 160

Met Thr Asn Tyr Gln Arg Asn Leu Ser Ile Gly Glu Val Glu Val Glu
                165                 170                 175

Gln Glu Ser Pro His Gly Ser Ala Ile Tyr His Lys Thr Glu Tyr Arg
                180                 185                 190

Glu Arg Arg Asn His Tyr Ala Val Phe Ala Val Asn Thr Gln Ala Glu
                195                 200                 205

Gly Phe Asp Thr Asp Arg Asp Thr Phe Val Gly Leu Tyr Asn Ser Leu
                210                 215                 220

Gly Glu Ala Ala Val Pro Leu Lys Gly Glu Ser Ala Asn Ser Val Ala
225                 230                 235                 240

Ser Gly Trp Tyr Pro Ile Gly Ser His Ser Val Ala Val Ser Leu Ala
                245                 250                 255

Pro Gly Glu Ser Arg Glu Leu Val Tyr Val Leu Gly Tyr Val Glu Asn
                260                 265                 270

Pro Asp Glu Glu Lys Trp Ala Asp Asp Ala Lys Gln Val Val Asn Lys
                275                 280                 285

Glu Arg Ala His Ala Leu Leu Ser Arg Phe Ala Thr Ser Glu Gln Thr
                290                 295                 300

Asp Ala Ala Phe Ala Ala Leu Lys Asp Tyr Trp Thr Asp Leu Leu Ser
305                 310                 315                 320

Thr Tyr Ser Val Ser Ser Asn Asp Glu Lys Leu Asp Arg Met Val Asn
                325                 330                 335

Ile Trp Asn Gln Tyr Gln Cys Met Val Thr Phe Asn Met Ser Arg Ser
                340                 345                 350

Ala Ser Phe Phe Glu Thr Gly Ile Gly Arg Gly Met Gly Phe Arg Asp
                355                 360                 365

Ser Asn Gln Asp Leu Leu Gly Phe Val His Leu Ile Pro Glu Arg Ala
                370                 375                 380

Arg Glu Arg Ile Ile Asp Ile Ala Ser Thr Gln Phe Ala Asp Gly Ser
385                 390                 395                 400

Ala Tyr His Gln Tyr Gln Pro Leu Thr Lys Arg Gly Asn Asn Asp Ile
                405                 410                 415

Gly Ser Gly Phe Asn Asp Asp Pro Leu Trp Leu Ile Ala Gly Thr Ala
                420                 425                 430

Ala Tyr Ile Lys Glu Thr Gly Asp Phe Ser Ile Leu Asp Glu Pro Val
                435                 440                 445
```

```
Pro Phe Asp Asn Glu Pro Gly Ser Glu Val Pro Leu Phe Glu His Leu
    450                 455                 460

Thr Arg Ser Phe Glu Phe Thr Val Thr His Arg Gly Pro His Gly Leu
465                 470                 475                 480

Pro Leu Ile Gly Arg Ala Asp Trp Asn Asp Cys Leu Asn Leu Asn Cys
                485                 490                 495

Phe Ser Thr Thr Pro Gly Glu Ser Phe Gln Thr Thr Glu Asn Gln Ala
                500                 505                 510

Gly Gly Val Ala Glu Ser Thr Phe Ile Ala Ala Gln Phe Val Leu Tyr
            515                 520                 525

Gly Glu Gln Tyr Ala Glu Leu Ala Ala Arg Arg Gly Leu Ala Asp Val
        530                 535                 540

Ala Asp Arg Ala Arg Gly His Val Ala Glu Met Arg Asp Ala Leu Leu
545                 550                 555                 560

Thr Asp Gly Trp Asp Gly Ser Trp Phe Leu Arg Ala Tyr Asp Tyr Tyr
                565                 570                 575

Gly Asn Pro Ile Gly Thr Asp Ala His Asp Glu Gly Lys Ile Trp Ile
                580                 585                 590

Glu Pro Gln Gly Phe Ala Val Met Ala Gly Val Gly Val Gly Glu Gly
            595                 600                 605

Pro Gln Asp Thr Asp Ala Pro Ala Ile Lys Ala Leu Asp Ser Val Asn
        610                 615                 620

Glu Met Leu Ala Thr Asp His Gly Met Val Leu Gln Tyr Pro Ala Tyr
625                 630                 635                 640

Thr Thr Tyr Gln Val His Met Gly Glu Val Ser Thr Tyr Pro Pro Gly
                645                 650                 655

Tyr Lys Glu Asn Gly Gly Ile Phe Cys His Asn Asn Pro Trp Val Ile
                660                 665                 670

Ile Ala Glu Thr Val Val Gly Arg Gly Arg Ala Phe Asp Tyr Tyr
            675                 680                 685

Lys Arg Ile Thr Pro Ala Tyr Arg Glu Asp Ile Ser Asp Val His Arg
        690                 695                 700

Thr Glu Pro Tyr Val Tyr Ala Gln Met Ile Ala Gly Lys Glu Ala Val
705                 710                 715                 720

Arg His Gly Glu Ala Lys Asn Ser Trp Leu Thr Gly Thr Ala Ala Trp
                725                 730                 735

Asn Phe Val Thr Val Ser Gln Tyr Leu Leu Gly Val Arg Pro Glu Tyr
                740                 745                 750

Asp Gly Leu Val Val Asp Pro Gln Ile Gly Pro Asp Val Pro Ser Phe
            755                 760                 765

Thr Val Thr Arg Val Ala Arg Gly Ala Thr Tyr Glu Ile Thr Val Thr
        770                 775                 780

Asn Ser Gly Val Asp Gly Ser Arg Gly Arg Leu Val Val Asp Gly Thr
785                 790                 795                 800

Pro Val Glu Gly Asn Leu Val Pro Tyr Ala Pro Ala Gly Ser Thr Val
                805                 810                 815

Arg Val Asp Val Thr Leu
                820

<210> SEQ ID NO 15
<211> LENGTH: 822
<212> TYPE: PRT
<213> ORGANISM: artificial
<220> FEATURE:
<223> OTHER INFORMATION: modified wildtye sequence
```

<400> SEQUENCE: 15

Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
            20                  25                  30

Phe Phe Ser Leu Leu Ser His Gln Ala Gly Gly Tyr Ser Phe Tyr Arg
        35                  40                  45

Asp Ala Lys Met Arg Arg Leu Thr Arg Tyr Arg Tyr Asn Asn Ile Pro
    50                  55                  60

Ala Asp Ala Gly Gly Arg Tyr Leu Tyr Val Asn Asp Gly Gly Asp Val
65                  70                  75                  80

Trp Thr Pro Ser Trp Leu Pro Val Lys Ala Asp Leu Asp His Phe Glu
                85                  90                  95

Ala Arg His Gly Leu Gly Tyr Ser Thr Ile Thr Gly Glu Arg Asn Gly
            100                 105                 110

Val Arg Val Glu Thr Leu Phe Phe Val Pro Val Gly Asn Ala Glu
        115                 120                 125

Val Gln Lys Val Thr Val Thr Asn Thr Ser Asp Ser Tyr Lys Ser Leu
130                 135                 140

Thr Leu Phe Ser Phe Val Glu Phe Cys Leu Trp Asn Ala Gln Asp Asp
145                 150                 155                 160

Met Thr Asn Tyr Gln Arg Asn Leu Val Ile Gly Glu Val Glu Val Glu
                165                 170                 175

Gln Glu Ser Pro His Gly Ser Ala Ile Tyr His Lys Thr Glu Tyr Arg
            180                 185                 190

Glu Arg Arg Asn His Tyr Ala Val Phe Ala Val Asn Thr Gln Ala Glu
        195                 200                 205

Gly Phe Asp Thr Asp Arg Asp Thr Phe Val Gly Leu Tyr Asn Ser Leu
    210                 215                 220

Gly Glu Ala Ala Val Pro Leu Lys Gly Glu Ser Ala Asn Ser Val Ala
225                 230                 235                 240

Ser Gly Trp Tyr Pro Ile Gly Ser His Ser Val Ala Val Ser Leu Ala
                245                 250                 255

Pro Gly Glu Ser Arg Glu Leu Val Tyr Val Leu Gly Tyr Val Glu Asn
            260                 265                 270

Pro Asp Glu Glu Lys Trp Ala Asp Asp Ala Lys Gln Val Val Asn Lys
        275                 280                 285

Glu Arg Ala His Ala Leu Leu Ser Arg Phe Ala Thr Ser Glu Gln Thr
    290                 295                 300

Asp Ala Ala Phe Ala Ala Leu Lys Asp Tyr Trp Thr Asp Leu Leu Ser
305                 310                 315                 320

Thr Tyr Ser Val Ser Ser Asn Asp Glu Lys Leu Asp Arg Met Val Asn
                325                 330                 335

Ile Trp Asn Gln Tyr Gln Cys Met Val Thr Phe Asn Met Ser Arg Ser
            340                 345                 350

Ala Ser Phe Phe Glu Thr Gly Ile Gly Arg Gly Met Gly Phe Arg Asp
        355                 360                 365

Ser Asn Gln Asp Leu Leu Gly Phe Val His Leu Ile Pro Glu Arg Ala
    370                 375                 380

Arg Glu Arg Ile Ile Asp Ile Ala Ser Thr Gln Phe Ala Asp Gly Ser
385                 390                 395                 400

Ala Tyr His Gln Tyr Gln Pro Leu Thr Lys Arg Gly Asn Asn Asp Ile

```
                405                 410                 415
Gly Ser Gly Phe Asn Asp Asp Pro Leu Trp Leu Ile Ala Gly Thr Ala
            420                 425                 430
Ala Tyr Ile Lys Glu Thr Gly Asp Phe Ser Ile Leu Asp Glu Pro Val
            435                 440                 445
Pro Phe Asp Asn Glu Pro Gly Ser Glu Val Pro Leu Phe Glu His Leu
450                 455                 460
Thr Arg Ser Phe Glu Phe Thr Val Thr His Arg Gly Pro His Gly Leu
465                 470                 475                 480
Pro Leu Ile Gly Arg Ala Asp Trp Asn Asp Cys Leu Asn Leu Asn Cys
            485                 490                 495
Phe Ser Thr Thr Pro Gly Glu Ser Phe Gln Thr Thr Glu Asn Gln Ala
            500                 505                 510
Gly Gly Val Ala Glu Ser Thr Phe Ile Ala Ala Gln Phe Val Leu Tyr
            515                 520                 525
Gly Glu Gln Tyr Ala Glu Leu Ala Ala Arg Arg Gly Leu Ala Asp Val
            530                 535                 540
Ala Asp Arg Ala Arg Gly His Val Ala Glu Met Arg Asp Ala Leu Leu
545                 550                 555                 560
Thr Asp Gly Trp Asp Gly Ser Trp Phe Leu Arg Ala Tyr Asp Tyr Tyr
            565                 570                 575
Gly Asn Pro Ile Gly Thr Asp Glu His Asp Glu Gly Lys Ile Trp Ile
            580                 585                 590
Glu Pro Gln Gly Phe Ala Val Met Ala Gly Val Gly Val Gly Glu Gly
            595                 600                 605
Pro Gln Asp Thr Asp Ala Pro Ala Ile Lys Ala Leu Asp Ser Val Asn
            610                 615                 620
Glu Met Leu Ala Thr Asp His Gly Met Val Leu Gln Tyr Pro Ala Tyr
625                 630                 635                 640
Thr Thr Tyr Gln Val His Met Gly Glu Val Ser Thr Tyr Pro Pro Gly
            645                 650                 655
Tyr Lys Glu Asn Gly Gly Ile Phe Cys His Asn Asn Pro Trp Val Ile
            660                 665                 670
Ile Ala Glu Thr Val Val Gly Arg Gly Gly Arg Ala Phe Asp Tyr Tyr
            675                 680                 685
Lys Arg Ile Thr Pro Ala Tyr Arg Glu Asp Ile Ser Asp Val His Arg
            690                 695                 700
Leu Glu Pro Tyr Val Tyr Ala Gln Met Ile Ala Gly Lys Glu Ala Val
705                 710                 715                 720
Arg His Gly Glu Ala Lys Asn Ser Trp Leu Thr Gly Thr Ala Ala Trp
            725                 730                 735
Asn Phe Val Thr Val Ser Gln Tyr Leu Leu Gly Val Arg Pro Glu Tyr
            740                 745                 750
Asp Gly Leu Val Val Asp Pro Gln Ile Gly Pro Asp Val Pro Ser Phe
            755                 760                 765
Thr Val Thr Arg Val Ala Arg Gly Ala Thr Tyr Glu Ile Thr Val Thr
            770                 775                 780
Asn Ser Gly Thr Asp Gly Ser Arg Gly Arg Leu Val Val Asp Gly Thr
785                 790                 795                 800
Pro Val Glu Gly Asn Leu Val Pro Tyr Ala Pro Ala Gly Ser Thr Val
            805                 810                 815
Arg Val Asp Val Thr Leu
            820
```

```
<210> SEQ ID NO 16
<211> LENGTH: 822
<212> TYPE: PRT
<213> ORGANISM: artificial
<220> FEATURE:
<223> OTHER INFORMATION: modified wildtye sequence

<400> SEQUENCE: 16

Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
            20                  25                  30

Phe Phe Ser Leu Leu Ser His Gln Ala Gly Gly Tyr Ser Phe Tyr Arg
        35                  40                  45

Asp Ala Lys Met Arg Arg Leu Thr Arg Tyr Arg Tyr Asn Asn Ile Pro
50                  55                  60

Ala Asp Ala Gly Gly Arg Tyr Leu Tyr Val Asn Asp Gly Gly Asp Val
65                  70                  75                  80

Trp Thr Pro Ser Trp Leu Pro Val Lys Ala Asp Leu Asp His Phe Glu
                85                  90                  95

Ala Arg His Gly Leu Gly Tyr Ser Thr Ile Thr Gly Glu Arg Asn Gly
            100                 105                 110

Val Arg Val Glu Thr Leu Phe Phe Val Pro Val Gly Asn Ala Glu
        115                 120                 125

Val Gln Lys Val Thr Val Thr Asn Thr Ser Asp Ser Tyr Lys Ser Leu
130                 135                 140

Thr Leu Phe Ser Phe Val Glu Phe Cys Leu Trp Asn Ala Gln Asp Asp
145                 150                 155                 160

Met Thr Asn Tyr Gln Arg Asn Leu Ser Thr Gly Glu Val Glu Val Glu
                165                 170                 175

Gln Glu Ser Pro His Gly Ser Ala Ile Tyr His Lys Thr Glu Tyr Arg
            180                 185                 190

Glu Arg Arg Asn His Tyr Ala Val Phe Ala Val Asn Thr Gln Ala Glu
        195                 200                 205

Gly Phe Asp Thr Asp Arg Asp Thr Phe Val Gly Leu Tyr Asn Ser Leu
210                 215                 220

Gly Glu Ala Ala Val Pro Leu Lys Gly Glu Ser Ala Asn Ser Val Ala
225                 230                 235                 240

Ser Gly Trp Tyr Pro Ile Gly Ser His Ser Val Ala Val Ser Leu Ala
                245                 250                 255

Pro Gly Glu Ser Arg Glu Leu Val Tyr Val Leu Gly Tyr Val Glu Asn
            260                 265                 270

Pro Asp Glu Glu Lys Trp Ala Asp Ala Lys Gln Val Val Asn Lys
        275                 280                 285

Glu Arg Ala His Ala Leu Leu Ser Arg Phe Ala Thr Ser Glu Gln Thr
        290                 295                 300

Asp Ala Ala Phe Ala Ala Leu Lys Asp Tyr Trp Thr Asp Leu Leu Ser
305                 310                 315                 320

Thr Tyr Ser Val Ser Ser Asn Asp Glu Lys Leu Asp Arg Met Val Asn
                325                 330                 335

Ile Trp Asn Gln Tyr Gln Cys Met Val Thr Phe Asn Met Ser Arg Ser
            340                 345                 350

Ala Ser Phe Phe Glu Thr Gly Ile Gly Arg Gly Met Gly Phe Arg Asp
        355                 360                 365
```

```
Ser Asn Gln Asp Leu Leu Gly Phe Val His Leu Ile Pro Glu Arg Ala
    370                 375                 380

Arg Glu Arg Ile Ile Asp Ile Ala Ser Thr Gln Phe Ala Asp Gly Ser
385                 390                 395                 400

Ala Tyr His Gln Tyr Gln Pro Leu Thr Lys Arg Gly Asn Asn Asp Ile
            405                 410                 415

Gly Ser Gly Phe Asn Asp Asp Pro Leu Trp Leu Ile Ala Gly Thr Ala
                420                 425                 430

Ala Tyr Ile Lys Glu Thr Gly Asp Phe Ser Ile Leu Asp Glu Pro Val
            435                 440                 445

Pro Phe Asp Asn Glu Pro Gly Ser Glu Val Pro Leu Phe Glu His Leu
450                 455                 460

Thr Arg Ser Phe Glu Phe Thr Val Thr His Arg Gly Pro His Gly Leu
465                 470                 475                 480

Pro Leu Ile Gly Arg Ala Asp Trp Asn Asp Cys Leu Asn Leu Asn Cys
                485                 490                 495

Phe Ser Thr Thr Pro Gly Glu Ser Phe Gln Thr Thr Glu Asn Gln Ala
                500                 505                 510

Gly Gly Val Ala Glu Ser Thr Phe Ile Ala Ala Gln Phe Val Leu Tyr
            515                 520                 525

Gly Glu Gln Tyr Ala Glu Leu Ala Ala Arg Arg Gly Leu Ala Asp Val
530                 535                 540

Ala Asp Arg Ala Arg Gly His Val Ala Glu Met Arg Asp Ala Leu Leu
545                 550                 555                 560

Thr Asp Gly Trp Asp Gly Ser Trp Phe Leu Arg Ala Tyr Asp Tyr Tyr
                565                 570                 575

Gly Asn Pro Ile Gly Thr Asp Ala His Asp Glu Gly Lys Ile Trp Ile
            580                 585                 590

Glu Pro Gln Gly Phe Ala Val Met Ala Gly Val Gly Val Gly Glu Gly
                595                 600                 605

Pro Gln Asp Thr Asp Ala Pro Ala Ile Lys Ala Leu Asp Ser Val Asn
610                 615                 620

Glu Met Leu Ala Thr Asp His Gly Met Val Leu Gln Tyr Pro Ala Tyr
625                 630                 635                 640

Thr Thr Tyr Gln Val His Met Gly Glu Val Ser Thr Tyr Pro Pro Gly
                645                 650                 655

Tyr Lys Glu Asn Gly Gly Ile Phe Cys His Asn Asn Pro Trp Val Ile
            660                 665                 670

Ile Ala Glu Thr Val Val Gly Arg Gly Arg Ala Phe Asp Tyr Tyr
            675                 680                 685

Lys Arg Ile Thr Pro Ala Tyr Arg Glu Asp Ile Ser Asp Val His Arg
            690                 695                 700

Thr Glu Pro Tyr Val Tyr Ala Gln Met Ile Ala Gly Lys Glu Ala Val
705                 710                 715                 720

Arg His Gly Glu Ala Lys Asn Ser Trp Leu Thr Gly Thr Ala Ala Trp
                725                 730                 735

Asn Phe Val Thr Val Ser Gln Tyr Leu Leu Gly Val Arg Pro Glu Tyr
                740                 745                 750

Asp Gly Leu Val Val Asp Pro Gln Ile Gly Pro Asp Val Pro Ser Phe
            755                 760                 765

Thr Val Thr Arg Val Ala Arg Gly Ala Thr Tyr Glu Ile Thr Val Thr
770                 775                 780
```

-continued

Asn Ser Gly Thr Asp Gly Ser Arg Gly Arg Leu Val Val Asp Gly Thr
785                 790                 795                 800

Pro Val Glu Gly Asn Leu Val Pro Tyr Ala Pro Ala Gly Ser Thr Val
            805                 810                 815

Arg Val Asp Val Thr Leu
            820

<210> SEQ ID NO 17
<211> LENGTH: 822
<212> TYPE: PRT
<213> ORGANISM: artificial
<220> FEATURE:
<223> OTHER INFORMATION: modified wildtye sequence

<400> SEQUENCE: 17

Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
            20                  25                  30

Phe Phe Ser Leu Leu Ser His Gln Ala Gly Gly Tyr Ser Phe Tyr Arg
        35                  40                  45

Asp Ala Lys Met Arg Arg Leu Thr Arg Tyr Arg Tyr Asn Asn Ile Pro
50                  55                  60

Ala Asp Ala Gly Gly Arg Tyr Leu Tyr Val Asn Asp Gly Gly Asp Val
65                  70                  75                  80

Trp Thr Pro Ser Trp Leu Pro Val Lys Ala Asp Leu Asp His Phe Glu
                85                  90                  95

Ala Arg His Gly Leu Gly Tyr Ser Thr Ile Thr Gly Glu Arg Asn Gly
            100                 105                 110

Val Arg Val Glu Thr Leu Phe Phe Val Pro Val Gly Glu Asn Ala Glu
        115                 120                 125

Val Gln Lys Val Thr Val Thr Asn Thr Ser Asp Ser Tyr Lys Ser Leu
130                 135                 140

Thr Leu Phe Ser Phe Val Glu Phe Cys Leu Trp Asn Ala Gln Asp Asp
145                 150                 155                 160

Met Thr Asn Tyr Gln Arg Asn Leu Ser Ile Gly Glu Val Glu Val Glu
                165                 170                 175

Gln Glu Ser Pro His Gly Ser Ala Ile Tyr His Lys Thr Glu Tyr Arg
            180                 185                 190

Glu Arg Arg Asn His Tyr Ala Val Phe Ala Val Asn Thr Gln Ala Glu
        195                 200                 205

Gly Phe Asp Thr Asp Arg Asp Thr Phe Val Gly Leu Tyr Asn Ser Leu
210                 215                 220

Gly Glu Ala Ala Val Pro Leu Lys Gly Glu Ser Ala Asn Ser Val Ala
225                 230                 235                 240

Ser Gly Trp Tyr Pro Ile Gly Ser His Ser Val Ala Val Ser Leu Ala
                245                 250                 255

Pro Gly Glu Ser Arg Glu Leu Val Tyr Val Leu Gly Tyr Val Glu Asn
            260                 265                 270

Pro Asp Glu Glu Lys Trp Ala Asp Ala Lys Gln Val Val Asn Lys
        275                 280                 285

Glu Arg Ala His Ala Leu Leu Ser Arg Phe Ala Thr Ser Glu Gln Thr
290                 295                 300

Asp Ala Ala Phe Ala Ala Leu Lys Asp Tyr Trp Thr Asp Leu Leu Ser
305                 310                 315                 320

```
Thr Tyr Ser Val Ser Ser Asn Asp Glu Lys Leu Asp Arg Met Val Asn
            325                 330                 335

Ile Trp Asn Gln Tyr Gln Cys Met Val Thr Phe Asn Met Ser Arg Ser
        340                 345                 350

Ala Ser Phe Ile Glu Thr Gly Ile Gly Arg Gly Met Gly Phe Arg Asp
    355                 360                 365

Ser Asn Gln Asp Leu Leu Gly Phe Val His Leu Ile Pro Glu Arg Ala
370                 375                 380

Arg Glu Arg Ile Ile Asp Ile Ala Ser Thr Gln Phe Ala Asp Gly Ser
385                 390                 395                 400

Ala Tyr His Gln Tyr Gln Pro Leu Thr Lys Arg Gly Asn Asn Asp Ile
                405                 410                 415

Gly Ser Gly Phe Asn Asp Pro Leu Trp Leu Ile Ala Gly Thr Ala
                420                 425                 430

Ala Tyr Ile Lys Glu Thr Gly Asp Phe Ser Ile Leu Asp Glu Pro Val
        435                 440                 445

Pro Phe Asp Asn Glu Pro Gly Ser Glu Val Pro Leu Phe Glu His Leu
    450                 455                 460

Thr Arg Ser Phe Glu Phe Thr Val Thr His Arg Gly Pro His Gly Leu
465                 470                 475                 480

Pro Leu Ile Gly Arg Ala Asp Trp Asn Asp Cys Leu Asn Leu Asn Cys
                485                 490                 495

Phe Ser Thr Thr Pro Gly Glu Ser Phe Gln Thr Thr Glu Asn Gln Val
                500                 505                 510

Gly Gly Val Ala Glu Ser Thr Phe Ile Ala Ala Gln Phe Val Leu Tyr
                515                 520                 525

Gly Glu Gln Tyr Ala Glu Leu Ala Ala Arg Arg Gly Leu Ala Asp Val
        530                 535                 540

Ala Asp Arg Ala Arg Gly His Val Ala Glu Met Arg Asp Ala Leu Leu
545                 550                 555                 560

Thr Asp Gly Trp Asp Gly Ser Trp Phe Leu Arg Ala Tyr Asp Tyr Tyr
                565                 570                 575

Gly Asn Pro Ile Gly Thr Asp Ala His Asp Glu Gly Lys Ile Trp Ile
                580                 585                 590

Glu Pro Gln Gly Phe Ala Val Met Ala Gly Val Gly Val Gly Glu Gly
        595                 600                 605

Pro Gln Asp Thr Asp Ala Pro Ala Ile Lys Ala Leu Asp Ser Val Asn
    610                 615                 620

Glu Met Leu Ala Thr Asp His Gly Met Val Leu Gln Tyr Pro Ala Tyr
625                 630                 635                 640

Thr Thr Tyr Gln Val His Met Gly Glu Val Ser Thr Tyr Pro Pro Gly
                645                 650                 655

Tyr Lys Glu Asn Gly Gly Ile Phe Cys His Asn Asn Pro Trp Val Ile
                660                 665                 670

Ile Ala Glu Thr Val Val Gly Arg Gly Arg Ala Phe Asp Tyr Tyr
        675                 680                 685

Lys Arg Ile Thr Pro Ala Tyr Arg Glu Asp Ile Ser Asp Val His Arg
    690                 695                 700

Leu Glu Pro Tyr Val Tyr Ala Gln Met Ile Ala Gly Lys Glu Ala Val
705                 710                 715                 720

Arg His Gly Glu Ala Lys Asn Ser Trp Leu Thr Gly Thr Ala Ala Trp
                725                 730                 735

Asn Phe Val Thr Val Ser Gln Tyr Leu Leu Gly Val Arg Pro Glu Tyr
```

```
                    740                 745                 750
Asp Gly Leu Val Val Asp Pro Gln Ile Gly Pro Asp Val Pro Ser Phe
            755                 760                 765

Thr Val Thr Arg Val Ala Arg Gly Ala Thr Tyr Glu Ile Thr Val Thr
        770                 775                 780

Asn Ser Gly Val Asp Gly Ser Arg Gly Arg Leu Val Val Asp Gly Thr
785                 790                 795                 800

Pro Val Glu Gly Asn Leu Val Pro Tyr Ala Pro Ala Gly Ser Thr Val
            805                 810                 815

Arg Val Asp Val Thr Leu
            820

<210> SEQ ID NO 18
<211> LENGTH: 822
<212> TYPE: PRT
<213> ORGANISM: artificial
<220> FEATURE:
<223> OTHER INFORMATION: modified wildtye sequence

<400> SEQUENCE: 18

Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
            20                  25                  30

Phe Phe Ser Leu Leu Ser His Gln Ala Gly Gly Tyr Ser Phe Tyr Arg
        35                  40                  45

Asp Ala Lys Met Arg Arg Leu Thr Arg Tyr Arg Tyr Asn Asn Ile Pro
    50                  55                  60

Ala Asp Ala Gly Gly Arg Tyr Leu Tyr Val Asn Asp Gly Gly Asp Val
65                  70                  75                  80

Trp Thr Pro Ser Trp Leu Pro Val Lys Ala Asp Leu Asp His Phe Glu
            85                  90                  95

Ala Arg His Gly Leu Gly Tyr Ser Thr Ile Thr Gly Glu Arg Asn Gly
        100                 105                 110

Val Arg Val Glu Thr Leu Phe Phe Val Pro Val Gly Glu Asn Ala Glu
    115                 120                 125

Val Gln Lys Val Thr Val Thr Asn Thr Ser Asp Ser Tyr Lys Ser Leu
130                 135                 140

Thr Leu Phe Ser Phe Val Glu Phe Cys Leu Trp Asn Ala Gln Asp Asp
145                 150                 155                 160

Met Thr Asn Phe Gln Arg Asn Leu Ser Ile Gly Glu Val Glu Val Glu
            165                 170                 175

Gln Glu Ser Pro His Gly Ser Ala Ile Tyr His Lys Thr Glu Tyr Arg
        180                 185                 190

Glu Arg Arg Asn His Tyr Ala Val Phe Ala Val Asn Thr Gln Ala Glu
    195                 200                 205

Gly Phe Asp Thr Asp Arg Asp Thr Phe Val Gly Leu Tyr Asn Ser Leu
210                 215                 220

Gly Glu Ala Ala Val Pro Leu Lys Gly Glu Ser Ala Asn Ser Val Ala
225                 230                 235                 240

Ser Gly Trp Tyr Pro Ile Gly Ser His Ser Val Ala Val Ser Leu Ala
            245                 250                 255

Pro Gly Glu Ser Arg Glu Leu Val Tyr Val Leu Gly Tyr Val Glu Asn
        260                 265                 270

Pro Asp Glu Glu Lys Trp Ala Asp Asp Ala Ala Gln Val Val Asn Lys
```

```
                    275                 280                 285
Glu Arg Ala His Ala Leu Leu Ser Arg Phe Ala Thr Ser Glu Gln Thr
            290                 295                 300
Asp Ala Ala Phe Ala Ala Leu Lys Asp Tyr Trp Thr Asp Leu Leu Ser
305                 310                 315                 320
Thr Tyr Ser Val Ser Ser Asn Asp Glu Lys Leu Asp Arg Met Val Asn
                325                 330                 335
Ile Trp Asn Gln Tyr Gln Cys Met Val Thr Phe Asn Met Ser Arg Ser
            340                 345                 350
Ala Ser Phe Phe Glu Thr Gly Ile Gly Arg Gly Met Gly Phe Arg Asp
            355                 360                 365
Ser Asn Gln Asp Leu Leu Gly Phe Val His Leu Ile Pro Glu Arg Ala
    370                 375                 380
Arg Glu Arg Ile Ile Asp Ile Ala Ser Thr Gln Phe Ala Asp Gly Ser
385                 390                 395                 400
Ala Tyr His Gln Tyr Gln Pro Leu Thr Lys Arg Gly Asn Asn Asp Ile
                405                 410                 415
Gly Ser Gly Phe Asn Asp Asp Pro Leu Trp Leu Ile Ala Gly Thr Ala
            420                 425                 430
Ala Tyr Ile Lys Glu Thr Gly Asp Phe Ser Ile Leu Asp Glu Pro Val
            435                 440                 445
Pro Phe Asp Asn Glu Pro Gly Ser Glu Val Pro Leu Phe Glu His Leu
    450                 455                 460
Thr Arg Ser Phe Glu Phe Thr Val Thr His Arg Gly Pro His Gly Leu
465                 470                 475                 480
Pro Leu Ile Gly Arg Ala Asp Trp Asn Asp Cys Leu Asn Leu Asn Cys
                485                 490                 495
Phe Ser Thr Thr Pro Gly Glu Ser Phe Gln Thr Thr Glu Asn Gln Val
            500                 505                 510
Gly Gly Val Ala Glu Ser Thr Phe Ile Ala Ala Gln Phe Val Leu Tyr
            515                 520                 525
Gly Glu Gln Tyr Ala Glu Leu Ala Ala Arg Arg Gly Leu Ala Asp Val
    530                 535                 540
Ala Asp Arg Ala Arg Gly His Val Ala Glu Met Arg Asp Ala Leu Leu
545                 550                 555                 560
Thr Asp Gly Trp Asp Gly Ser Trp Phe Leu Arg Ala Tyr Asp Tyr Tyr
                565                 570                 575
Gly Asn Pro Ile Gly Thr Asp Ala His Asp Glu Gly Lys Ile Trp Ile
            580                 585                 590
Glu Pro Gln Gly Phe Ala Val Met Ala Gly Val Gly Val Gly Glu Gly
            595                 600                 605
Pro Gln Asp Thr Asp Ala Pro Ala Ile Lys Ala Leu Asp Ser Val Asn
    610                 615                 620
Glu Met Leu Ala Thr Asp His Gly Met Val Leu Gln Tyr Pro Ala Tyr
625                 630                 635                 640
Thr Thr Tyr Gln Val His Met Gly Glu Val Ser Thr Tyr Pro Pro Gly
                645                 650                 655
Tyr Lys Glu Asn Gly Gly Ile Phe Cys His Asn Asn Pro Trp Val Ile
            660                 665                 670
Ile Ala Glu Thr Val Val Gly Arg Gly Gly Arg Ala Phe Asp Tyr Tyr
            675                 680                 685
Lys Arg Ile Thr Pro Ala Tyr Arg Glu Asp Ile Ser Asp Val His Arg
    690                 695                 700
```

-continued

```
Thr Glu Pro Tyr Val Tyr Ala Gln Met Ile Ala Gly Lys Glu Ala Val
705                 710                 715                 720

Arg His Gly Glu Ala Lys Asn Ser Trp Leu Thr Gly Thr Ala Ala Trp
                725                 730                 735

Asn Phe Val Thr Val Ser Gln Tyr Leu Leu Gly Val Arg Pro Glu Tyr
            740                 745                 750

Asp Gly Leu Val Val Asp Pro Gln Ile Gly Pro Asp Val Pro Ser Phe
        755                 760                 765

Thr Val Thr Arg Val Ala Arg Gly Ala Thr Tyr Glu Ile Thr Val Thr
    770                 775                 780

Asn Ser Gly Thr Asp Gly Ser Arg Gly Arg Leu Val Val Asp Gly Thr
785                 790                 795                 800

Pro Val Glu Gly Asn Leu Val Pro Tyr Ala Pro Ala Gly Ser Thr Val
                805                 810                 815

Arg Val Asp Val Thr Leu
            820

<210> SEQ ID NO 19
<211> LENGTH: 822
<212> TYPE: PRT
<213> ORGANISM: artificial
<220> FEATURE:
<223> OTHER INFORMATION: modified wildtye sequence

<400> SEQUENCE: 19

Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
                20                  25                  30

Phe Phe Ser Leu Leu Ser His Gln Ala Gly Gly Tyr Ser Phe Tyr Arg
            35                  40                  45

Asp Ala Lys Met Arg Arg Leu Thr Arg Tyr Arg Tyr Asn Asn Ile Pro
        50                  55                  60

Ala Asp Ala Gly Gly Arg Tyr Leu Tyr Val Asn Asp Gly Gly Asp Val
65                  70                  75                  80

Trp Thr Pro Ser Trp Leu Pro Val Lys Ala Asp Leu Asp His Phe Glu
                85                  90                  95

Ala Arg His Gly Leu Gly Tyr Ser Thr Ile Thr Gly Glu Arg Asn Gly
            100                 105                 110

Val Arg Val Glu Thr Leu Phe Phe Val Pro Val Gly Glu Asn Ala Glu
        115                 120                 125

Val Gln Lys Val Thr Val Thr Asn Thr Ser Asp Ser Tyr Lys Ser Leu
    130                 135                 140

Thr Leu Phe Ser Phe Val Glu Phe Cys Leu Trp Asn Ala Gln Asp Asp
145                 150                 155                 160

Met Thr Asn Phe Gln Arg Asn Leu Ser Ile Gly Glu Val Glu Val Glu
                165                 170                 175

Gln Glu Ser Pro His Gly Ser Ala Ile Tyr His Lys Thr Glu Tyr Arg
            180                 185                 190

Glu Arg Arg Asn His Tyr Ala Val Phe Ala Val Asn Thr Gln Ala Glu
        195                 200                 205

Gly Phe Asp Thr Asp Arg Asp Thr Phe Val Gly Leu Tyr Asn Ser Leu
    210                 215                 220

Gly Glu Ala Ala Val Pro Leu Lys Gly Glu Ser Ala Asn Ser Val Ala
225                 230                 235                 240
```

```
Ser Gly Trp Tyr Pro Ile Gly Ser His Ser Val Ala Val Ser Leu Ala
            245                 250                 255

Pro Gly Glu Ser Arg Glu Leu Val Tyr Val Leu Gly Tyr Val Glu Asn
        260                 265                 270

Pro Asp Glu Glu Lys Trp Ala Asp Ala Ala Gln Val Val Asn Lys
        275                 280                 285

Glu Arg Ala His Ala Leu Leu Ser Arg Phe Ala Thr Ser Glu Gln Thr
    290                 295                 300

Asp Ala Ala Phe Ala Ala Leu Lys Asp Tyr Trp Thr Asp Leu Leu Ser
305                 310                 315                 320

Thr Tyr Ser Val Ser Ser Asn Asp Glu Lys Leu Asp Arg Met Val Asn
                325                 330                 335

Ile Trp Asn Gln Tyr Gln Cys Met Val Thr Phe Asn Met Ser Arg Ser
            340                 345                 350

Ala Ser Phe Phe Glu Thr Gly Ile Gly Arg Gly Met Gly Phe Arg Asp
        355                 360                 365

Ser Asn Gln Asp Leu Leu Gly Phe Val His Leu Ile Pro Glu Arg Ala
    370                 375                 380

Arg Glu Arg Ile Ile Asp Ile Ala Ser Thr Gln Phe Ala Asp Gly Ser
385                 390                 395                 400

Ala Tyr His Gln Tyr Gln Pro Leu Thr Lys Arg Gly Asn Asn Asp Ile
                405                 410                 415

Gly Ser Gly Phe Asn Asp Asp Pro Leu Trp Leu Ile Ala Gly Thr Ala
            420                 425                 430

Ala Tyr Ile Lys Glu Thr Gly Asp Phe Ser Ile Leu Asp Glu Pro Val
        435                 440                 445

Pro Phe Asp Asn Glu Pro Gly Ser Glu Val Pro Leu Phe Glu His Leu
    450                 455                 460

Thr Arg Ser Phe Glu Phe Thr Val Thr His Arg Gly Pro His Gly Leu
465                 470                 475                 480

Pro Leu Ile Gly Arg Ala Asp Trp Asn Asp Cys Leu Asn Leu Asn Cys
                485                 490                 495

Phe Ser Thr Thr Pro Gly Glu Ser Phe Gln Thr Thr Glu Asn Gln Val
            500                 505                 510

Gly Gly Val Ala Glu Ser Thr Phe Ile Ala Ala Gln Phe Val Leu Tyr
        515                 520                 525

Gly Glu Gln Tyr Ala Glu Leu Ala Ala Arg Arg Gly Leu Ala Asp Val
    530                 535                 540

Ala Asp Arg Ala Arg Gly His Val Ala Glu Met Arg Asp Ala Leu Leu
545                 550                 555                 560

Thr Asp Gly Trp Asp Gly Ser Trp Phe Leu Arg Ala Tyr Asp Tyr Tyr
                565                 570                 575

Gly Asn Pro Ile Gly Thr Asp Ala His Asp Glu Gly Lys Ile Trp Ile
            580                 585                 590

Glu Pro Gln Gly Phe Ala Val Met Ala Gly Val Gly Val Gly Glu Gly
        595                 600                 605

Pro Gln Asp Thr Asp Ala Pro Ala Ile Lys Ala Leu Asp Ser Val Asn
    610                 615                 620

Glu Met Leu Ala Thr Asp His Gly Met Val Leu Gln Tyr Pro Ala Tyr
625                 630                 635                 640

Thr Thr Tyr Gln Val His Met Gly Glu Val Ser Thr Tyr Pro Pro Gly
                645                 650                 655
```

```
Tyr Lys Glu Asn Gly Gly Ile Phe Cys His Asn Asn Pro Trp Val Ile
            660                 665                 670

Ile Ala Glu Thr Val Val Gly Arg Gly Arg Ala Phe Asp Tyr Tyr
675                 680                 685

Lys Arg Ile Thr Pro Ala Tyr Arg Glu Asp Ile Ser Asp Val His Arg
            690                 695                 700

Thr Glu Pro Tyr Val Tyr Ala Gln Met Ile Ala Gly Lys Glu Ala Val
705                 710                 715                 720

Arg His Gly Glu Ala Lys Asn Ser Trp Leu Thr Gly Thr Ala Ala Trp
                725                 730                 735

Asn Phe Val Thr Val Ser Gln Tyr Leu Leu Gly Val Arg Pro Glu Tyr
            740                 745                 750

Asp Gly Leu Val Val Asp Pro Gln Ile Gly Pro Asp Val Pro Ser Phe
            755                 760                 765

Thr Val Thr Arg Val Ala Arg Gly Ala Thr Tyr Glu Ile Thr Val Thr
770                 775                 780

Asn Ser Gly Val Asp Gly Ser Arg Gly Arg Leu Val Val Asp Gly Thr
785                 790                 795                 800

Pro Val Glu Gly Asn Leu Val Pro Tyr Ala Pro Ala Gly Ser Thr Val
                805                 810                 815

Arg Val Asp Val Thr Leu
                820

<210> SEQ ID NO 20
<211> LENGTH: 822
<212> TYPE: PRT
<213> ORGANISM: artificial
<220> FEATURE:
<223> OTHER INFORMATION: modified wildtye sequence

<400> SEQUENCE: 20

Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
            20                  25                  30

Phe Phe Ser Leu Leu Ser His Gln Ala Gly Gly Tyr Ser Phe Tyr Arg
        35                  40                  45

Asp Ala Lys Met Arg Arg Leu Thr Arg Tyr Arg Tyr Asn Asn Ile Pro
50                  55                  60

Ala Asp Ala Gly Gly Arg Tyr Leu Tyr Val Asn Asp Gly Gly Asp Val
65                  70                  75                  80

Trp Thr Pro Ser Trp Leu Pro Val Lys Ala Asp Leu Asp His Phe Glu
                85                  90                  95

Ala Arg His Gly Leu Gly Tyr Ser Thr Ile Thr Gly Glu Arg Asn Gly
            100                 105                 110

Val Arg Val Glu Thr Leu Phe Phe Val Pro Val Gly Glu Asn Ala Glu
        115                 120                 125

Val Gln Lys Val Thr Val Thr Asn Thr Ser Asp Ser Tyr Lys Ser Leu
130                 135                 140

Thr Leu Phe Ser Phe Val Glu Phe Cys Leu Trp Asn Ala Gln Asp Asp
145                 150                 155                 160

Met Thr Asn Tyr Gln Met Asn Leu Ser Ile Gly Glu Val Glu Val Glu
                165                 170                 175

Gln Glu Ser Pro His Gly Ser Ala Ile Tyr His Lys Thr Glu Tyr Arg
            180                 185                 190
```

```
Glu Arg Arg Asn His Tyr Ala Val Phe Ala Val Asn Thr Gln Ala Glu
            195                 200                 205
Gly Phe Asp Thr Asp Arg Asp Thr Phe Val Gly Leu Tyr Asn Ser Leu
    210                 215                 220
Gly Glu Ala Ala Val Pro Leu Lys Gly Glu Ser Ala Asn Ser Val Ala
225                 230                 235                 240
Ser Gly Trp Tyr Pro Ile Gly Ser His Ser Val Ala Val Ser Leu Ala
                245                 250                 255
Pro Gly Glu Ser Arg Glu Leu Val Tyr Val Leu Gly Tyr Val Glu Asn
            260                 265                 270
Pro Asp Glu Glu Lys Trp Ala Asp Ala Ala Gln Val Val Asn Lys
        275                 280                 285
Glu Arg Ala His Ala Leu Leu Ser Arg Phe Ala Thr Ser Glu Gln Thr
    290                 295                 300
Asp Ala Ala Phe Ala Ala Leu Lys Asp Tyr Trp Thr Asp Leu Leu Ser
305                 310                 315                 320
Thr Tyr Ser Val Ser Ser Asn Asp Glu Lys Leu Asp Arg Met Val Asn
                325                 330                 335
Ile Trp Asn Gln Tyr Gln Cys Met Val Thr Phe Asn Met Ser Arg Ser
            340                 345                 350
Ala Ser Phe Phe Glu Thr Gly Ile Gly Arg Gly Met Gly Phe Arg Asp
        355                 360                 365
Ser Asn Gln Asp Leu Leu Gly Phe Val His Leu Ile Pro Glu Arg Ala
    370                 375                 380
Arg Glu Arg Ile Ile Asp Ile Ala Ser Thr Gln Phe Ala Asp Gly Ser
385                 390                 395                 400
Ala Tyr His Gln Tyr Gln Pro Leu Thr Lys Arg Gly Asn Asn Asp Ile
                405                 410                 415
Gly Ser Gly Phe Asn Asp Asp Pro Leu Trp Leu Ile Ala Gly Thr Ala
            420                 425                 430
Ala Tyr Ile Lys Glu Thr Gly Asp Phe Ser Ile Leu Asp Glu Pro Val
        435                 440                 445
Pro Phe Asp Asn Glu Pro Gly Ser Glu Val Pro Leu Phe Glu His Leu
    450                 455                 460
Thr Arg Ser Phe Glu Phe Thr Val Thr His Arg Gly Pro His Gly Leu
465                 470                 475                 480
Pro Leu Ile Gly Arg Ala Asp Trp Asn Asp Cys Leu Asn Leu Asn Cys
                485                 490                 495
Phe Ser Thr Thr Pro Gly Glu Ser Phe Gln Thr Thr Glu Asn Gln Val
            500                 505                 510
Gly Gly Val Ala Glu Ser Thr Phe Ile Ala Ala Gln Phe Val Leu Tyr
        515                 520                 525
Gly Glu Gln Tyr Ala Glu Leu Ala Ala Arg Arg Gly Leu Ala Asp Val
    530                 535                 540
Ala Asp Arg Ala Arg Gly His Val Ala Glu Met Arg Asp Ala Leu Leu
545                 550                 555                 560
Thr Asp Gly Trp Asp Gly Ser Trp Phe Leu Arg Ala Tyr Asp Tyr Tyr
                565                 570                 575
Gly Asn Pro Ile Gly Thr Asp Ala His Asp Glu Gly Lys Ile Trp Ile
            580                 585                 590
Glu Pro Gln Gly Phe Ala Val Met Ala Gly Val Gly Val Gly Glu Gly
        595                 600                 605
Pro Gln Asp Thr Asp Ala Pro Ala Ile Lys Ala Leu Asp Ser Val Asn
```

```
                    610                 615                 620
Glu Met Leu Ala Thr Asp His Gly Met Val Leu Gln Tyr Pro Ala Tyr
625                 630                 635                 640

Thr Thr Tyr Gln Val His Met Gly Glu Val Ser Thr Tyr Pro Pro Gly
                    645                 650                 655

Tyr Lys Glu Asn Gly Gly Ile Phe Cys His Asn Asn Pro Trp Val Ile
                660                 665                 670

Ile Ala Glu Thr Val Val Gly Arg Gly Arg Ala Phe Asp Tyr Tyr
                675                 680                 685

Lys Arg Ile Thr Pro Ala Tyr Arg Glu Asp Ile Ser Asp Val His Arg
                690                 695                 700

Thr Glu Pro Tyr Val Tyr Ala Gln Met Ile Ala Gly Lys Glu Ala Val
705                 710                 715                 720

Arg His Gly Glu Ala Lys Asn Ser Trp Leu Thr Gly Thr Ala Ala Trp
                725                 730                 735

Asn Phe Val Thr Val Ser Gln Tyr Leu Leu Gly Val Arg Pro Glu Tyr
                740                 745                 750

Asp Gly Leu Val Val Asp Pro Gln Ile Gly Pro Asp Val Pro Ser Phe
                755                 760                 765

Thr Val Thr Arg Val Ala Arg Gly Ala Thr Tyr Glu Ile Thr Val Thr
770                 775                 780

Asn Ser Gly Val Asp Gly Ser Arg Gly Arg Leu Val Val Asp Gly Thr
785                 790                 795                 800

Pro Val Glu Gly Asn Leu Val Pro Tyr Ala Pro Ala Gly Ser Thr Val
                805                 810                 815

Arg Val Asp Val Thr Leu
                820

<210> SEQ ID NO 21
<211> LENGTH: 822
<212> TYPE: PRT
<213> ORGANISM: artificial
<220> FEATURE:
<223> OTHER INFORMATION: modified wildtype sequence

<400> SEQUENCE: 21

Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
                20                  25                  30

Phe Phe Ser Leu Leu Ser His Gln Ala Gly Gly Tyr Ser Phe Tyr Arg
            35                  40                  45

Asp Ala Lys Met Arg Arg Leu Thr Arg Tyr Arg Tyr Asn Asn Ile Pro
        50                  55                  60

Ala Asp Ala Gly Gly Arg Tyr Leu Tyr Val Asn Asp Gly Gly Asp Val
65                  70                  75                  80

Trp Thr Pro Ser Trp Leu Pro Val Lys Ala Asp Leu Asp His Phe Glu
                85                  90                  95

Ala Arg His Gly Leu Gly Tyr Ser Thr Ile Thr Gly Glu Arg Asn Gly
            100                 105                 110

Val Arg Val Glu Thr Leu Phe Phe Val Pro Val Gly Glu Asn Ala Glu
        115                 120                 125

Val Gln Lys Val Thr Val Thr Asn Thr Ser Asp Ser Tyr Lys Ser Leu
130                 135                 140

Thr Leu Phe Ser Phe Val Glu Phe Cys Leu Trp Asn Ala Gln Asp Asp
```

```
            145                 150                 155                 160
        Met Thr Asn Tyr Gln Arg Asn Leu Val Ile Gly Glu Val Glu Val Glu
                        165                 170                 175
        Gln Glu Ser Pro His Gly Ser Ala Ile Tyr His Lys Thr Glu Tyr Arg
                        180                 185                 190
        Glu Arg Arg Asn His Tyr Ala Val Phe Ala Val Asn Thr Gln Ala Glu
                        195                 200                 205
        Gly Phe Asp Thr Asp Arg Asp Thr Phe Val Gly Leu Tyr Asn Ser Leu
                        210                 215                 220
        Gly Glu Ala Ala Val Pro Leu Lys Gly Glu Ser Ala Asn Ser Val Ala
        225                 230                 235                 240
        Ser Gly Trp Tyr Pro Ile Gly Ser His Ser Val Ala Val Ser Leu Ala
                        245                 250                 255
        Pro Gly Glu Ser Arg Glu Leu Val Tyr Val Leu Gly Tyr Val Glu Asn
                        260                 265                 270
        Pro Asp Glu Glu Lys Trp Ala Asp Ala Ala Gln Val Val Asn Lys
                        275                 280                 285
        Glu Arg Ala His Ala Leu Leu Ser Arg Phe Ala Thr Ser Glu Gln Thr
                        290                 295                 300
        Asp Ala Ala Phe Ala Ala Leu Lys Asp Tyr Trp Thr Asp Leu Leu Ser
        305                 310                 315                 320
        Thr Tyr Ser Val Ser Ser Asn Asp Glu Lys Leu Asp Arg Met Val Asn
                        325                 330                 335
        Ile Trp Asn Gln Tyr Gln Cys Met Val Thr Phe Asn Met Ser Arg Ser
                        340                 345                 350
        Ala Ser Phe Phe Glu Thr Gly Ile Gly Arg Gly Met Gly Phe Arg Asp
                        355                 360                 365
        Ser Asn Gln Asp Leu Leu Gly Phe Val His Leu Ile Pro Glu Arg Ala
                        370                 375                 380
        Arg Glu Arg Ile Ile Asp Ile Ala Ser Thr Gln Phe Ala Asp Gly Ser
        385                 390                 395                 400
        Ala Tyr His Gln Tyr Gln Pro Leu Thr Lys Arg Gly Asn Asn Asp Ile
                        405                 410                 415
        Gly Ser Gly Phe Asn Asp Asp Pro Leu Trp Leu Ile Ala Gly Thr Ala
                        420                 425                 430
        Ala Tyr Ile Lys Glu Thr Gly Asp Phe Ser Ile Leu Asp Glu Pro Val
                        435                 440                 445
        Pro Phe Asp Asn Glu Pro Gly Ser Glu Val Pro Leu Phe Glu His Leu
                        450                 455                 460
        Thr Arg Ser Phe Glu Phe Thr Val Thr His Arg Gly Pro His Gly Leu
        465                 470                 475                 480
        Pro Leu Ile Gly Arg Ala Asp Trp Asn Asp Cys Leu Asn Leu Asn Cys
                        485                 490                 495
        Phe Ser Thr Thr Pro Gly Glu Ser Phe Gln Thr Thr Glu Asn Gln Val
                        500                 505                 510
        Gly Gly Val Ala Glu Ser Thr Phe Ile Ala Ala Gln Phe Val Leu Tyr
                        515                 520                 525
        Gly Glu Gln Tyr Ala Glu Leu Ala Ala Arg Arg Gly Leu Ala Asp Val
                        530                 535                 540
        Ala Asp Arg Ala Arg Gly His Val Ala Glu Met Arg Asp Ala Leu Leu
        545                 550                 555                 560
        Thr Asp Gly Trp Asp Gly Ser Trp Phe Leu Arg Ala Tyr Asp Tyr Tyr
                        565                 570                 575
```

-continued

```
Gly Asn Pro Ile Gly Thr Asp Ala His Asp Glu Gly Lys Ile Trp Ile
            580                 585                 590
Glu Pro Gln Gly Phe Ala Val Met Ala Gly Val Gly Val Gly Glu Gly
            595                 600                 605
Pro Gln Asp Thr Asp Ala Pro Ala Ile Lys Ala Leu Asp Ser Val Asn
610                 615                 620
Glu Met Leu Ala Thr Asp His Gly Met Val Leu Gln Tyr Pro Ala Tyr
625                 630                 635                 640
Thr Thr Tyr Gln Val His Met Gly Glu Val Ser Thr Tyr Pro Pro Gly
                645                 650                 655
Tyr Lys Glu Asn Gly Gly Ile Phe Cys His Asn Asn Pro Trp Val Ile
            660                 665                 670
Ile Ala Glu Thr Val Val Gly Arg Gly Arg Ala Phe Asp Tyr Tyr
            675                 680                 685
Lys Arg Ile Thr Pro Ala Tyr Arg Glu Asp Ile Ser Asp Val His Arg
            690                 695                 700
Thr Glu Pro Tyr Val Tyr Ala Gln Met Ile Ala Gly Lys Glu Ala Val
705                 710                 715                 720
Arg His Gly Glu Ala Lys Asn Ser Trp Leu Thr Gly Thr Ala Ala Trp
                725                 730                 735
Asn Phe Val Thr Val Ser Gln Tyr Leu Leu Gly Val Arg Pro Glu Tyr
            740                 745                 750
Asp Gly Leu Val Val Asp Pro Gln Ile Gly Pro Asp Val Pro Ser Phe
            755                 760                 765
Thr Val Thr Arg Val Ala Arg Gly Ala Thr Tyr Glu Ile Thr Val Thr
770                 775                 780
Asn Ser Gly Val Asp Gly Ser Arg Gly Arg Leu Val Val Asp Gly Thr
785                 790                 795                 800
Pro Val Glu Gly Asn Leu Val Pro Tyr Ala Pro Ala Gly Ser Thr Val
                805                 810                 815
Arg Val Asp Val Thr Leu
            820

<210> SEQ ID NO 22
<211> LENGTH: 822
<212> TYPE: PRT
<213> ORGANISM: artificial
<220> FEATURE:
<223> OTHER INFORMATION: modified wildtype sequence

<400> SEQUENCE: 22

Met Arg Tyr Gly His Phe Asp Asp Glu Ala Arg Glu Tyr Val Ile Thr
1               5                   10                  15
Thr Pro His Thr Pro Tyr Pro Trp Ile Asn Tyr Leu Gly Ser Glu Gln
            20                  25                  30
Phe Phe Ser Leu Leu Ser His Gln Ala Gly Gly Tyr Ser Phe Tyr Arg
        35                  40                  45
Asp Ala Lys Met Arg Arg Leu Thr Arg Tyr Arg Tyr Asn Asn Ile Pro
    50                  55                  60
Ala Asp Ala Gly Gly Arg Tyr Leu Tyr Val Asn Asp Gly Gly Asp Val
65                  70                  75                  80
Trp Thr Pro Ser Trp Leu Pro Val Lys Ala Asp Leu Asp His Phe Glu
                85                  90                  95
Ala Arg His Gly Leu Gly Tyr Ser Thr Ile Thr Gly Glu Arg Asn Gly
            100                 105                 110
```

```
Val Arg Val Glu Thr Leu Phe Phe Val Pro Val Gly Glu Asn Ala Glu
        115                 120                 125

Val Gln Lys Val Thr Val Thr Asn Thr Ser Asp Ser Tyr Lys Ser Leu
        130                 135                 140

Thr Leu Phe Ser Phe Val Glu Phe Cys Leu Trp Asn Ala Gln Asp Asp
145                 150                 155                 160

Met Thr Asn Tyr Gln Arg Asn Leu Val Ile Gly Glu Val Glu
                165                 170                 175

Gln Glu Ser Pro His Gly Ser Ala Ile Tyr His Lys Thr Glu Tyr Arg
                180                 185                 190

Glu Arg Arg Asn His Tyr Ala Val Phe Ala Val Asn Thr Gln Ala Glu
        195                 200                 205

Gly Phe Asp Thr Asp Arg Asp Thr Phe Val Gly Leu Tyr Asn Ser Leu
        210                 215                 220

Gly Glu Ala Ala Val Pro Leu Lys Gly Glu Ser Ala Asn Ser Val Ala
225                 230                 235                 240

Ser Gly Trp Tyr Pro Ile Gly Ser His Ser Val Ala Val Ser Leu Ala
                245                 250                 255

Pro Gly Glu Ser Arg Glu Leu Val Tyr Val Leu Gly Tyr Val Glu Asn
        260                 265                 270

Pro Asp Glu Glu Lys Trp Ala Asp Ala Ala Gln Val Val Asn Lys
        275                 280                 285

Glu Arg Ala His Ala Leu Leu Ser Arg Phe Ala Thr Ser Glu Gln Thr
        290                 295                 300

Asp Ala Ala Phe Ala Ala Leu Lys Asp Tyr Trp Thr Asp Leu Leu Ser
305                 310                 315                 320

Thr Tyr Ser Val Ser Ser Asn Asp Glu Lys Leu Asp Arg Met Val Asn
                325                 330                 335

Ile Trp Asn Gln Tyr Gln Cys Met Val Thr Phe Asn Met Ser Arg Ser
                340                 345                 350

Ala Ser Phe Phe Glu Thr Gly Ile Gly Arg Gly Met Gly Phe Arg Asp
        355                 360                 365

Ser Asn Gln Asp Leu Leu Gly Phe Val His Leu Ile Pro Glu Arg Ala
        370                 375                 380

Arg Glu Arg Ile Ile Asp Ile Ala Ser Thr Gln Phe Ala Asp Gly Ser
385                 390                 395                 400

Ala Tyr His Gln Tyr Gln Pro Leu Thr Lys Arg Gly Asn Asn Asp Ile
                405                 410                 415

Gly Ser Gly Phe Asn Asp Asp Pro Leu Trp Leu Ile Ala Gly Thr Ala
                420                 425                 430

Ala Tyr Ile Lys Glu Thr Gly Asp Phe Ser Ile Leu Asp Glu Pro Val
                435                 440                 445

Pro Phe Asp Asn Glu Pro Gly Ser Glu Val Pro Leu Phe Glu His Leu
450                 455                 460

Thr Arg Ser Phe Glu Phe Thr Val Glu His Arg Gly Pro His Gly Leu
465                 470                 475                 480

Pro Leu Ile Gly Arg Ala Asp Trp Asn Asp Cys Leu Asn Leu Asn Cys
                485                 490                 495

Phe Ser Thr Thr Pro Gly Glu Ser Phe Gln Thr Thr Glu Asn Gln Val
                500                 505                 510

Gly Gly Val Ala Glu Ser Thr Phe Ile Ala Ala Gln Phe Val Leu Tyr
                515                 520                 525
```

Gly Glu Gln Tyr Ala Glu Leu Ala Ala Arg Arg Gly Leu Ala Asp Val
            530                 535                 540

Ala Asp Arg Ala Arg Gly His Val Ala Glu Met Arg Asp Ala Leu Leu
545                 550                 555                 560

Thr Asp Gly Trp Asp Gly Ser Trp Phe Leu Arg Ala Tyr Asp Tyr Tyr
                565                 570                 575

Gly Asn Pro Ile Gly Thr Asp Ala His Asp Glu Gly Lys Ile Trp Ile
            580                 585                 590

Glu Pro Gln Gly Phe Ala Val Met Ala Gly Val Gly Val Gly Glu Gly
                595                 600                 605

Pro Gln Asp Thr Asp Ala Pro Ala Ile Lys Ala Leu Asp Ser Val Asn
610                 615                 620

Glu Met Leu Ala Thr Asp His Gly Met Val Leu Gln Tyr Pro Ala Tyr
625                 630                 635                 640

Thr Thr Tyr Gln Val His Met Gly Glu Val Ser Thr Tyr Pro Pro Gly
                645                 650                 655

Tyr Lys Glu Asn Gly Gly Ile Phe Cys His Asn Asn Pro Trp Val Ile
            660                 665                 670

Ile Ala Glu Thr Val Val Gly Arg Gly Gly Arg Ala Phe Asp Tyr Tyr
            675                 680                 685

Lys Arg Ile Thr Pro Ala Tyr Arg Glu Asp Ile Ser Asp Val His Arg
690                 695                 700

Thr Glu Pro Tyr Val Tyr Ala Gln Met Ile Ala Gly Lys Glu Ala Val
705                 710                 715                 720

Arg His Gly Glu Ala Lys Asn Ser Trp Leu Thr Gly Thr Ala Ala Trp
                725                 730                 735

Asn Phe Val Thr Val Ser Gln Tyr Leu Leu Gly Val Arg Pro Glu Tyr
            740                 745                 750

Asp Gly Leu Val Val Asp Pro Gln Ile Gly Pro Asp Val Pro Ser Phe
            755                 760                 765

Thr Val Thr Arg Val Ala Arg Gly Ala Thr Tyr Glu Ile Thr Val Thr
770                 775                 780

Asn Ser Gly Val Asp Gly Ser Arg Gly Arg Leu Val Val Asp Gly Thr
785                 790                 795                 800

Pro Val Glu Gly Asn Leu Val Pro Tyr Ala Pro Ala Gly Ser Thr Val
                805                 810                 815

Arg Val Asp Val Thr Leu
            820

<210> SEQ ID NO 23
<211> LENGTH: 822
<212> TYPE: PRT
<213> ORGANISM: artificial
<220> FEATURE:
<223> OTHER INFORMATION: modified wildtype sequence

<400> SEQUENCE: 23

Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
            20                  25                  30

Phe Phe Ser Leu Leu Ser His Gln Ala Gly Gly Tyr Ser Phe Tyr Arg
        35                  40                  45

Asp Ala Lys Met Arg Arg Leu Thr Arg Tyr Arg Tyr Asn Asn Ile Pro
50                  55                  60

```
Ala Asp Ala Gly Gly Arg Tyr Leu Tyr Val Asn Asp Gly Gly Asp Val
 65                  70                  75                  80

Trp Thr Pro Ser Trp Leu Pro Val Lys Ala Asp Leu Asp His Phe Glu
             85                  90                  95

Ala Arg His Gly Leu Gly Tyr Ser Thr Ile Thr Gly Glu Arg Asn Gly
            100                 105                 110

Val Arg Val Glu Thr Leu Phe Phe Val Pro Val Gly Glu Asn Ala Glu
        115                 120                 125

Val Gln Lys Val Thr Val Thr Asn Thr Ser Asp Ser Tyr Lys Ser Leu
    130                 135                 140

Thr Leu Phe Ser Phe Val Glu Phe Cys Leu Trp Asn Ala Gln Asp Asp
145                 150                 155                 160

Met Thr Asn Tyr Gln Arg Asn Leu Val Ile Gly Glu Val Glu Val Glu
                165                 170                 175

Gln Glu Ser Pro His Gly Ser Ala Ile Tyr His Arg Thr Glu Tyr Arg
            180                 185                 190

Glu Arg Arg Asn His Tyr Ala Val Phe Ala Val Asn Thr Gln Ala Glu
        195                 200                 205

Gly Phe Asp Thr Asp Arg Asp Thr Phe Val Gly Leu Tyr Asn Ser Leu
    210                 215                 220

Gly Glu Ala Ala Val Pro Leu Lys Gly Glu Ser Ala Asn Ser Val Ala
225                 230                 235                 240

Ser Gly Trp Tyr Pro Ile Gly Ser His Ser Val Ala Val Ser Leu Ala
                245                 250                 255

Pro Gly Glu Ser Arg Glu Leu Val Tyr Val Leu Gly Tyr Val Glu Asn
            260                 265                 270

Pro Asp Glu Glu Lys Trp Ala Asp Ala Ala Gln Val Val Asn Lys
        275                 280                 285

Glu Arg Ala His Ala Leu Leu Ser Arg Phe Ala Thr Ser Glu Gln Thr
        290                 295                 300

Asp Ala Ala Phe Ala Ala Leu Lys Asp Tyr Trp Thr Asn Leu Leu Ser
305                 310                 315                 320

Thr Tyr Ser Val Ser Ser Asn Asp Glu Lys Leu Asp Arg Met Val Asn
                325                 330                 335

Ile Trp Asn Gln Tyr Gln Cys Met Val Thr Phe Asn Met Ser Arg Ser
            340                 345                 350

Ala Ser Phe Phe Glu Thr Gly Ile Gly Arg Gly Met Gly Phe Arg Asp
        355                 360                 365

Ser Asn Gln Asp Leu Leu Gly Phe Val His Leu Ile Pro Glu Arg Ala
    370                 375                 380

Arg Glu Arg Ile Ile Asp Ile Ala Ser Thr Gln Phe Ala Asp Gly Ser
385                 390                 395                 400

Ala Tyr His Gln Tyr Gln Pro Leu Thr Lys Arg Gly Asn Asn Asp Ile
                405                 410                 415

Gly Ser Gly Phe Asn Asp Asp Pro Leu Trp Leu Ile Ala Gly Thr Ala
            420                 425                 430

Ala Tyr Ile Lys Glu Thr Gly Asp Phe Ser Ile Leu Asp Glu Pro Val
        435                 440                 445

Pro Phe Asp Asn Glu Pro Gly Ser Glu Val Pro Leu Phe Glu His Leu
    450                 455                 460

Thr Arg Ser Phe Glu Phe Thr Val Thr His Arg Gly Pro His Gly Leu
465                 470                 475                 480

Pro Leu Ile Gly Arg Ala Asp Trp Asn Asp Cys Leu Asn Leu Asn Cys
```

```
            485                 490                 495
Phe Ser Thr Thr Pro Gly Glu Ser Phe Gln Thr Thr Glu Asn Gln Val
            500                 505                 510

Gly Gly Val Ala Glu Ser Thr Phe Ile Ala Ala Gln Phe Val Leu Tyr
        515                 520                 525

Gly Glu Gln Tyr Ala Glu Leu Ala Arg Arg Gly Leu Ala Asp Val
    530                 535                 540

Ala Asp Arg Ala Arg Gly His Val Ala Glu Met Arg Asp Ala Leu Leu
545                 550                 555                 560

Thr Asp Gly Trp Asp Gly Ser Trp Phe Leu Arg Ala Tyr Asp Tyr Tyr
                565                 570                 575

Gly Asn Pro Ile Gly Thr Asp Ala His Asp Glu Gly Lys Ile Trp Ile
            580                 585                 590

Glu Pro Gln Gly Phe Ala Val Met Ala Gly Val Gly Val Gly Glu Gly
        595                 600                 605

Pro Gln Asp Thr Asp Ala Pro Ala Ile Lys Ala Leu Asp Ser Val Asn
    610                 615                 620

Glu Met Leu Ala Thr Asp His Gly Met Val Leu Gln Tyr Pro Ala Tyr
625                 630                 635                 640

Thr Thr Tyr Gln Val His Met Gly Glu Val Ser Thr Tyr Pro Pro Gly
                645                 650                 655

Tyr Lys Glu Asn Gly Gly Ile Phe Cys His Asn Asn Pro Trp Val Ile
            660                 665                 670

Ile Ala Glu Thr Val Val Gly Arg Gly Gly Arg Ala Phe Asp Tyr Tyr
        675                 680                 685

Lys Arg Ile Thr Pro Ala Tyr Arg Glu Asp Ile Ser Asp Val His Arg
    690                 695                 700

Thr Glu Pro Tyr Val Tyr Ala Gln Met Ile Ala Gly Lys Glu Ala Val
705                 710                 715                 720

Arg His Gly Glu Ala Lys Asn Ser Trp Leu Thr Gly Thr Ala Ala Trp
                725                 730                 735

Asn Phe Val Thr Val Ser Gln Tyr Leu Leu Gly Val Arg Pro Glu Tyr
            740                 745                 750

Asp Gly Leu Val Val Asp Pro Gln Ile Gly Pro Asp Val Pro Ser Phe
        755                 760                 765

Thr Val Thr Arg Val Ala Arg Gly Ala Thr Tyr Glu Ile Thr Val Thr
    770                 775                 780

Asn Ser Gly Val Asp Gly Ser Arg Gly Arg Leu Val Val Asp Gly Thr
785                 790                 795                 800

Pro Val Glu Gly Asn Leu Val Pro Tyr Ala Pro Ala Gly Ser Thr Val
                805                 810                 815

Arg Val Asp Val Thr Leu
            820

<210> SEQ ID NO 24
<211> LENGTH: 822
<212> TYPE: PRT
<213> ORGANISM: artificial
<220> FEATURE:
<223> OTHER INFORMATION: modified wildtype sequence

<400> SEQUENCE: 24

Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
```

```
                 20                  25                  30
Phe Phe Ser Leu Leu Ser His Gln Ala Gly Gly Tyr Ser Phe Tyr Arg
             35                  40                  45
Asp Ala Lys Met Arg Arg Leu Thr Arg Tyr Arg Tyr Asn Asn Ile Pro
         50                  55                  60
Ala Asp Ala Gly Gly Arg Tyr Leu Tyr Val Asn Asp Gly Gly Asp Val
 65                  70                  75                  80
Trp Thr Pro Ser Trp Leu Pro Val Lys Ala Asp Leu Asp His Phe Glu
                 85                  90                  95
Ala Arg His Gly Leu Gly Tyr Ser Thr Ile Thr Gly Glu Arg Asn Gly
             100                 105                 110
Val Arg Val Glu Thr Leu Phe Phe Val Pro Val Gly Glu Asn Ala Glu
         115                 120                 125
Val Gln Lys Val Thr Val Thr Asn Thr Ser Asp Ser Tyr Lys Ser Leu
     130                 135                 140
Thr Leu Phe Ser Phe Val Glu Phe Cys Leu Trp Asn Ala Gln Asp Asp
145                 150                 155                 160
Met Thr Asn Tyr Gln Arg Asn Leu Val Ile Gly Glu Val Glu Val Glu
                 165                 170                 175
Gln Glu Ser Pro His Gly Ser Ala Ile Tyr His Arg Thr Glu Tyr Arg
             180                 185                 190
Glu Arg Arg Asn His Tyr Ala Val Phe Ala Val Asn Thr Gln Ala Glu
         195                 200                 205
Gly Phe Asp Thr Asp Arg Asp Thr Phe Val Gly Leu Tyr Asn Ser Leu
     210                 215                 220
Gly Glu Ala Ala Val Pro Leu Lys Gly Glu Ser Ala Asn Ser Val Ala
225                 230                 235                 240
Ser Gly Trp Tyr Pro Ile Gly Ser His Ser Val Ala Val Ser Leu Ala
                 245                 250                 255
Pro Gly Glu Ser Arg Glu Leu Val Tyr Val Leu Gly Tyr Val Glu Asn
             260                 265                 270
Pro Asp Glu Glu Lys Trp Ala Asp Ala Ala Gln Val Val Asn Lys
         275                 280                 285
Glu Arg Ala His Ala Leu Leu Ser Arg Phe Ala Thr Ser Glu Gln Thr
     290                 295                 300
Asp Ala Ala Phe Ala Ala Leu Lys Asp Tyr Trp Thr Asp Leu Leu Ser
305                 310                 315                 320
Thr Tyr Ser Val Ser Ser Asn Asp Glu Lys Leu Asp Arg Met Val Asn
                 325                 330                 335
Ile Trp Asn Gln Tyr Gln Cys Met Val Thr Phe Asn Met Ser Arg Ser
             340                 345                 350
Ala Ser Phe Phe Glu Thr Gly Ile Gly Arg Gly Met Gly Phe Arg Asp
         355                 360                 365
Ser Asn Gln Asp Leu Leu Gly Phe Val His Leu Ile Pro Glu Arg Ala
     370                 375                 380
Arg Glu Arg Ile Ile Asp Ile Ala Ser Thr Gln Phe Ala Asp Gly Ser
385                 390                 395                 400
Ala Tyr His Gln Tyr Gln Pro Leu Thr Lys Arg Gly Asn Asn Asp Ile
                 405                 410                 415
Gly Ser Gly Phe Asn Asp Asp Pro Leu Trp Leu Ile Ala Gly Thr Ala
             420                 425                 430
Ala Tyr Ile Lys Glu Thr Gly Asp Phe Ser Ile Leu Asp Glu Pro Val
         435                 440                 445
```

```
Pro Phe Asp Asn Glu Pro Gly Ser Glu Val Pro Leu Phe Glu His Leu
        450                 455                 460

Thr Arg Ser Phe Glu Phe Thr Val Thr His Arg Gly Pro His Gly Leu
465                 470                 475                 480

Pro Leu Ile Gly Arg Ala Asp Trp Asn Asp Cys Leu Asn Leu Asn Cys
                485                 490                 495

Phe Ser Thr Thr Pro Gly Glu Ser Phe Gln Thr Thr Glu Asn Gln Val
                500                 505                 510

Gly Gly Val Ala Glu Ser Thr Phe Ile Ala Ala Gln Phe Val Leu Tyr
            515                 520                 525

Gly Glu Gln Tyr Ala Glu Leu Ala Ala Arg Arg Gly Leu Ala Asp Val
        530                 535                 540

Ala Asp Arg Ala Arg Gly His Val Ala Asn Met Arg Asp Ala Leu Leu
545                 550                 555                 560

Thr Asp Gly Trp Asp Gly Ser Trp Phe Leu Arg Ala Tyr Asp Tyr Tyr
                565                 570                 575

Gly Asn Pro Ile Gly Thr Asp Ala His Asp Glu Gly Lys Ile Trp Ile
                580                 585                 590

Glu Pro Gln Gly Phe Ala Val Met Ala Gly Val Gly Val Gly Glu Gly
        595                 600                 605

Pro Gln Asp Thr Asp Ala Pro Ala Ile Lys Ala Leu Asp Ser Val Asn
610                 615                 620

Glu Met Leu Ala Thr Asp His Gly Met Val Leu Gln Tyr Pro Ala Tyr
625                 630                 635                 640

Thr Thr Tyr Gln Val His Met Gly Glu Val Ser Thr Tyr Pro Pro Gly
                645                 650                 655

Tyr Lys Glu Asn Gly Gly Ile Phe Cys His Asn Asn Pro Trp Val Ile
            660                 665                 670

Ile Ala Glu Thr Val Val Gly Arg Gly Gly Arg Ala Phe Asp Tyr Tyr
        675                 680                 685

Lys Arg Ile Thr Pro Ala Tyr Arg Glu Asp Ile Ser Asp Val His Arg
        690                 695                 700

Thr Glu Pro Tyr Val Tyr Ala Gln Met Ile Ala Gly Lys Glu Ala Val
705                 710                 715                 720

Arg His Gly Glu Ala Lys Asn Ser Trp Leu Thr Gly Thr Ala Ala Trp
                725                 730                 735

Asn Phe Val Thr Val Ser Gln Tyr Leu Leu Gly Val Arg Pro Glu Tyr
                740                 745                 750

Asp Gly Leu Val Val Asp Pro Gln Ile Gly Pro Asp Val Pro Ser Phe
            755                 760                 765

Thr Val Thr Arg Val Ala Arg Gly Ala Thr Tyr Glu Ile Thr Val Thr
        770                 775                 780

Asn Ser Gly Val Asp Gly Ser Arg Gly Arg Leu Val Val Asp Gly Thr
785                 790                 795                 800

Pro Val Glu Gly Asn Leu Val Pro Tyr Ala Pro Ala Gly Ser Thr Val
                805                 810                 815

Arg Val Asp Val Thr Leu
                820

<210> SEQ ID NO 25
<211> LENGTH: 822
<212> TYPE: PRT
<213> ORGANISM: artificial
<220> FEATURE:
```

<223> OTHER INFORMATION: modified wildtype sequence

<400> SEQUENCE: 25

```
Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
            20                  25                  30

Phe Phe Ser Leu Leu Ser His Gln Ala Gly Gly Tyr Ser Phe Tyr Arg
        35                  40                  45

Asp Ala Lys Met Arg Arg Leu Thr Arg Tyr Arg Tyr Asn Asn Ile Pro
    50                  55                  60

Ala Asp Ala Gly Gly Arg Tyr Leu Tyr Val Asn Asp Gly Gly Asp Val
65                  70                  75                  80

Trp Thr Pro Ser Trp Leu Pro Val Lys Ala Asp Leu Asp His Phe Glu
                85                  90                  95

Ala Arg His Gly Leu Gly Tyr Ser Thr Ile Thr Gly Glu Arg Asn Gly
            100                 105                 110

Val Arg Val Glu Thr Leu Phe Phe Val Pro Val Gly Glu Asn Ala Glu
        115                 120                 125

Val Gln Lys Val Thr Val Thr Asn Thr Ser Asp Ser Tyr Lys Ser Leu
    130                 135                 140

Thr Leu Phe Ser Phe Val Glu Phe Cys Leu Trp Asn Ala Gln Asp Asp
145                 150                 155                 160

Met Thr Asn Tyr Gln Arg Asn Leu Val Ile Gly Val Glu Val Glu
                165                 170                 175

Gln Glu Ser Pro His Gly Ser Ala Ile Tyr His Lys Thr Glu Tyr Arg
            180                 185                 190

Glu Arg Arg Asn His Tyr Ala Val Phe Ala Val Asn Thr Gln Ala Glu
        195                 200                 205

Gly Phe Asp Thr Asp Arg Asp Thr Phe Val Gly Leu Tyr Asn Ser Leu
    210                 215                 220

Gly Glu Ala Ala Val Pro Leu Lys Gly Glu Ser Ala Asn Ser Val Ala
225                 230                 235                 240

Ser Gly Trp Tyr Pro Ile Gly Ser His Ser Val Ala Val Ser Leu Ala
                245                 250                 255

Pro Gly Glu Ser Arg Glu Leu Val Tyr Val Leu Gly Tyr Val Glu Asn
            260                 265                 270

Pro Asp Glu Glu Lys Trp Ala Asp Ala Ala Gln Val Val Asn Lys
        275                 280                 285

Glu Arg Ala His Ala Leu Leu Ser Arg Phe Ala Thr Ser Glu Gln Thr
    290                 295                 300

Asp Ala Ala Phe Ala Ala Leu Lys Asp Tyr Trp Thr Asp Leu Leu Ser
305                 310                 315                 320

Thr Tyr Ser Val Ser Ser Asn Asp Glu Lys Leu Asp Arg Met Val Asn
                325                 330                 335

Ile Trp Asn Gln Tyr Gln Cys Met Val Thr Phe Asn Met Ser Arg Ser
            340                 345                 350

Ala Ser Phe Phe Glu Thr Gly Ile Gly Arg Gly Met Gly Phe Arg Asp
        355                 360                 365

Ser Asn Gln Asp Leu Leu Gly Phe Val His Leu Ile Pro Glu Arg Ala
    370                 375                 380

Arg Glu Arg Ile Ile Asp Ile Ala Ser Thr Gln Phe Ala Asp Gly Ser
385                 390                 395                 400
```

```
Ala Tyr His Gln Tyr Gln Pro Leu Thr Lys Arg Gly Asn Asn Asp Ile
            405                 410                 415
Gly Ser Gly Phe Asn Asp Asp Pro Leu Trp Leu Ile Ala Gly Thr Ala
        420                 425                 430
Ala Tyr Ile Lys Glu Thr Gly Asp Phe Ser Ile Leu Asp Glu Pro Val
            435                 440                 445
Pro Phe Asp Asn Glu Pro Gly Ser Glu Val Pro Leu Phe Glu His Leu
450                 455                 460
Thr Arg Ser Phe Glu Phe Thr Val Thr His Arg Gly Pro His Gly Leu
465                 470                 475                 480
Pro Leu Ile Gly Arg Ala Asp Trp Asn Asp Cys Leu Asn Leu Asn Cys
                485                 490                 495
Phe Ser Thr Thr Pro Gly Glu Ser Phe Gln Thr Thr Glu Asn Gln Ala
                500                 505                 510
Gly Gly Val Ala Glu Ser Thr Phe Ile Ala Ala Gln Phe Val Leu Tyr
            515                 520                 525
Gly Glu Gln Tyr Ala Glu Leu Ala Ala Arg Arg Gly Leu Ala Asp Val
        530                 535                 540
Ala Asp Arg Ala Arg Gly His Val Ala Glu Met Arg Asp Ala Leu Leu
545                 550                 555                 560
Thr Asp Gly Trp Asp Gly Ser Trp Phe Leu Arg Ala Tyr Asp Tyr Tyr
                565                 570                 575
Gly Asn Pro Ile Gly Thr Asp Ala His Asp Glu Gly Lys Ile Trp Ile
                580                 585                 590
Glu Pro Gln Gly Phe Ala Val Met Ala Gly Val Gly Val Gly Glu Gly
            595                 600                 605
Pro Gln Asp Thr Asp Ala Pro Ala Ile Lys Ala Leu Asp Ser Val Asn
        610                 615                 620
Glu Met Leu Ala Thr Asp His Gly Ile Val Leu Gln Tyr Pro Ala Tyr
625                 630                 635                 640
Thr Thr Tyr Gln Val His Met Gly Glu Val Ser Thr Tyr Pro Pro Gly
                645                 650                 655
Tyr Lys Glu Asn Gly Gly Ile Phe Cys His Asn Asn Pro Trp Val Ile
                660                 665                 670
Ile Ala Glu Thr Val Val Gly Arg Gly Arg Ala Phe Asp Tyr Tyr
            675                 680                 685
Lys Arg Ile Thr Pro Ala Tyr Arg Glu Asp Ile Ser Asp Val His Arg
        690                 695                 700
Thr Glu Pro Tyr Val Tyr Ala Gln Met Ile Ala Gly Lys Glu Ala Val
705                 710                 715                 720
Arg His Gly Glu Ala Lys Asn Ser Trp Leu Thr Gly Thr Ala Ala Trp
                725                 730                 735
Asn Phe Val Thr Val Ser Gln Tyr Leu Leu Gly Val Arg Pro Glu Tyr
                740                 745                 750
Asp Gly Leu Val Val Asp Pro Gln Ile Gly Pro Asp Val Pro Ser Phe
            755                 760                 765
Thr Val Thr Arg Val Ala Arg Gly Ala Thr Tyr Glu Ile Thr Val Thr
        770                 775                 780
Asn Ser Gly Val Asp Gly Ser Arg Gly Arg Leu Val Val Asp Gly Thr
785                 790                 795                 800
Pro Val Glu Gly Asn Leu Val Pro Tyr Ala Pro Ala Gly Ser Thr Val
                805                 810                 815
Arg Val Asp Val Thr Leu
```

```
<210> SEQ ID NO 26
<211> LENGTH: 822
<212> TYPE: PRT
<213> ORGANISM: artificial
<220> FEATURE:
<223> OTHER INFORMATION: modified wildtype sequence

<400> SEQUENCE: 26
```

| | | | | | | | | | | | | | | |
|---|---|---|---|---|---|---|---|---|---|---|---|---|---|---|
|Met|Arg|Tyr|Gly|His|Phe|Asp|Asp|Glu|Ala|Arg|Glu|Tyr|Val|Ile|Thr|
|1| | | |5| | | | |10| | | | |15| |

| | | | | | | | | | | | | | | |
|---|---|---|---|---|---|---|---|---|---|---|---|---|---|---|
|Thr|Pro|His|Thr|Pro|Tyr|Pro|Trp|Ile|Asn|Tyr|Leu|Gly|Ser|Glu|Gln|
| | | |20| | | | |25| | | | |30| | |

| | | | | | | | | | | | | | | |
|---|---|---|---|---|---|---|---|---|---|---|---|---|---|---|
|Phe|Phe|Ser|Leu|Leu|Ser|His|Gln|Ala|Gly|Gly|Tyr|Ser|Phe|Tyr|Arg|
| | | |35| | | | |40| | | | |45| | |

Asp Ala Lys Met Arg Arg Leu Thr Arg Tyr Tyr Asn Asn Ile Pro
50              55                  60

Ala Asp Ala Gly Gly Arg Tyr Leu Tyr Val Asn Asp Gly Gly Asp Val
65              70                  75                  80

Trp Thr Pro Ser Trp Leu Pro Val Lys Ala Asp Leu Asp His Phe Glu
                85                  90                  95

Ala Arg His Gly Leu Gly Tyr Ser Thr Ile Thr Gly Glu Arg Asn Gly
                100                 105                 110

Val Arg Val Glu Thr Leu Phe Phe Val Pro Val Gly Glu Asn Ala Glu
            115                 120                 125

Val Gln Lys Val Thr Val Thr Asn Thr Ser Asp Ser Tyr Lys Ser Leu
130                 135                 140

Thr Leu Phe Ser Phe Val Glu Phe Cys Leu Trp Asn Ala Gln Asp Asp
145                 150                 155                 160

Met Thr Asn Tyr Gln Arg Asn Leu Val Ile Gly Glu Val Glu Val Glu
                165                 170                 175

Gln Glu Ser Pro His Gly Ser Ala Ile Tyr His Arg Thr Glu Tyr Arg
                180                 185                 190

Glu Arg Arg Asn His Tyr Ala Val Phe Ala Val Asn Thr Gln Ala Glu
            195                 200                 205

Gly Phe Asp Thr Asp Arg Asp Thr Phe Val Gly Leu Tyr Asn Ser Leu
210                 215                 220

Gly Glu Ala Ala Val Pro Leu Lys Gly Glu Ser Ala Asn Ser Val Ala
225                 230                 235                 240

Ser Gly Trp Tyr Pro Ile Gly Ser His Ser Val Ala Val Ser Leu Ala
                245                 250                 255

Pro Gly Glu Ser Arg Glu Leu Val Tyr Val Leu Gly Tyr Val Glu Asn
                260                 265                 270

Pro Asp Glu Glu Lys Trp Ala Asp Ala Ala Gln Val Val Asn Lys
            275                 280                 285

Glu Arg Ala His Ala Leu Leu Ser Arg Phe Ala Thr Ser Glu Gln Thr
            290                 295                 300

Asp Ala Ala Phe Ala Ala Leu Lys Asp Tyr Trp Thr Asp Leu Leu Ser
305                 310                 315                 320

Thr Tyr Ser Val Ser Ser Asn Asp Glu Lys Leu Asp Arg Met Val Asn
                325                 330                 335

Ile Trp Asn Gln Tyr Gln Cys Met Val Thr Phe Asn Met Ser Arg Ser
                340                 345                 350

Ala Ser Phe Phe Glu Thr Gly Ile Gly Arg Gly Met Gly Phe Arg Asp

```
                355                 360                 365
Ser Asn Gln Asp Leu Leu Gly Phe Val His Leu Ile Pro Glu Arg Ala
    370                 375                 380
Arg Glu Arg Ile Ile Asp Ile Ala Ser Thr Gln Phe Ala Asp Gly Ser
385                 390                 395                 400
Ala Tyr His Gln Tyr Gln Pro Leu Thr Lys Arg Gly Asn Asn Asp Ile
                405                 410                 415
Gly Ser Gly Phe Asn Asp Asp Pro Leu Trp Leu Ile Ala Gly Thr Ala
                420                 425                 430
Ala Tyr Ile Lys Glu Thr Gly Asp Phe Ser Ile Leu Asp Glu Pro Val
                435                 440                 445
Pro Phe Asp Asn Glu Pro Gly Ser Glu Val Pro Leu Phe Glu His Leu
            450                 455                 460
Thr Arg Ser Phe Glu Phe Thr Val Thr His Arg Gly Pro His Gly Leu
465                 470                 475                 480
Pro Leu Ile Gly Arg Ala Asp Trp Asn Asp Cys Leu Asn Leu Asn Cys
                485                 490                 495
Phe Ser Thr Thr Pro Gly Glu Ser Phe Gln Thr Thr Glu Asn Gln Ala
                500                 505                 510
Gly Gly Val Ala Glu Ser Thr Phe Ile Ala Ala Gln Phe Val Leu Tyr
            515                 520                 525
Gly Glu Gln Tyr Ala Glu Leu Ala Ala Arg Arg Gly Leu Ala Asp Val
        530                 535                 540
Ala Asp Arg Ala Arg Gly His Val Ala Glu Met Arg Asp Ala Leu Leu
545                 550                 555                 560
Thr Asp Gly Trp Asp Gly Ser Trp Phe Leu Arg Ala Tyr Asp Tyr Tyr
                565                 570                 575
Gly Asn Pro Ile Gly Thr Asp Ala His Asp Glu Gly Lys Ile Trp Ile
            580                 585                 590
Glu Pro Gln Gly Phe Ala Val Met Ala Gly Val Gly Val Gly Glu Gly
        595                 600                 605
Pro Gln Asp Thr Asp Ala Pro Ala Ile Lys Ala Leu Asp Ser Val Asn
    610                 615                 620
Glu Met Leu Ala Thr Asp His Gly Ile Val Leu Gln Tyr Pro Ala Tyr
625                 630                 635                 640
Thr Thr Tyr Gln Val His Met Gly Glu Val Ser Thr Tyr Pro Pro Gly
                645                 650                 655
Tyr Lys Glu Asn Gly Gly Ile Phe Cys His Asn Asn Pro Trp Val Ile
                660                 665                 670
Ile Ala Glu Thr Val Val Gly Arg Gly Gly Arg Ala Phe Asp Tyr Tyr
            675                 680                 685
Lys Arg Ile Thr Pro Ala Tyr Arg Glu Asp Ile Ser Asp Val His Arg
        690                 695                 700
Thr Glu Pro Tyr Val Tyr Ala Gln Met Ile Ala Gly Lys Glu Ala Val
705                 710                 715                 720
Arg His Gly Glu Ala Lys Asn Ser Trp Leu Thr Gly Thr Ala Ala Trp
                725                 730                 735
Asn Phe Val Thr Val Ser Gln Tyr Leu Leu Gly Val Arg Pro Glu Tyr
                740                 745                 750
Asp Gly Leu Val Val Asp Pro Gln Ile Gly Pro Asp Val Pro Ser Phe
            755                 760                 765
Thr Val Thr Arg Val Ala Arg Gly Ala Thr Tyr Glu Ile Thr Val Thr
        770                 775                 780
```

```
Asn Ser Gly Val Asp Gly Ser Arg Gly Arg Leu Val Val Asp Gly Thr
785                 790                 795                 800

Pro Val Glu Gly Asn Leu Val Pro Tyr Ala Pro Ala Gly Ser Thr Val
            805                 810                 815

Arg Val Asp Val Thr Leu
            820

<210> SEQ ID NO 27
<211> LENGTH: 822
<212> TYPE: PRT
<213> ORGANISM: artificial
<220> FEATURE:
<223> OTHER INFORMATION: modified wildtype sequence

<400> SEQUENCE: 27

Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
            20                  25                  30

Phe Phe Ser Leu Leu Ser His Gln Ala Gly Gly Tyr Ser Phe Tyr Arg
        35                  40                  45

Asp Ala Lys Met Arg Arg Leu Thr Arg Tyr Arg Tyr Asn Asn Ile Pro
50                  55                  60

Ala Asp Ala Gly Gly Arg Tyr Leu Tyr Val Asn Asp Gly Gly Asp Val
65                  70                  75                  80

Trp Thr Pro Ser Trp Leu Pro Val Lys Ala Asp Leu Asp His Phe Glu
                85                  90                  95

Ala Arg His Gly Leu Gly Tyr Ser Thr Ile Thr Gly Glu Arg Asn Gly
            100                 105                 110

Val Arg Val Glu Thr Leu Phe Phe Val Pro Val Gly Asn Ala Glu
        115                 120                 125

Val Gln Lys Val Thr Val Thr Asn Thr Ser Asp Ser Tyr Lys Ser Leu
130                 135                 140

Thr Leu Phe Ser Phe Val Glu Phe Cys Leu Trp Asn Ala Gln Asp Asp
145                 150                 155                 160

Met Thr Asn Tyr Gln Arg Asn Leu Val Ile Gly Glu Val Glu Val Glu
                165                 170                 175

Gln Glu Ser Pro His Gly Ser Ala Ile Tyr His Lys Thr Glu Tyr Arg
            180                 185                 190

Glu Arg Arg Asn His Tyr Ala Val Phe Ala Val Asn Thr Gln Ala Glu
        195                 200                 205

Gly Phe Asp Thr Asp Arg Asp Thr Phe Val Gly Leu Tyr Asn Ser Leu
210                 215                 220

Gly Glu Ala Ala Val Pro Leu Lys Gly Glu Ser Ala Asn Ser Val Ala
225                 230                 235                 240

Ser Gly Trp Tyr Pro Ile Gly Ser His Ser Val Ala Val Ser Leu Ala
                245                 250                 255

Pro Gly Glu Ser Arg Glu Leu Val Tyr Val Leu Gly Tyr Val Glu Asn
            260                 265                 270

Pro Asp Glu Glu Lys Trp Ala Asp Ala Ala Gln Val Val Asn Lys
        275                 280                 285

Glu Arg Ala His Ala Leu Leu Ser Arg Phe Ala Thr Ser Glu Gln Thr
290                 295                 300

Asp Ala Ala Phe Ala Ala Leu Lys Asp Tyr Trp Thr Asn Leu Leu Ser
305                 310                 315                 320
```

```
Thr Tyr Ser Val Ser Ser Asn Asp Glu Lys Leu Asp Arg Met Val Asn
            325                 330                 335

Ile Trp Asn Gln Tyr Gln Cys Met Val Thr Phe Asn Met Ser Arg Ser
            340                 345                 350

Ala Ser Phe Phe Glu Thr Gly Ile Gly Arg Gly Met Gly Phe Arg Asp
            355                 360                 365

Ser Asn Gln Asp Leu Leu Gly Phe Val His Leu Ile Pro Glu Arg Ala
            370                 375                 380

Arg Glu Arg Ile Ile Asp Ile Ala Ser Thr Gln Phe Ala Asp Gly Ser
385                 390                 395                 400

Ala Tyr His Gln Tyr Gln Pro Leu Thr Lys Arg Gly Asn Asn Asp Ile
            405                 410                 415

Gly Ser Gly Phe Asn Asp Asp Pro Leu Trp Leu Ile Ala Gly Thr Ala
            420                 425                 430

Ala Tyr Ile Lys Glu Thr Gly Asp Phe Ser Ile Leu Asp Glu Pro Val
            435                 440                 445

Pro Phe Asp Asn Glu Pro Gly Ser Glu Val Pro Leu Phe Glu His Leu
            450                 455                 460

Thr Arg Ser Phe Glu Phe Thr Val Glu His Arg Gly Pro His Gly Leu
465                 470                 475                 480

Pro Leu Ile Gly Arg Ala Asp Trp Asn Asp Cys Leu Asn Leu Asn Cys
            485                 490                 495

Phe Ser Thr Thr Pro Gly Glu Ser Phe Gln Thr Thr Glu Asn Gln Val
            500                 505                 510

Gly Gly Val Ala Glu Ser Thr Phe Ile Ala Ala Gln Phe Val Leu Tyr
            515                 520                 525

Gly Glu Gln Tyr Ala Glu Leu Ala Ala Arg Arg Gly Leu Ala Asp Val
            530                 535                 540

Ala Asp Arg Ala Arg Gly His Val Ala Glu Met Arg Asp Ala Leu Leu
545                 550                 555                 560

Thr Asp Gly Trp Asp Gly Ser Trp Phe Leu Arg Ala Tyr Asp Tyr Tyr
            565                 570                 575

Gly Asn Pro Ile Gly Thr Asp Ala His Asp Glu Gly Lys Ile Trp Ile
            580                 585                 590

Glu Pro Gln Gly Phe Ala Val Met Ala Gly Val Gly Val Gly Glu Gly
            595                 600                 605

Pro Gln Asp Thr Asp Ala Pro Ala Ile Lys Ala Leu Asp Ser Val Asn
            610                 615                 620

Glu Met Leu Ala Thr Asp His Gly Met Val Leu Gln Tyr Pro Ala Tyr
625                 630                 635                 640

Thr Thr Tyr Gln Val His Met Gly Glu Val Ser Thr Tyr Pro Pro Gly
            645                 650                 655

Tyr Lys Glu Asn Gly Gly Ile Phe Cys His Asn Asn Pro Trp Val Ile
            660                 665                 670

Ile Ala Glu Thr Val Val Gly Arg Gly Gly Arg Ala Phe Asp Tyr Tyr
            675                 680                 685

Lys Arg Ile Thr Pro Ala Tyr Arg Glu Asp Ile Ser Asp Val His Arg
            690                 695                 700

Thr Glu Pro Tyr Val Tyr Ala Gln Met Ile Ala Gly Lys Glu Ala Val
705                 710                 715                 720

Arg His Gly Glu Ala Lys Asn Ser Trp Leu Thr Gly Thr Ala Ala Trp
            725                 730                 735
```

```
Asn Phe Val Thr Val Ser Gln Tyr Leu Leu Gly Val Arg Pro Glu Tyr
                740                 745                 750

Asp Gly Leu Val Val Asp Pro Gln Ile Gly Pro Asp Val Pro Ser Phe
            755                 760                 765

Thr Val Thr Arg Val Ala Arg Gly Ala Thr Tyr Glu Ile Thr Val Thr
        770                 775                 780

Asn Ser Gly Val Asp Gly Ser Arg Gly Arg Leu Val Val Asp Gly Thr
785                 790                 795                 800

Pro Val Glu Gly Asn Leu Val Pro Tyr Ala Pro Ala Gly Ser Thr Val
                805                 810                 815

Arg Val Asp Val Thr Leu
            820

<210> SEQ ID NO 28
<211> LENGTH: 822
<212> TYPE: PRT
<213> ORGANISM: artificial
<220> FEATURE:
<223> OTHER INFORMATION: modified wildtype sequence

<400> SEQUENCE: 28

Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
            20                  25                  30

Phe Phe Ser Leu Leu Ser His Gln Ala Gly Gly Tyr Ser Phe Tyr Arg
        35                  40                  45

Asp Ala Lys Met Arg Arg Leu Thr Arg Tyr Arg Tyr Asn Asn Ile Pro
    50                  55                  60

Ala Asp Ala Gly Gly Arg Tyr Leu Tyr Val Asn Asp Gly Gly Asp Val
65                  70                  75                  80

Trp Thr Pro Ser Trp Leu Pro Val Lys Ala Asp Leu Asp His Phe Glu
                85                  90                  95

Ala Arg His Gly Leu Gly Tyr Ser Thr Ile Thr Gly Glu Arg Asn Gly
            100                 105                 110

Val Arg Val Glu Thr Leu Phe Phe Val Pro Val Gly Glu Asn Ala Glu
        115                 120                 125

Val Gln Lys Val Thr Val Thr Asn Thr Ser Asp Ser Tyr Lys Ser Leu
130                 135                 140

Thr Leu Phe Ser Phe Val Glu Phe Cys Leu Trp Asn Ala Gln Asp Asp
145                 150                 155                 160

Met Thr Asn Tyr Gln Arg Asn Leu Val Ile Gly Glu Val Glu Val Glu
                165                 170                 175

Gln Glu Ser Pro His Gly Ser Ala Ile Tyr His Lys Thr Glu Tyr Arg
            180                 185                 190

Glu Arg Arg Asn His Tyr Ala Val Phe Ala Val Asn Thr Gln Ala Glu
        195                 200                 205

Gly Phe Asp Thr Asp Arg Asp Thr Phe Val Gly Leu Tyr Asn Ser Leu
210                 215                 220

Gly Glu Ala Ala Val Pro Leu Lys Gly Glu Ser Ala Asn Ser Val Ala
225                 230                 235                 240

Ser Gly Trp Tyr Pro Ile Gly Ser His Ser Val Ala Val Ser Leu Ala
                245                 250                 255

Pro Gly Glu Ser Arg Glu Leu Val Tyr Val Leu Gly Tyr Val Glu Asn
            260                 265                 270
```

```
Pro Asp Glu Glu Lys Trp Ala Asp Asp Ala Ala Gln Val Val Asn Lys
            275                 280                 285

Glu Arg Ala His Ala Leu Leu Ser Arg Phe Ala Thr Ser Glu Gln Thr
    290                 295                 300

Asp Ala Ala Phe Ala Ala Leu Lys Asp Tyr Trp Thr Asn Leu Leu Ser
305                 310                 315                 320

Thr Tyr Ser Val Ser Ser Asn Asp Glu Lys Leu Asp Arg Met Val Asn
                325                 330                 335

Ile Trp Asn Gln Tyr Gln Cys Met Val Thr Phe Asn Met Ser Arg Ser
            340                 345                 350

Ala Ser Phe Phe Glu Thr Gly Ile Gly Arg Gly Met Gly Phe Arg Asp
        355                 360                 365

Ser Asn Gln Asp Leu Leu Gly Phe Val His Leu Ile Pro Glu Arg Ala
    370                 375                 380

Arg Glu Arg Ile Ile Asp Ile Ala Ser Thr Gln Phe Ala Asp Gly Ser
385                 390                 395                 400

Ala Tyr His Gln Tyr Gln Pro Leu Thr Lys Arg Gly Asn Asn Asp Ile
                405                 410                 415

Gly Ser Gly Phe Asn Asp Asp Pro Leu Trp Leu Ile Ala Gly Thr Ala
            420                 425                 430

Ala Tyr Ile Lys Glu Thr Gly Asp Phe Ser Ile Leu Asp Glu Pro Val
        435                 440                 445

Pro Phe Asp Asn Glu Pro Gly Ser Glu Val Pro Leu Phe Glu His Leu
    450                 455                 460

Thr Arg Ser Phe Glu Phe Thr Val Thr His Arg Gly Pro His Gly Leu
465                 470                 475                 480

Pro Leu Ile Gly Arg Ala Asp Trp Asn Asp Cys Leu Asn Leu Asn Cys
                485                 490                 495

Phe Ser Thr Thr Pro Gly Glu Ser Phe Gln Thr Thr Glu Asn Gln Ala
            500                 505                 510

Gly Gly Val Ala Glu Ser Thr Phe Ile Ala Ala Gln Phe Val Leu Tyr
        515                 520                 525

Gly Glu Gln Tyr Ala Glu Leu Ala Ala Arg Arg Gly Leu Ala Asp Val
    530                 535                 540

Ala Asp Arg Ala Arg Gly His Val Ala Glu Met Arg Asp Ala Leu Leu
545                 550                 555                 560

Thr Asp Gly Trp Asp Gly Ser Trp Phe Leu Arg Ala Tyr Asp Tyr Tyr
                565                 570                 575

Gly Asn Pro Ile Gly Thr Asp Ala His Asp Glu Gly Lys Ile Trp Ile
            580                 585                 590

Glu Pro Gln Gly Phe Ala Val Met Ala Gly Val Gly Val Gly Glu Gly
        595                 600                 605

Pro Gln Asp Thr Asp Ala Pro Ala Ile Lys Ala Leu Asp Ser Val Asn
    610                 615                 620

Glu Met Leu Ala Thr Asp His Gly Ile Val Leu Gln Tyr Pro Ala Tyr
625                 630                 635                 640

Thr Thr Tyr Gln Val His Met Gly Glu Val Ser Thr Tyr Pro Pro Gly
                645                 650                 655

Tyr Lys Glu Asn Gly Gly Ile Phe Cys His Asn Asn Pro Trp Val Ile
            660                 665                 670

Ile Ala Glu Thr Val Val Gly Arg Gly Arg Ala Phe Asp Tyr Tyr
        675                 680                 685
```

```
        Lys Arg Ile Thr Pro Ala Tyr Arg Glu Asp Ile Ser Asp Val His Arg
            690             695             700

Thr Glu Pro Tyr Val Tyr Ala Gln Met Ile Ala Gly Lys Glu Ala Val
        705             710             715             720

Arg His Gly Glu Ala Lys Asn Ser Trp Leu Thr Gly Thr Ala Ala Trp
                        725             730             735

Asn Phe Val Thr Val Ser Gln Tyr Leu Leu Gly Val Arg Pro Glu Tyr
                        740             745             750

Asp Gly Leu Val Val Asp Pro Gln Ile Gly Pro Asp Val Pro Ser Phe
                    755             760             765

Thr Val Thr Arg Val Ala Arg Gly Ala Thr Tyr Glu Ile Thr Val Thr
        770                 775             780

Asn Ser Gly Val Asp Gly Ser Arg Gly Arg Leu Val Val Asp Gly Thr
        785             790             795             800

Pro Val Glu Gly Asn Leu Val Pro Tyr Ala Pro Ala Gly Ser Thr Val
                        805             810             815

Arg Val Asp Val Thr Leu
                        820
```